(12) United States Patent
Hess et al.

(10) Patent No.: US 12,419,538 B2
(45) Date of Patent: Sep. 23, 2025

(54) SYSTEMS AND METHODS FOR RESPIRATION-CONTROLLED VIRTUAL EXPERIENCES

(71) Applicant: Children's Hospital Medical Center, Cincinnati, OH (US)

(72) Inventors: Abby Victoria Hess, Cincinnati, OH (US); Blake Lane, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 18/732,074

(22) Filed: Jun. 3, 2024

(65) Prior Publication Data

US 2024/0315593 A1    Sep. 26, 2024

Related U.S. Application Data

(62) Division of application No. 16/240,179, filed on Jan. 4, 2019, now Pat. No. 11,998,313.

(Continued)

(51) Int. Cl.
*A61B 5/087*    (2006.01)
*A61B 5/00*    (2006.01)
(Continued)

(52) U.S. Cl.
CPC ............ *A61B 5/087* (2013.01); *A61B 5/0803* (2013.01); *A61B 5/097* (2013.01); *A61B 5/165* (2013.01);
(Continued)

(58) Field of Classification Search
CPC ....... A61B 5/087; A61B 5/0803; A61B 5/097; A61B 5/165; A61B 5/4839; A61B 5/4848;
(Continued)

(56) References Cited

U.S. PATENT DOCUMENTS 5,398,695 A    3/1995    Anderson et al.
5,531,096 A    7/1996    Castor
(Continued)

FOREIGN PATENT DOCUMENTS

EP    0900102 B1    7/2004

OTHER PUBLICATIONS

Kain, Zeev N. et al., "Parental Presence during Induction of Anesthesia versus Sedative: Premedication Which Intervention Is More Effective?," The Journal of the American Society of Anesthesiologists 89.5 (1998), 1147-1156.

(Continued)

*Primary Examiner* — Malina D. Blaise
(74) *Attorney, Agent, or Firm* — Bose McKinney & Evans LLP

(57) ABSTRACT

Disclosed herein are systems and methods for respiration-controlled virtual experiences. In an embodiment, a controller presents a virtual experience via a user interface that is perceptible to a user. The controller receives a respiration-data stream from a respiration device with which the user is operably engaged. The respiration-data stream includes one or more respiration-parameter values of one or more respiration parameters associated with ongoing respiration of the user. The controller updates the virtual experience based at least in part on the one or more respiration-parameter values in the respiration-data stream. The virtual experience includes a plurality of sequential phases that have an associated phase sequence. Among the sequential phases is an active-induction phase that corresponds in time to the user receiving anesthetic induction via the respiration device, as well as one or more phases that each precede the active-induction phase.

12 Claims, 50 Drawing Sheets

Related U.S. Application Data

(60) Provisional application No. 62/614,103, filed on Jan. 5, 2018.

(51) Int. Cl.

| | |
|---|---|
| *A61B 5/08* | (2006.01) |
| *A61B 5/097* | (2006.01) |
| *A61B 5/16* | (2006.01) |
| *A61M 16/01* | (2006.01) |
| *A61M 16/06* | (2006.01) |
| *A63F 13/21* | (2014.01) |
| *A63F 13/212* | (2014.01) |
| *G06F 3/01* | (2006.01) |
| *A61M 21/00* | (2006.01) |

(52) U.S. Cl.
CPC .......... *A61B 5/4839* (2013.01); *A61B 5/4848* (2013.01); *A61B 5/486* (2013.01); *A61B 5/6898* (2013.01); *A61B 5/744* (2013.01); *A61B 5/7445* (2013.01); *A61B 5/7475* (2013.01); *A61M 16/01* (2013.01); *A61M 16/06* (2013.01); *A63F 13/21* (2014.09); *A63F 13/212* (2014.09); *G06F 3/011* (2013.01); *A61B 2503/06* (2013.01); *A61M 2021/005* (2013.01)

(58) Field of Classification Search
CPC ....... A61B 5/486; A61B 5/6898; A61B 5/744; A61B 5/7445; A61B 5/7475; A61B 2503/06; A63F 13/21; A63F 13/212; A61M 16/01; A61M 16/06; A61M 2021/005; G06F 3/011

See application file for complete search history.

(56) References Cited

U.S. PATENT DOCUMENTS

| | | | |
|---|---|---|---|
| 5,610,674 A | 3/1997 | Martin | |
| 5,697,363 A | 12/1997 | Hart | |
| 5,705,735 A | 1/1998 | Acorn | |
| 5,794,612 A | 8/1998 | Wachter et al. | |
| 5,865,172 A | 2/1999 | Butler et al. | |
| 5,925,831 A | 7/1999 | Storsved | |
| 5,937,852 A | 8/1999 | Butler et al. | |
| 6,019,732 A | 2/2000 | Volgyesi | |
| 6,073,628 A | 6/2000 | Butler et al. | |
| 6,401,757 B1 | 6/2002 | Pentz et al. | |
| 6,463,928 B1 | 10/2002 | Buisson | |
| 6,595,207 B1 | 7/2003 | McDonald et al. | |
| 6,697,363 B1 | 2/2004 | Carr | |
| 6,857,427 B2 | 2/2005 | Ziegler et al. | |
| 7,233,904 B2 | 6/2007 | Luisi | |
| 7,350,520 B1 | 4/2008 | Richard-Bey | |
| 7,886,738 B2 | 2/2011 | Walker | |
| 8,333,111 B2 | 12/2012 | Hietala | |
| 8,459,261 B2 | 6/2013 | Ricciardelli et al. | |
| 8,460,203 B2 | 6/2013 | Ricciardelli | |
| 9,259,542 B2 | 2/2016 | Acker et al. | |
| 9,452,317 B2* | 9/2016 | Arkush .................. A63F 13/20 |
| 9,717,991 B2 | 8/2017 | Li et al. | |
| 11,351,418 B2* | 6/2022 | Klee .................. A63B 71/0622 |
| 11,998,313 B2 | 6/2024 | Hess et al. | |
| 2002/0120207 A1 | 8/2002 | Hoffman | |
| 2002/0124843 A1 | 9/2002 | Skiba et al. | |
| 2002/0178783 A1 | 12/2002 | Miller et al. | |
| 2004/0186390 A1 | 9/2004 | Ross et al. | |
| 2006/0081248 A1 | 4/2006 | McDonald | |
| 2006/0118110 A1 | 6/2006 | Gerder-Kallisch et al. | |
| 2006/0149216 A1 | 7/2006 | Sherman | |
| 2006/0196503 A1 | 9/2006 | Bardel | |
| 2007/0048691 A1 | 3/2007 | Brown | |
| 2009/0143996 A1 | 6/2009 | Karlsson et al. | |
| 2009/0250064 A1 | 10/2009 | Strawder | |
| 2015/0059739 A1* | 3/2015 | Aslam .............. A61M 15/0065 128/202.22 |
| 2015/0114388 A1* | 4/2015 | Fernandez ........ A61M 16/0841 128/202.13 |
| 2016/0199602 A1* | 7/2016 | Fernandez .......... A61M 16/021 128/202.13 |
| 2016/0279373 A1* | 9/2016 | Miller .................. A61M 16/01 |
| 2017/0348562 A1* | 12/2017 | Jung ..................... A61B 5/112 |
| 2018/0292888 A1* | 10/2018 | Slepian ............... A61B 5/4836 |
| 2018/0318643 A1* | 11/2018 | Klee ...................... A61B 5/097 |
| 2019/0134460 A1* | 5/2019 | Cheu .................... A63F 13/245 |
| 2019/0209044 A1* | 7/2019 | Hess .................... A63F 13/212 |
| 2019/0217031 A1* | 7/2019 | Kuck ................. A61M 16/022 |
| 2020/0360764 A1* | 11/2020 | Smith ............. A63B 21/00178 |
| 2022/0062580 A1* | 3/2022 | Miskovic .............. A61M 21/00 |
| 2024/0315593 A1* | 9/2024 | Hess .................... A61B 5/4848 |

OTHER PUBLICATIONS

Kain, Zeev N. et al., "Preoperative anxiety and emergence delirium and postoperative maladaptive behaviors," Anesthesia & Analgesia 99.6 (2004), 1648-1654.

Przybylo, H.J., S.E. Tarbell and G.W. Stevenson, "Mask fear in children presenting for anesthesia: aversion, phobia, or both?," Pediatric Anesthesia 15.5 (2005), 366-370.

Patel, Anuradha et al., "Distraction with a hand-held video game reduces pediatric preoperative anxiety," Pediatric Anesthesia 16.10 (2006), 1019-1027.

Aydin, Tayfun et al., "Do not mask the mask: use it as a premedicant," Pediatric Anesthesia 18.2 (2008), 107-112.

Varughese, Anna M. et al., "Factors predictive of poor behavioral compliance during inhaled induction in children," Anesthesia & Analgesia 107.2 (2008), 413-421.

Chorney, Jill MacLaren, and Zeev N. Kain, "Behavioral analysis of children's response to induction of anesthesia," Anesthesia & Analgesia 109.5 (2009), 1434-1440.

Yuki, Koichi, and Dima G. Daaboul, "Postoperative maladaptive behavioral changes in children," Middle East J Anesthesiol 21.2 (2011), 183-9.

Wohlheiter, Karen A., and Lynnda M. Dahlquist, "Interactive versus passive distraction for acute pain management in young children: The role of selective attention and development," Journal of Pediatric Psychology (2012), jss 108.

Nilsson, Stefan et al., "Active and passive distraction in children undergoing wound dressings," Journal of Pediatric Nursing 28.2 (2013), 158-166.

"Hospital Entertainment System Helps Ease Kids' Anxiety before Surgery," retrieved on Oct. 24, 2018 from https://www.nbcdfw.com/news/health/Hospital-Entertainment-System-Helps-Ease-Kids-Anxiety-Before-Surgery-433628773. html, 3 pages.

GE Healthcare Quick Guide, Patient Spirometry, DOC00604362 Jun. 2009, 2 pages.

GE Healthcare, Aisys CS2, Advanced and Sustainable Anaesthesia Care, DOC1261976 rev3 Sep. 2013, 5 pages.

Samuel Rodriguez, MD, Jeremy H. Tsui, Samuel Y. Jiang, BA and Thomas J. Caruso, MD, Interactive video game build for mask induction in pediatric patents, Can J Anesth/J Can Anesth (2017) 64: 1073-1074, 2 pages.

Spire Health Platform, Real-time health monitoring and interventions for consumers, employees & patients, retrieved on Oct. 28, 2018 from https://spire.io/pages/platform, 4 pages.

Equivital, EQ02 LifeMonitor, released Feb. 2012, 2 pages.

Vandrico Inc., Wearable Devices that have a Respiratory Monitor, retrieved on Oct. 28, 2018, from https://vandrico.com/wearable/device-categories/components/respiratory-monitor, 5 pages.

Medtronic, Continuous Respiratory Rate Monitoring, retrieved on Nov. 6, 2019 from http://www.medtronic.com/covidien/en-us/clinical-solutions/respiratory-compromise/surveillance-monitoring/continuous-respiratory-rate-monitoring.html, 4 pages.

Xethru by Novelda, X4M200 Respiration Sensor, retrieved on Nov. 6, 2018 from https://www.xelthru.com/x4m200-respiration-sensor.html, 4 pages.

(56) References Cited

OTHER PUBLICATIONS

Sensor Technology—Respiratory Rate Monitor—PMD Solutions, retrieved on Nov. 6, 2018 from http://www.pmd-solutions.com/sensortechnology, 3 pages.
Wearable Technologies, Just Breathe—Breath Analyzing Tech for Sports, Healthcare and Wellness, retrieved on Nov. 6, 2018 from https://www.wearable-technologies.com/2015/02/just-breathe-breath-analyzing-tech-for-sports-healthcare-and-wellness, 2 pages.
Isansys: products, retrieved on Nov. 6, 2018 from http://www.isansys.com/en/products, 1 page.
Respiration (PZT) Sensor—PLUX Store, retrieved on Nov. 6, 2018 from https://store.plux.info/bitalino-sensors/40-respiration-pzt-sensor.html, 4 pages.
Vernier Software & Technology, Go Direct Respiration Belt, retrieved on Nov. 6, 2018 from https://www.vernier.com/products/sensors/respiration-monitors/gdx-rb, 6 pages.
The Guardian, And breath: the computer games helping kids relax, retrieved on Nov. 6, 2018 from https://www.theguardian.com/lifeandstyle/2016/oct/31/breathtaking-winners-the-computer-games-helping-kids-relax, 4 pages.
Health & Wellbeing, Zenytime games are controlled by your breathing to improve wellbeing, retrieved on Nov. 6, 2018 from https://hewatlas.com/zenytime/33802, 3 pages.
Health & Rehab., GroovTube Uses Games and Music to Train Breath Control and Oral Motor Skills, retrieved on Nov. 6, 2018 from https://www.fitness-gaming.com/news/health-and-rehab/groovtube-uses-games-and-music-to-train-breath-control-ad-oral-motor-skills.html, 17 pages.
Pixelscanner, BreathVR, retrieved on Nov. 6, 2018 from http://alumni.media.mit.edu/~sra/breathvr.html, 1 page.
Deep VR, Deep is a meditative VR game controlled by breathing, retrieved on Nov. 6, 2018 from http://www.exploredeep.com/#about-deep, 10 pages.
Games & Hardware, Breathing Games, retrieved on Nov. 6, 2018 from https://breathinggames.net/?q=fr/jeux-materiel, 5 pages.
Breathing Labs, Video Games That Motivate Kids To Do Breathing Exercises, retrieved on Nov. 6, 2018 from https://www.breathinglabs.com/about-company/breathing-games, 7 pages.
Sunghee Joo, Doochul Shin and Changho Song, Medical Science Monitor, The Effects of Game-Based Breathing Exercise on Pulmonary Function in Stroke Patients: A Preliminary Study, retrieved on Nov. 6, 2018 from http://www.medscimonit.com/abstract/index/idArt/893420, 6 pages.
Lars Sundelin, Janis Beinerts, Trieuvy Luu and Sebastian Aumer, ANNA—breathing assistant for sedation retrieved on Nov. 6, 2018 from https://designawards.core77.com/Interaction/31881/ANNA-breathing-assistant-for-sedation, 15 pages.

* cited by examiner

FIG. 13

SYSTEMS AND METHODS FOR RESPIRATION-CONTROLLED VIRTUAL EXPERIENCES

CROSS REFERENCE TO RELATED APPLICATIONS

This application is a divisional of U.S. patent application Ser. No. 16/240,179, filed Jan. 4, 2019, which claims the benefit of U.S. Provisional Patent Application No. 62/614,103, filed Jan. 5, 2018 and entitled "System for Improving Pediatric Patient Receptiveness to a Mask During Anesthesia Induction," the entire disclosures of which are hereby incorporated herein by reference.

TECHNICAL FIELD

The present disclosure relates to improving patient experiences and outcomes in connection with respiration-related medical devices, and in particular to systems and methods for respiration-controlled virtual experiences.

BACKGROUND

Anesthesia and surgery can produce high anxiety for patients and their families. Multiple research studies have demonstrated that placement of the mask during anesthesia induction is when children experience the highest level of anxiety pre-operative. When attempting to place a mask on a child's face, the child may become fearful, uncooperative, or combative. Anxiety and poor compliance during anesthesia inductions have been associated with many negative outcomes. These outcomes may include combative behaviors resulting in safety concerns during the induction, prolonged time required to accomplish the induction, increased delirium when awaking from anesthesia, increased reports of post-operative pain, negative behavioral changes after discharge to home, and aversion or phobias associated with the anesthesia mask.

Patients may display a variety of negative behaviors during anesthesia inductions. These behaviors can include verbalizing worry or refusal, crying, turning away from the mask, pushing the staff or mask away, burying their face, screaming, kicking/flailing/struggling, and requiring restraint. When caregivers anticipate that children may have difficulty with induction, patients may be given an anxiolytic medication. These medications often have side effects, however, and are not always appropriate to prescribe for all patients due to medical conditions, prior adverse reactions, or the procedure planned, among other reasons. Behavioral interventions (e.g., watching movies, playing video games, and storytelling) can often be helpful in decreasing patients' fear and anxiety during anesthesia induction. Despite medication and behavioral interventions, poor compliance with the mask is still common. A behavioral observation study conducted at Cincinnati Children's Hospital Medical Center demonstrated that 21% of children showed only moderate behavioral compliance with the mask (where 1 to 3 of the negative behaviors listed above were exhibited during induction), and 22% exhibited poor behavioral compliance (displaying four or more of the above-listed negative induction behaviors). This is similar to what has been reported at other pediatric care facilities.

Overview

Disclosed herein are systems and methods for respiration-controlled virtual experiences. One example of a virtual experience is a video game. In an embodiment, a video-game is controllable by a patient at least in part by way of respiration when operably engaged with an anesthesia mask. While anesthesia induction is not widely considered to be a painful experience, children do sometimes complain of discomfort associated with having a mask covering their face, the odor of the anesthesia gas, and/or in one or more other ways that reflect their general anxiety. Multiple research studies have suggested that active distraction, such as playing video games, facilitates improved management of anxiety, discomfort, and pain in pediatric patients.

Video game systems are relatively inexpensive, widely available, and are enjoyed by many children. Video games are sometimes used during anesthesia inductions, but for the most part they do not effectively encourage positive interaction with the anesthesia mask. A game in which a child or other patient interacts with the mask in a manner that controls the game by way of, e.g., voice commands and/or respiring into the mask provides superior mask acceptance and distraction. One or more games of this nature are described in U.S. Patent Application Publication No. US 2016/0199602 A1, published Jul. 14, 2016 and entitled "Adapter for an Anesthesia Mask or Other Mask," the entire disclosure of which is hereby incorporated herein by reference.

In general, the present systems and methods represent ways in which technology is useable during anesthesia induction and other respiration-related medical treatment to provide fun and interactive distractions to children during a time of high fear and anxiety in a manner that also facilitates their proper engagement with an anesthesia mask or other respiration-related medical devices and treatments. This improves induction experiences and post-operative outcomes, among other benefits. The present systems and methods include embodiments in which a user (e.g., a pediatric surgery patient) is guided through a series of sequential game phases that start out relatively easy and build naturally towards an active-induction phase in which the user applies the skills they have practiced and improved upon in the one or more preceding phases to achieve an anesthesia experience that is relatively painless and anxiety-free. Thus far, feedback from patients and their caregivers and families has been quite positive.

One embodiment takes the form of a method that includes a controller presenting a virtual experience via a user interface, where the user interface is perceptible to a user. The method also includes the controller receiving a respiration-data stream from a respiration device with which the user is operably engaged. The respiration-data stream includes one or more respiration-parameter values of one or more respiration parameters that are each associated with the ongoing respiration of the user. The method also includes the controller updating the virtual experience based at least in part on the one or more respiration-parameter values in the respiration-data stream. The virtual experience includes multiple sequential phases that have an associated phase sequence. The sequential phases include an active-induction phase that corresponds in time to the user receiving anesthetic induction via the respiration device. The sequential phases also include a preceding-phases set of one or more phases that each precede the active-induction phase in the phase sequence.

Another embodiment takes the form of a controller that includes a user-interface-communication module that is configured to operably communicate with a user interface that is perceptible to a user. The controller also includes a respiration-parameter module that is configured to output a respiration-data stream that is reflective of one or more respiration-parameter values of one or more respiration parameters associated with the ongoing respiration of the user via a respiration device with which the user is operably engaged. The controller also includes a processor that is configured to operably communicate with both the user-interface-communication module and the respiration-device-sensor module and that is further configured to carry out at least the functions that are listed in the preceding paragraph. Yet another embodiment takes the form of a non-transitory computer-readable medium (CRM) having stored thereon instructions executable by a processor for carrying out at least those functions. Still another embodiment takes the form of a system that includes a communication interface, a processor, and data storage containing instructions executable by the processor for carrying out at least those functions.

Another embodiment takes the form of a method that includes a controller presenting a virtual experience via a user interface, where the user interface is perceptible to a user. The method also includes the controller receiving a respiration-data stream from a respiration device with which the user is operably engaged. The respiration-data stream includes one or more respiration-parameter values of one or more respiration parameters associated with ongoing respiration of the user. The method also includes the controller updating the virtual experience based at least in part on the one or more respiration-parameter values in the respiration-data stream. The virtual experience includes multiple sequential phases that have an associated phase sequence. The sequential phases include an active-treatment phase that corresponds in time to the user receiving one or both of at least one medicament and at least one treatment via the respiration device. The sequential phases also include a preceding-phases set of one or more phases that each precede the active-treatment phase in the phase sequence. In various different embodiments, the respiration device may be, may include, or may be included in a positive-airway-pressure (PAP) device such as a biphasic PAP (BiPAP) device or a continuous PAP (CPAP) device, a nebulizer, an incentive spirometry device, and/or one or more other types of respiratory devices.

Another embodiment takes the form of a controller that includes a user-interface-communication module that is configured to operably communicate with a user interface that is perceptible to a user. The controller also includes a respiration-parameter module that is configured to output a respiration-data stream that is reflective of one or more respiration-parameter values of one or more respiration parameters associated with ongoing respiration of the user via a respiration device with which the user is operably engaged. The controller also includes a processor that is configured to operably communicate with both the user-interface-communication module and the respiration-device-sensor module and that is further configured to carry out at least the functions that are listed in the preceding paragraph. Yet another embodiment takes the form of a non-transitory CRM having stored thereon instructions executable by a processor for carrying out at least those functions. Still another embodiment takes the form of a system that includes a communication interface, a processor, and data storage containing instructions executable by the processor for carrying out at least those functions.

Numerous other embodiments are described throughout the present disclosure. Indeed, a number of variations and permutations of the above-listed embodiments are described herein. Moreover, it is expressly noted that any variation or permutation that is described in this disclosure can be implemented with respect to any type of embodiment. For example, a variation or permutation that is primarily described in connection with a method embodiment could just as well be implemented in connection with a system embodiment and/or CRM embodiment. Furthermore, this flexibility and cross-applicability of embodiments is present in spite of any slightly different language (e.g., process, method, steps, functions, set of functions, and the like) that is used to describe and/or characterize such embodiments.

BRIEF DESCRIPTION OF THE DRAWINGS

A more detailed understanding may be had from the following description, which is presented by way of example in conjunction with the following drawings, in which like reference numerals are used across the drawings in connection with like elements.

FIG. 13 is a flow chart of operating modules of the illustrative system of FIG. 1, in accordance with at least one embodiment.

Figure 1:
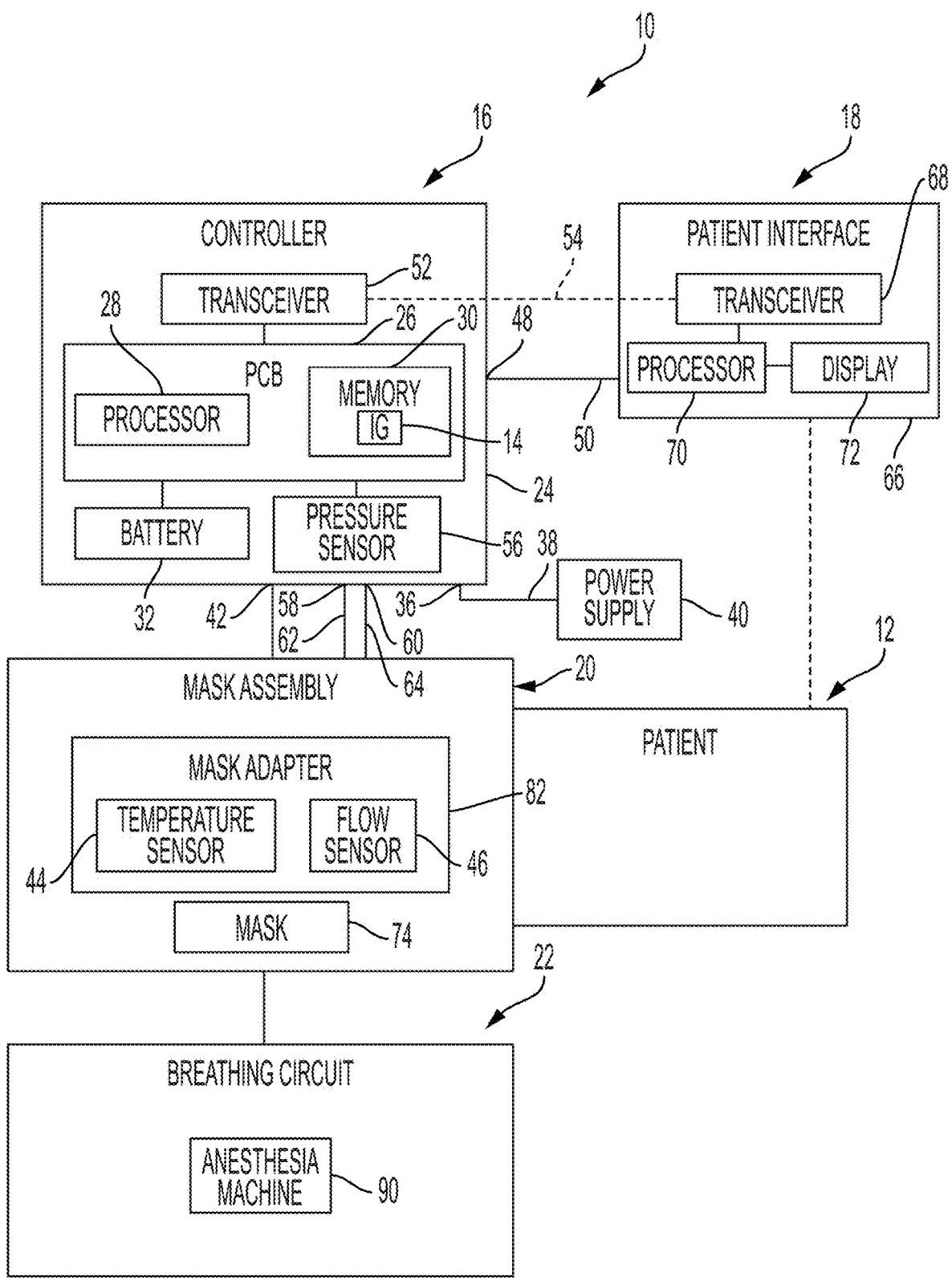
FIG. 1 is a block diagram of illustrative functional components of an illustrative system, in accordance with at least one embodiment.

To promote an understanding of the principles of the present disclosure, reference is made below to the embodiments that are illustrated in the drawings. The embodiments disclosed herein are not intended to be exhaustive or to limit the present disclosure to the precise forms that are disclosed in the following detailed description. Rather, the described embodiments have been selected so that others skilled in the art may utilize their teachings; accordingly, no limitation of the scope of the present disclosure is thereby intended.

In any instances in this disclosure, including in the claims, in which numeric modifiers such as first, second, and third are used in reference to components, data (e.g., values, identifiers, parameters, and/or the like), and/or any other elements, such use of numeric modifiers is not intended to denote or dictate any specific or required order of the so-referenced elements. Rather, any such use of numeric modifiers is intended solely to assist the reader in distinguishing any elements that are referenced in this manner from one another, and should not be interpreted as insisting upon any particular order or carrying any other significance, unless such an order or other significance is clearly and affirmatively explained herein.

Furthermore, in any instances in this disclosure, including in the claims, in which a component of a given device, system, or the like is referred to as a module that carries out (i.e., performs, executes, and/or the like) one or more specified functions, that module includes both hardware and instructions. The hardware could include one or more processors, one or more microprocessors, one or more microcontrollers, one or more microchips, one or more application-specific integrated circuits (ASICs), one or more field programmable gate arrays (FPGAs), and/or one or more devices and/or components of any other type deemed suitable by those of skill in the art for a given implementation. The instructions are executable by the hardware for carrying out the one or more herein-described functions of the module, and could include hardware (i.e., hardwired) instructions, firmware, software, and/or the like, stored in any one or more non-transitory CRMs deemed suitable by those of skill in the art for a given implementation. Each such CRM could be or include memory (e.g., random access memory (RAM), read-only memory (ROM), erasable programmable read-only memory (EPROM), electrically erasable programmable read-only memory (EEPROM a.k.a. $E^2PROM$), flash memory, and/or one or more other types of memory) and/or one or more other types of non-transitory CRM. Any given module could be realized as a single component or be distributed across multiple components as deemed suitable by those of skill in the art.

Moreover, consistent with the fact that the entities and arrangements that are depicted in and described in connection with the drawings are presented as examples and not by way of limitation, any and all statements or other indications as to what a particular drawing "depicts," what a particular element or entity in a particular drawing "is" or "has," and any and all similar statements that are not explicitly self-qualifying by way of a clause such as "In at least one embodiment, . . . ", and that could therefore be read in isolation and out of context as absolute and thus as a limitation on all embodiments, can only properly be read as being constructively qualified by such a clause. It is for reasons akin to brevity and clarity of presentation that this implied qualifying clause is not repeated ad nauseum in the ensuing detailed description.

DETAILED DESCRIPTION OF THE DRAWINGS

While some embodiments described herein are directed to systems for use with anesthesia induction in pediatric patients, it should be appreciated that the present systems and methods are not limited thereto. For example, the systems and methods of the present disclosure may be readily used in connection with other systems where gases are inhaled by either adults or children. Some examples include positive-airway-pressure (PAP) devices such as biphasic PAP (BiPAP) devices and continuous PAP (CPAP) devices, nebulizer devices used for, e.g., treatment of asthma, nitrous gas devices used in, e.g., dental applications, spirometry devices used in, e.g., pulmonary function test (PFT) applications, other respiratory devices used in PFT applications, incentive spirometry devices, and positive expiratory pressure (PEP) devices. Some embodiments of the present systems and methods are applicable in situations in which it is beneficial to train patients to regulate their breathing (e.g., intravenous line insertion, other painful procedures, anxiety reduction, teaching patients how to regulate breathing for medical breathing tests and/or medical exams, meditation exercises, relaxation exercises, and/or the like).

Figure 2:
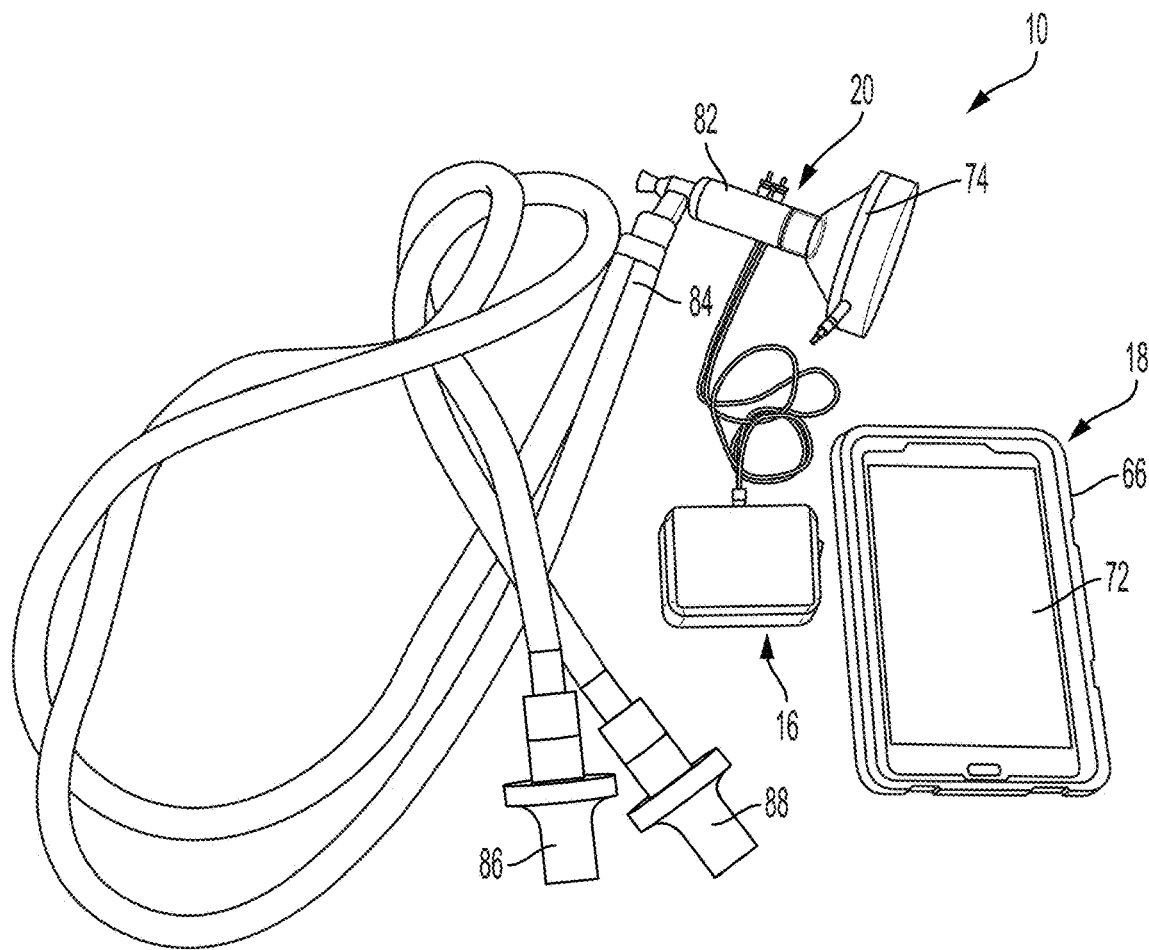
FIG. 2 is a perspective view of the illustrative system of FIG. 1, in accordance with at least one embodiment.
Figure 3:
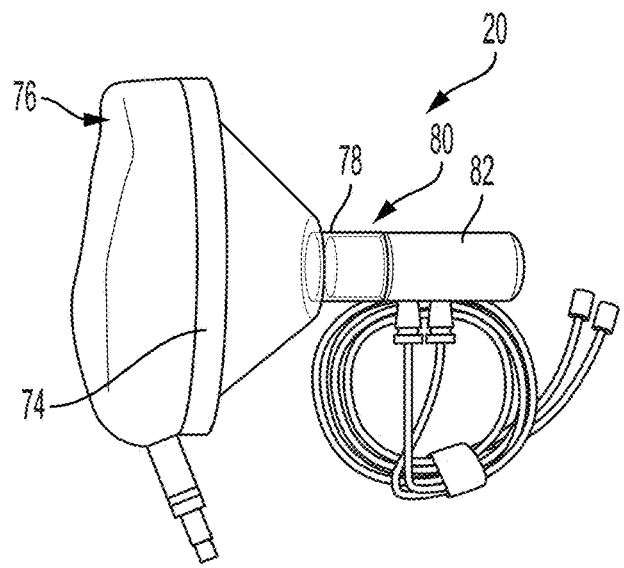
FIG. 3 is a perspective view of a mask, including a sensor adapter and pressure sensor tubes, of the illustrative system of FIG. 1, in accordance with at least one embodiment.
Figure 4:
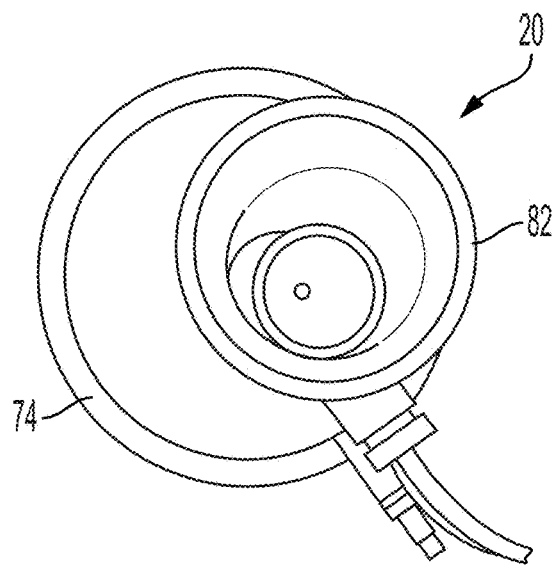
FIG. 4 is a perspective view of the distal end of the illustrative sensor adapter of FIG. 3, in accordance with at least one embodiment.

Referring initially to FIGS. 1-3, an illustrative respiratory feedback system 10 of the present disclosure is configured to receive breathing information from a patient 12 and then provide breathing feedback to the patient 12, illustratively through interactive media, such as an interactive game 14 within a controller 16 and accessed by the patient 12 via a user or patient interface 18. The controller 16 is in communication with the patient interface 18 and with a mask assembly 20. The mask assembly 20 is configured to be worn by the patient 12 and operably coupled to a breathing system or circuit 22.

The controller 16 illustratively includes a housing 24 receiving a support, such as a printed circuit board 26. A processor 28 and a memory 30 are illustratively supported by the printed circuit board 26. Software, including machine readable instructions defining the interactive game 14, is illustratively stored within the memory 30 and configured to be executed by the processor 28.

Figure 5:
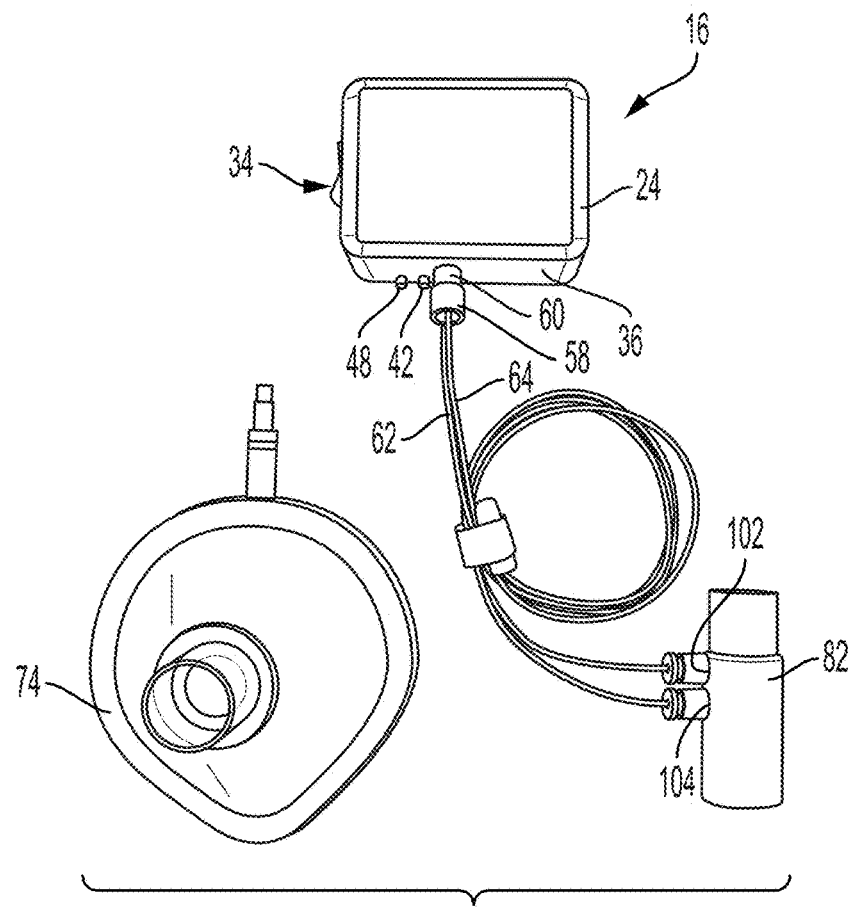
FIG. 5 is a perspective view of the mask and the sensor adapter of FIG. 4, interfacing with the controller of the illustrative system of FIG. 1 via the pressure sensor tubes, in accordance with at least one embodiment.

With reference to FIGS. 1 and 5, a rechargeable battery 32 is illustratively supported within the controller housing 24 and is in electrical communication with the printed circuit board 26. Illustratively, a master power switch 34 is supported by the controller housing 24 (FIG. 5), and an electrical communication port 36 (e.g., a USB micro port) is illustratively provided to receive a cable 38 for power charging from an external power supply 40, and/or communication with an external processor (not shown) for programming. Additional electrical communication ports may be supported by the controller housing 24 to receive input to, and/or provide output from, the processor 28. For example, a first port 42 may receive signal input from a gas parameter sensor (e.g., a temperature sensor 44 and/or a flow sensor 46), and a second port 48 may provide signal output to an external device (e.g., the patient interface 18). A USB cable 50 may provide communication between the processor 28, via the second port 48, and the patient interface 18.

The illustrative controller 16 may further include a transceiver 52 in electrical communication with the processor 28, and is in wireless communication with the patient interface 18 to define a wireless communication link 54. Illustratively, the transceiver 52 is a wireless Bluetooth transceiver that may be integrated with the processor 28. In one illustrative embodiment, the combined processor 28 and transceiver 52 is an integrated circuit, such as Part No. NRF51822-QFAB-R7 available from Nordic Semiconductor ASA of Oslo, Norway.

A differential pressure sensor 56 is illustratively received within the housing 24 and is in electrical communication with the processor 28. With reference to FIGS. 1, 5, 8 and 9, differential pressure input ports 58 and 60 in the housing 24 provide fluid communication between the mask assembly 20 and the pressure sensor 56 via sensing tubes 62 and 64. The pressure sensor 56 may comprise a dual port pressure sensor, such as Part No. MPXV7002DPT1 available from NXP USA, Inc. of the Netherlands.

As noted above, the patient interface 18 is illustratively in communication with the controller 16. With reference to FIGS. 1 and 2, the patient interface 18 may comprise a portable electronic device, such as a smartphone, a tablet or a laptop computer. The patient interface 18 illustratively includes an outer housing 66 receiving a transceiver 68, such as a Bluetooth transceiver, in wireless communication with the Bluetooth transceiver 52 of the controller 16. A processor 70 is in communication with the transceiver 68 and with a display 72 to display graphics and other information from the processor 70. The display 72 may be a touch screen to receive input from the patient and transmit such information to the controller 16 via the wireless communication link 54. In other illustrative embodiments, a keyboard (not shown) may be supported by the outer housing 66 in spaced relation to the display 72.

With reference to FIGS. 3-7, the mask assembly 20 illustratively includes a conventional mask 74, such as an anesthesia face mask configured to cover a least a portion of the oronasal region of the patient 12. More particularly, the illustrative mask 74 includes a proximal end 76 configured to be sealably worn over a nose and/or mouth of the patient 12. A gas port or opening 78 is defined by the distal end 80 of the mask 74. A mask adapter 82, illustratively a spirometer tube, is positioned intermediate the mask 74 and a branch connector 84 (FIG. 2). Illustratively, the processor 28 uses properties of the spirometer tube 82 and gas pressure measured by the pressure sensor 56 to detect direction, velocity and volume of gas. The branch connector 84 is fluidly coupled to an inlet (i.e., inspiration) tube 86 and an outlet (i.e., expiration) tube 88 which, in turn, are coupled to the breathing circuit 22. The breathing circuit 22 illustratively includes a conventional anesthesia machine 90 fluidly coupled to the distal ends of the tubes 86 and 88. Illustrative anesthesia machines 90 include, for example, the CareStation 600 Series, the Aisys CS2, the Avance CS2 with ecoFlow, and the Aespire, all of which are available from GE Healthcare of Chicago, IL.

Figure 6:
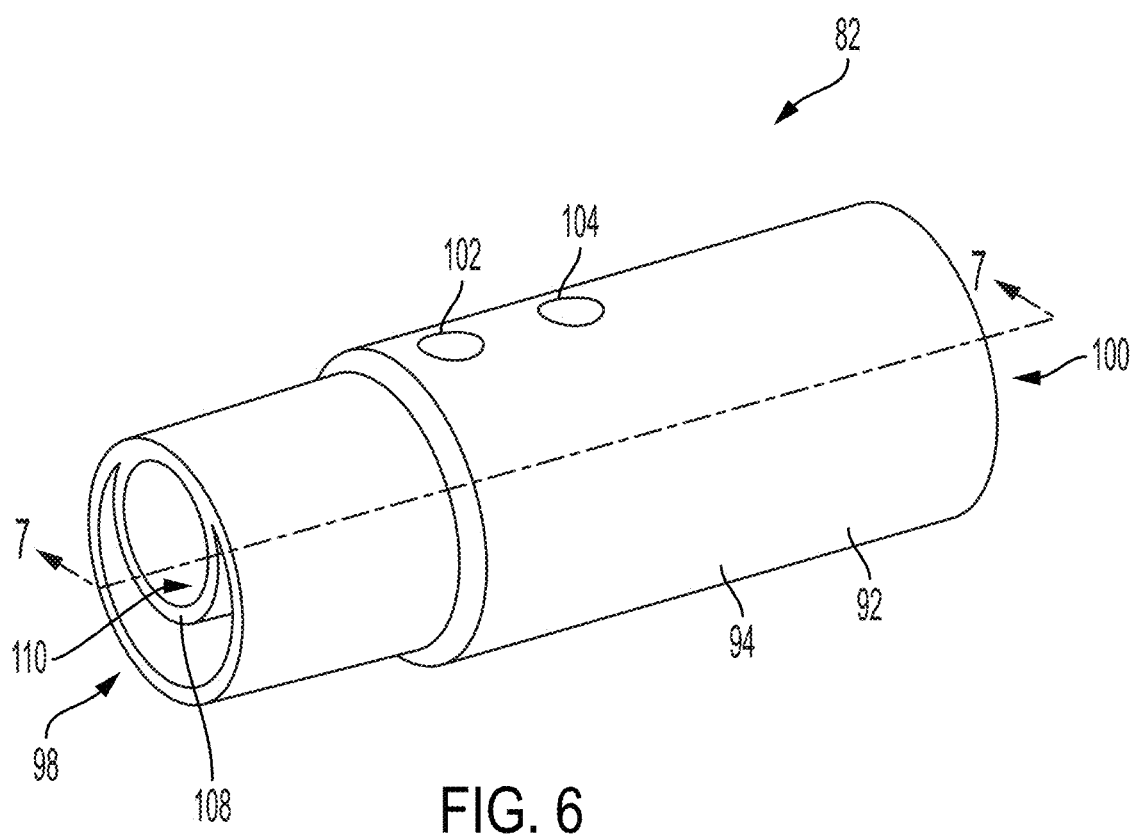
FIG. 6 is a perspective view of the sensor adapter of FIG. 4, in accordance with at least one embodiment.
Figure 7:
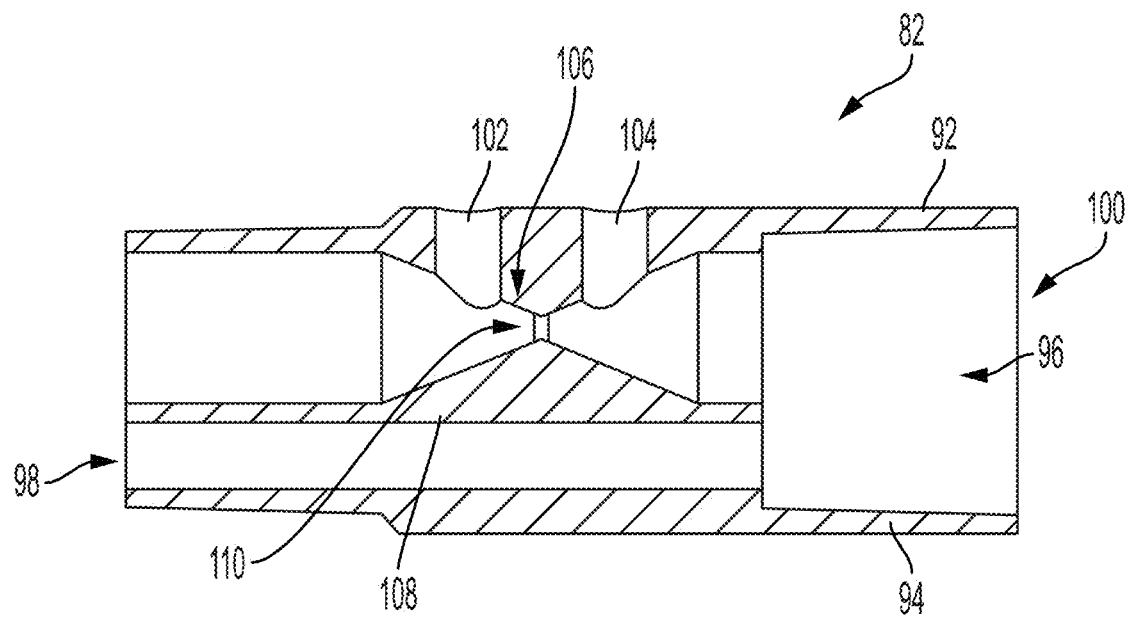
FIG. 7 is a cross-sectional view of the sensor adapter, taken along line 7-7 of FIG. 6, in accordance with at least one embodiment.

With reference to FIGS. 5-7, the controller 16 is configured to receive data regarding at least one parameter (e.g., pressure, temperature, flow rate, carbon dioxide, etc.) of gas flowing through the mask adapter 82. Illustratively, the mask adapter 82 includes a cylindrical housing 92 having an outer wall 94 defining a central or main passageway 96 extending between a proximal opening 98 and a distal opening 100. The proximal opening 98 of the mask adapter 82 is fluidly coupled to the mask 74, and the distal opening 100 of the mask adapter 82 is coupled to the branch connector 84. First and second pressure sensing ports 102 and 104 extend radially within the outer wall 94 and are fluidly coupled to the sensing tubes 62 and 64, respectively. As such, the tubes 62 and 64 are in fluid communication with the differential pressure sensor 56. A restriction 106 is illustratively received within the outer wall 94 and may comprise an inner wall 108 defining a reduced flow passageway 110 intermediate the first and second pressure sensing ports 102 and 104. In other illustrative embodiments, the mask adapter 82 may be similar to those shown in U.S. Pat. No. 5,398,695 to Anderson et al., and U.S. Pat. No. 8,333,111 to Hietala, the disclosures of which are expressly incorporated herein by reference.

Figure 10:
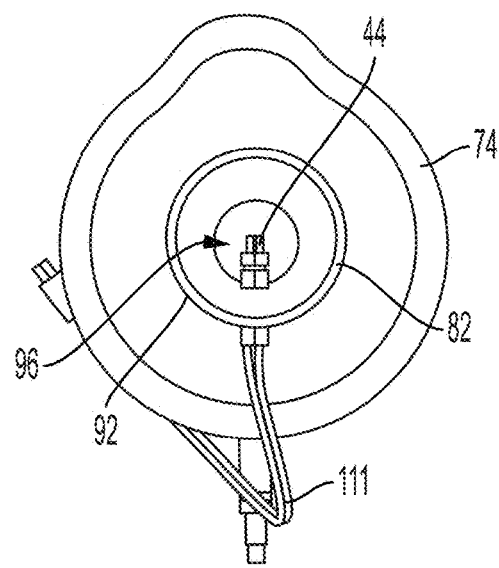
FIG. 10 is a perspective view of the distal end of an illustrative sensor adapter supporting an illustrative temperature sensor, in accordance with at least one embodiment.
Figure 11:
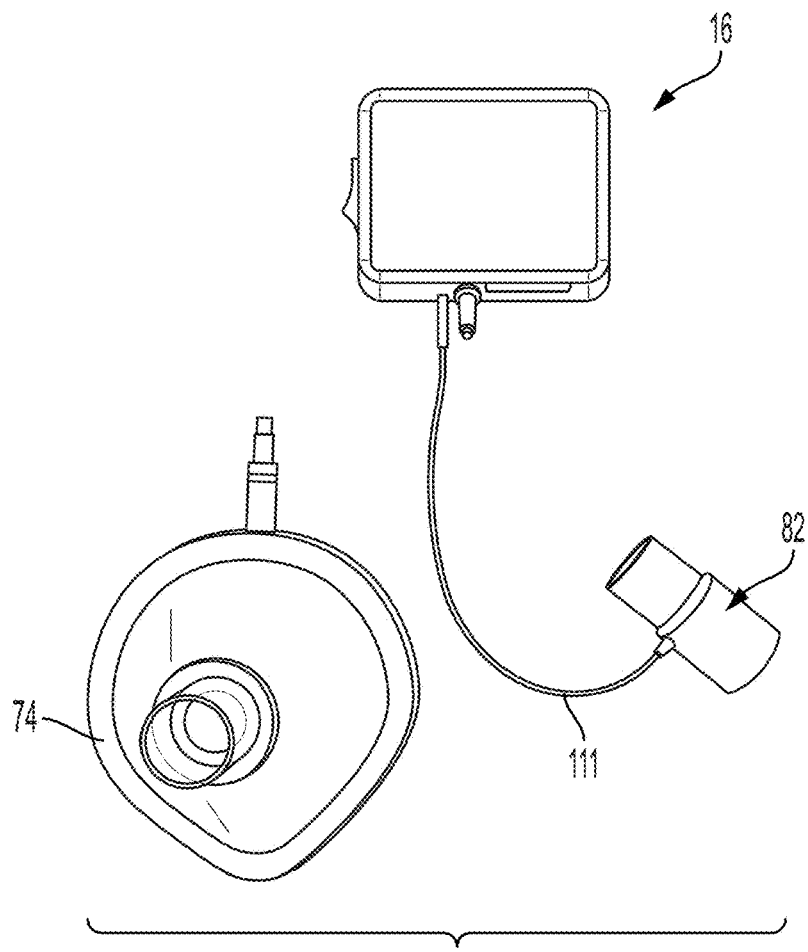
FIG. 11 is perspective view of the mask, the sensor adapter, and the temperature sensor of FIG. 10, interfacing with the controller of the illustrative system of FIG. 1, in accordance with at least one embodiment.

As shown in the illustrative embodiment of FIGS. 10 and 11, temperature sensor 44 may be substituted for, or used in addition to the differential pressure sensor 56. Illustratively, the temperature sensor 44 may be supported by the mask adapter housing 92 and received within the passageway 96. The temperature sensor 44 may provide signals to the controller 16 via a cable 111. An illustrative temperature sensor 44 may be a negative temperature coefficient (NTC) thermistor, such as Part No. 445-2550-2-ND available from TDK Corporation of Uniondale, New York, USA.

Alternatively, as shown in FIG. 1, flow sensor 46 may be substituted for, or used in addition to the differential pressure sensor 56 and/or the temperature sensor 44. Illustratively, the flow sensor 46 may be supported by the mask adapter housing 92 and received within the passageway 96. While the sensors 44 and 46 may be supported by the mask adapter housing 92, they may also be supported at remote locations, such as within the controller housing 24.

Figure 12:
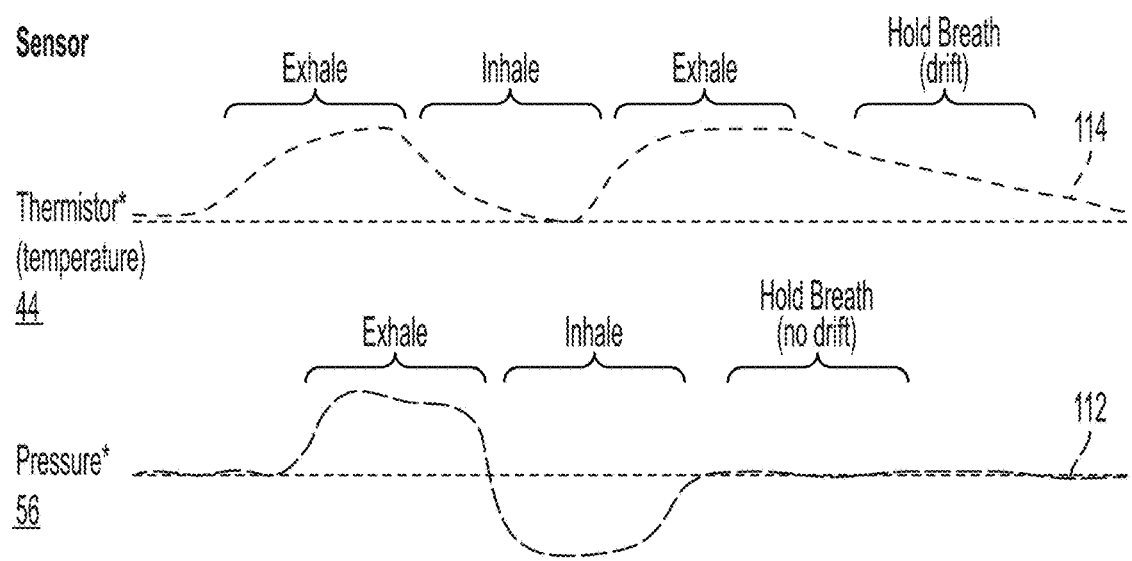
FIG. 12 is an illustrative graph of illustrative sensor inputs to the controller of the illustrative system of FIG. 1, in accordance with at least one embodiment.

FIG. 12 is a graph of illustrative inputs from the sensors 44 and 56 to the processor 28 of the illustrative system 10 of FIG. 1. The lower portion of the graph illustrates representative input 112 from the pressure sensor 56, showing how differential pressure directly corresponds to air flow, with no drift or environmental dependency. The upper portion of the graph illustrates representative input 114 from the temperature sensor 44, showing how temperature variations correspond to air flow.

While the illustrative system 10 uses detected parameters from gas within the mask adapter 82 in connection with the interactive game 14, it should be appreciated that alternative inputs may be substituted therefor. In an alternative illustrative embodiment, an external sensor (not shown) may be directly attached to the mask 74. More particularly, a small reusable wireless sensor, such as a contact microphone, may be secured to the mask 74 to sense audio vibrations through contact with the mask 74. In another alternative illustrative embodiment, the mask 74 may include a small sensor pad or port (not shown) formed into the mask 74 to accommodate the small reusable sensor, such as a contact microphone. The sensor pad or port is configured to improve sensor sensitivity.

Figure 13:
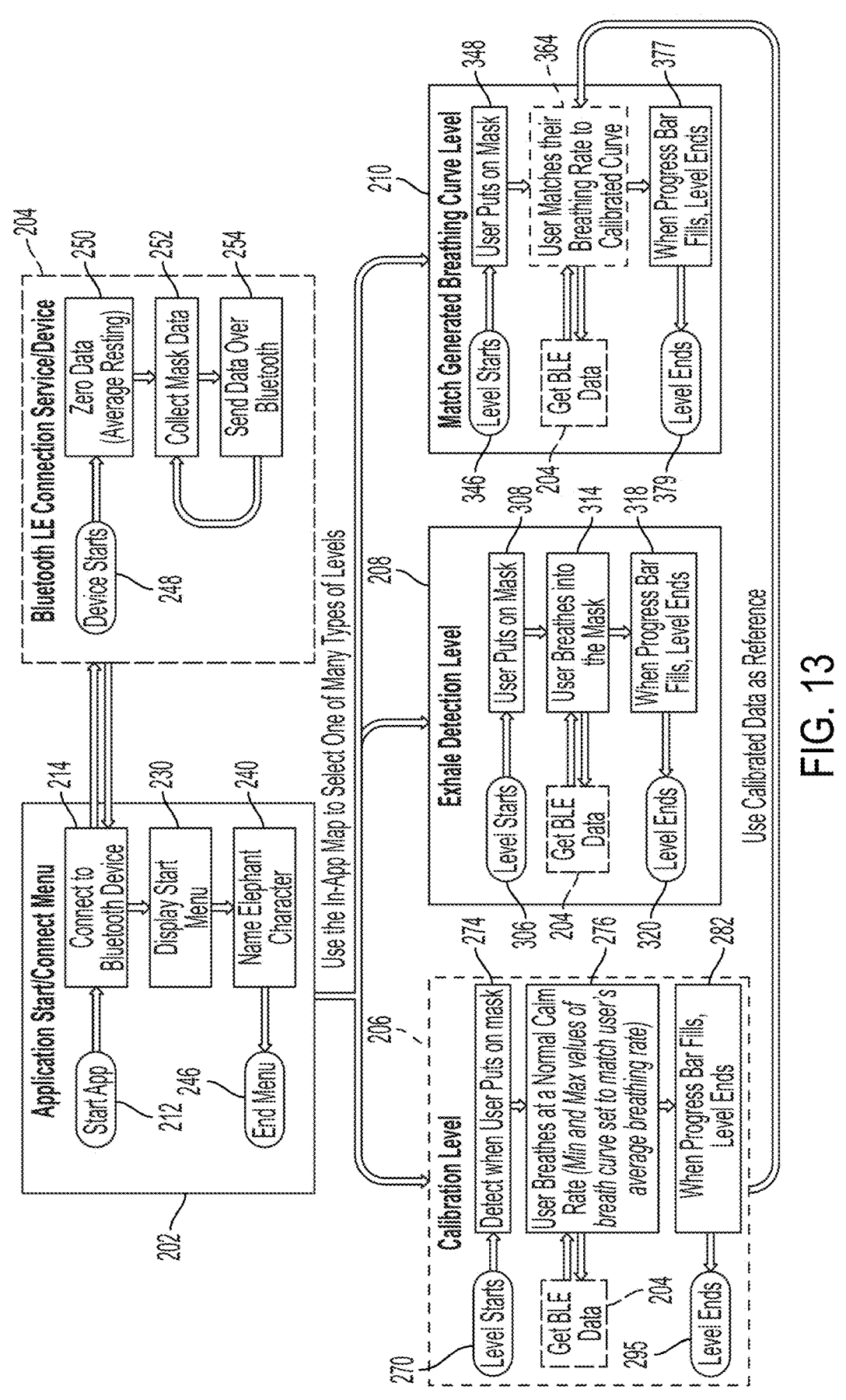

As noted above, the controller 16 cooperates with the mask assembly 20 and the patient interface 18 to provide interactive media to the patient 12. More particularly, the processor 28 executes software stored in the memory 30 to provide interactive media, illustratively interactive game 14, on the display 72 of the patient interface 18 which is responsive to the detected gas parameters (e.g., from the pressure sensor 56, the temperature sensor 44, and/or the flow sensor 46). With reference to FIG. 13, the interactive game 14 illustratively includes an initialization module or subroutine 202 (e.g., an application start/connect menu), a data collection module or subroutine 204 (e.g., a Bluetooth low energy (LE) connection service/device module), a calibration module 206 (e.g., a calibration level), an exhale detection module or subroutine 208 (e.g., an exhale detection level), and an induction module or subroutine 210 (e.g., a match generated breathing curve level).

Figure 8:
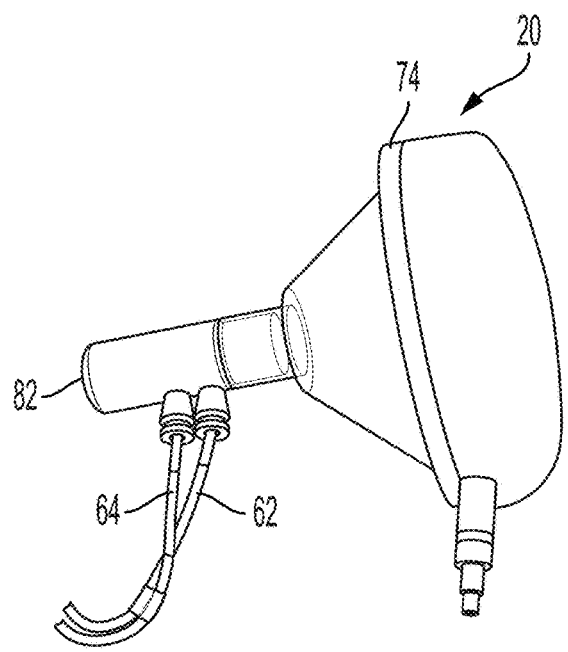
FIG. 8 is a perspective view of the illustrative mask and the sensor adapter of FIG. 4, including color-coded pressure sensor tubes, in accordance with at least one embodiment.
Figure 9:
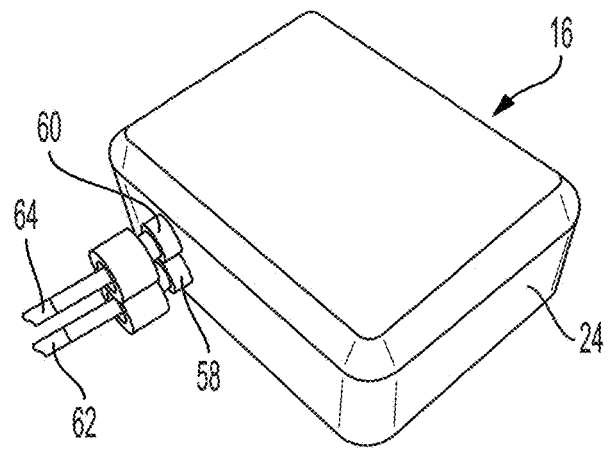
FIG. 9 is a perspective view of the illustrative controller of FIG. 4, in accordance with at least one embodiment.

Illustrative operation of the respiratory feedback system 10 is detailed below with reference to FIGS. 13-28C. During preliminary set-up, the mask adapter 82 is inserted into the opening 78 of the mask 74 until it is snug against the mask 74. The proximal ends of the pressure sensing tubes 62 and 64 are then coupled to the fluid ports 102 and 104 in the mask adapter 82, and the distal ends of the pressure sensing tubes 62 and 64 are then coupled to the fluid ports 58 and 60 in the controller housing 24. The opposing proximal and distal ends of the sensing tubes 62 and 64 may be color coded to facilitate proper orientation of the tubes 62 and 64 relative to the respective ports 102, 104 and 58, 60 of the mask adapter 82 and the controller housing 24 (FIGS. 8 and 9).

With reference to FIG. 13, the illustrative method begins with operation of the initialization module 202 at block 212, where the controller 16 and the patient interface 18 are turned on by a caregiver. More particularly, the power switch 34 on the controller housing 24 is turned to an on position (FIG. 5). The power cable 38 may be inserted into the power port 36 on the controller housing 24 to charge the battery 32 (FIG. 9).

Figure 14A:
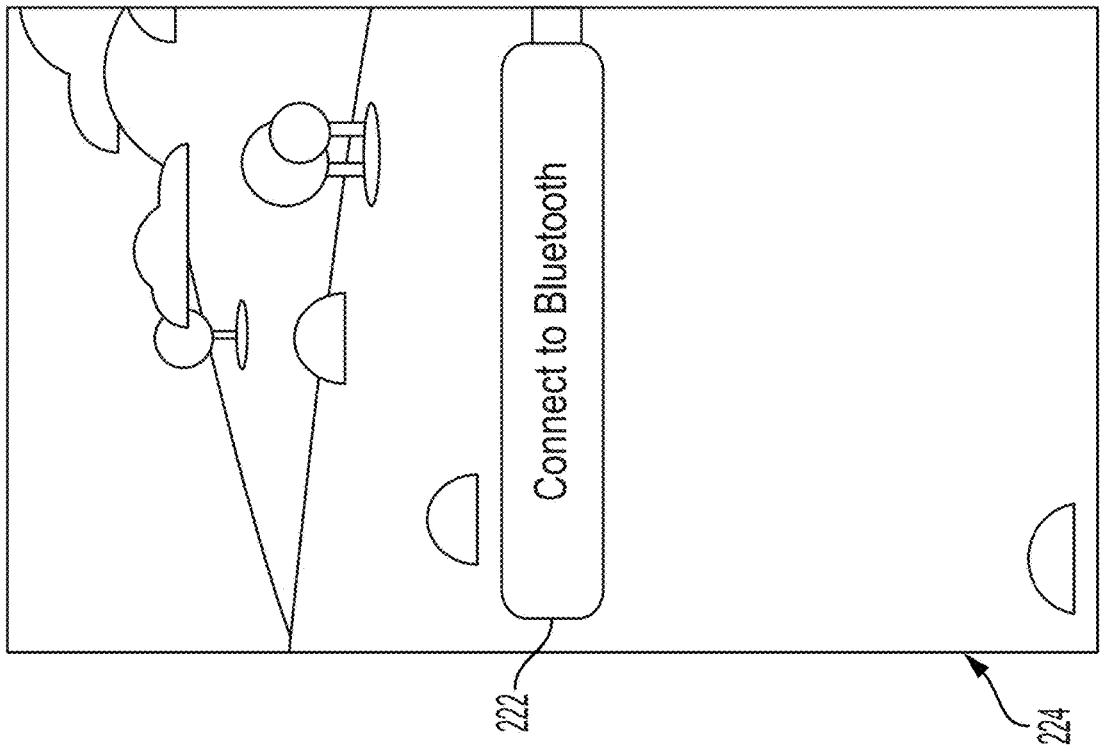
FIG. 14A is an illustrative scan screen, in accordance with at least one embodiment.

With reference to FIGS. 13 and 14A, at block 214 the patient interface 18 scans for available wireless signals to which the transceiver 68 can connect. More particularly, the patient 12 or caregiver can select the signal emitted from the transceiver 52 of the controller 16 from a list of available signals 216 detected and shown on a scan display screen 218. A stop scan button 219 may be touched to stop the search for available wireless signals.

Figure 14B:
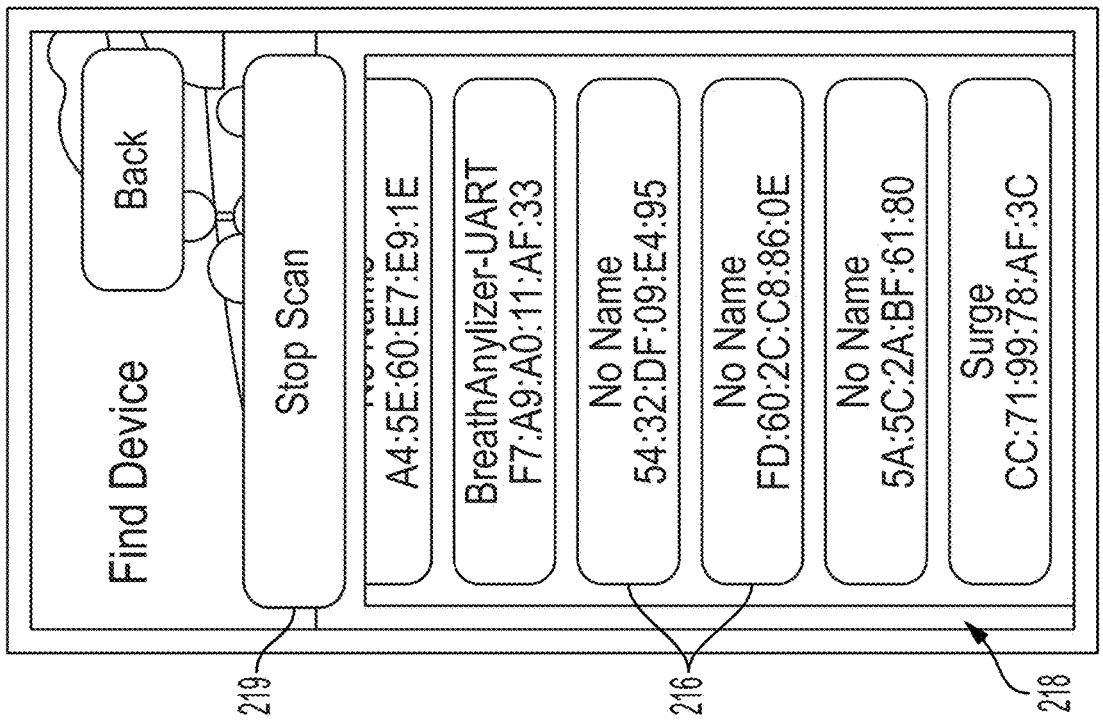
FIG. 14B is an illustrative connect screen, in accordance with at least one embodiment.

The illustrative method continues at block 214 of FIG. 13, where the patient interface 18 connects to the controller 16. As shown in FIG. 14B, the user can touch a "Connect to Bluetooth" button 222 on a connect display screen 224 to wirelessly connect the transceiver 68 of the patient interface 18 with the transceiver 52 of the controller 16. Next, an illustrative play screen 226 (FIG. 15A) appears on the patient interface 18, where the patient 12 or the caregiver may touch the "Play" button 228 to initiate the interactive game 14. A disconnect button 229 on screen 224 may be touched to disconnect the patient interface 18 from the controller 16.

Figure 15B:
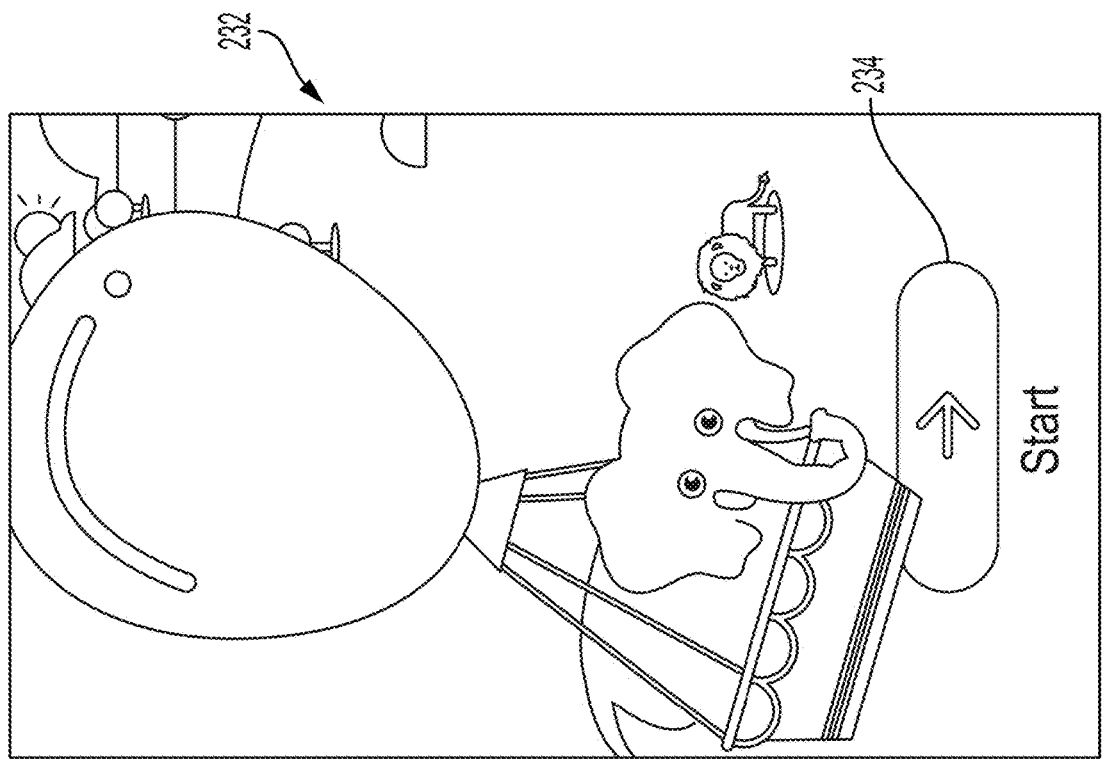
FIG. 15B is an illustrative start screen, in accordance with at least one embodiment.
Figure 15A:
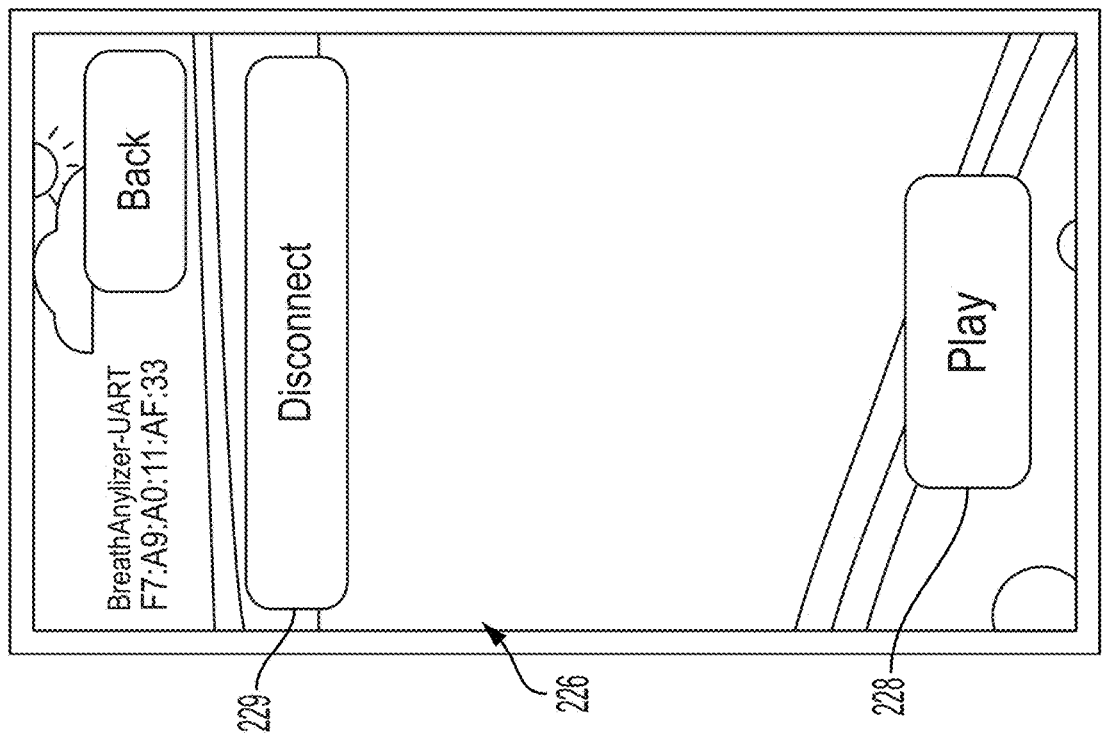
FIG. 15A is an illustrative initial play screen, in accordance with at least one embodiment.
Figure 15C:
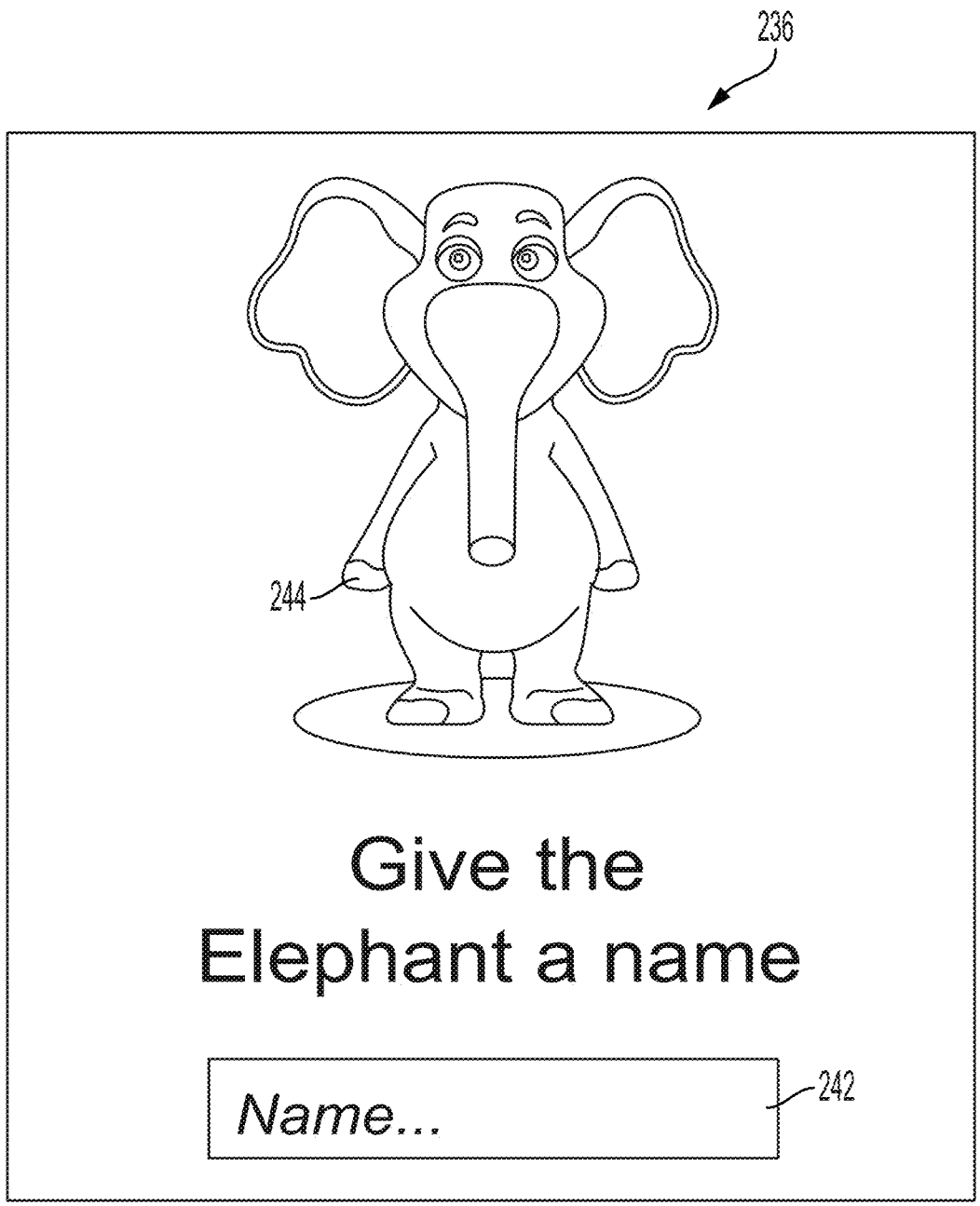
FIG. 15C is an illustrative character-naming screen, in accordance with at least one embodiment.

At block 230 of FIG. 13, the start menu screen 232 is shown on the display 72 (FIG. 15B). By touching the "Start" button 234, the game 14 progresses to the screen 236 of FIG. 15C, where the patient can name her character at block 240 (FIG. 13) by entering a name in a window 242. In certain illustrative embodiments, the patient 12 is provided with an option to select from a list of different characters (e.g., animals, superheroes, etc.). In the illustrative embodiment, the character is an elephant 244. The initialization module 202 ends at block 246 of FIG. 13.

With reference to the data collection module 204 of FIG. 13, the patient 12 holds the mask assembly 20 by the mask 74 or the mask adapter 82 (FIG. 3). With further reference to FIG. 13, the method continues at block 248. At block 250, the data (e.g., variables used by the processor 28) is initialized to an average resting value. At block 252, mask data is collected through a parameter sensor, such as the differential pressure sensor 56. More particularly, in the illustrative embodiment, gas pressure data from within the mask adapter 82 is detected by the pressure sensor 56 and supplied to the processor 28. At block 254, this gas pressure data is transmitted over the wireless link 54 from the controller 16 to the patient interface 18. This gas pressure data may also be stored in the memory 30. During operation, the data collection module 204 is illustratively accessed by the calibration module 206, the exhale detection module 208 and the induction module 210, as further detailed below.

Figure 16B:
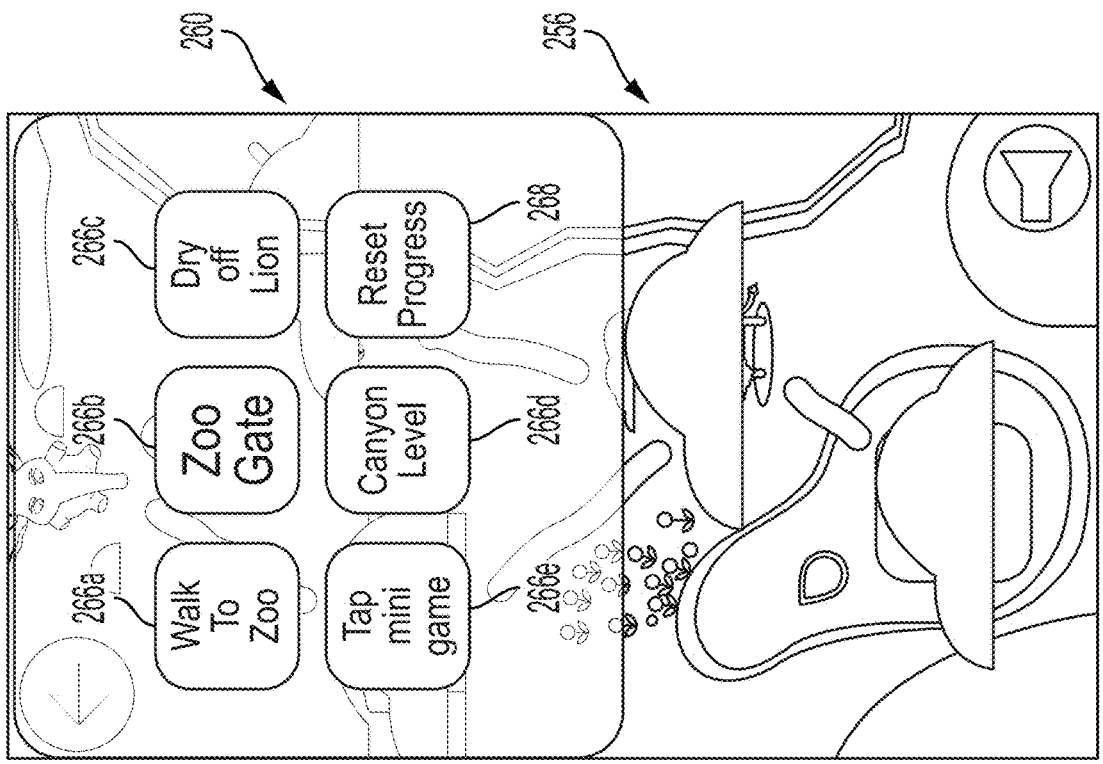
FIG. 16B is the illustrative sequential-phase-map screen of FIG. 16A, including a dropdown menu of selectable interactive game components, in accordance with at least one embodiment.
Figure 16A:
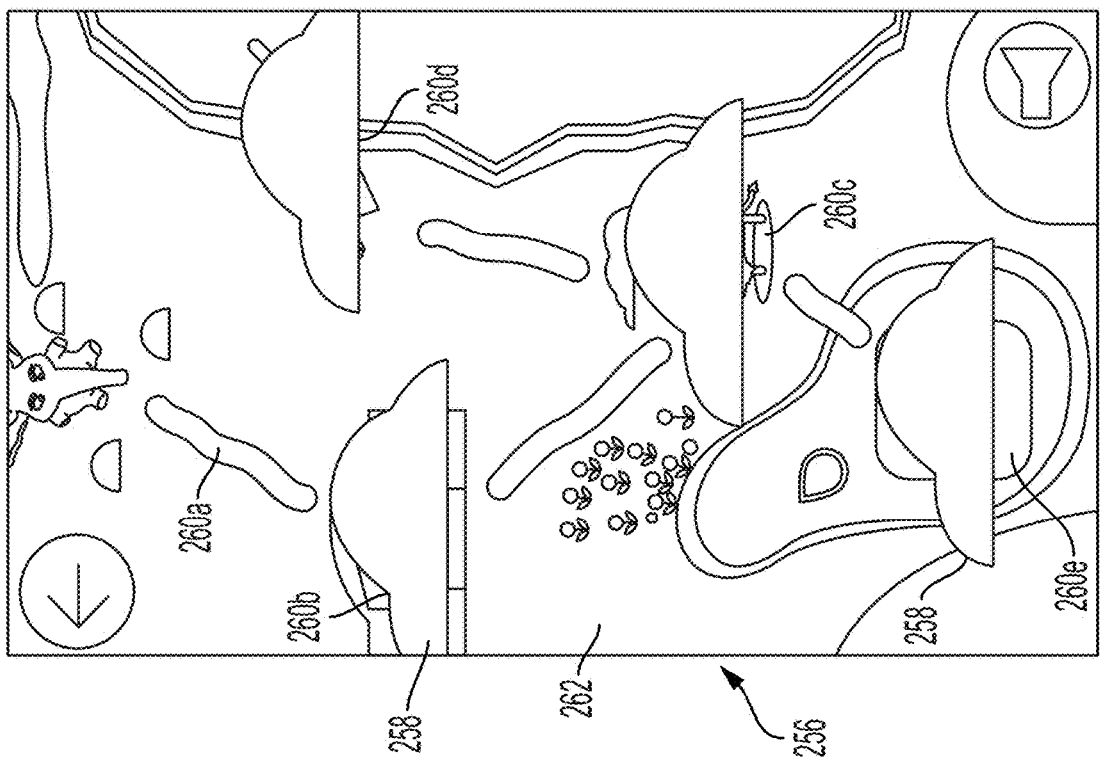
FIG. 16A is an illustrative sequential-phase-map screen, depicting an illustrative character in an initial position, in accordance with at least one embodiment.

The illustrative method continues with operation of one of the calibration module 206, the exhale detection module 208 and/or the induction module 210 of FIG. 13. A main menu screen 256 is shown in FIG. 16A as including clouds 258 covering individual game components or levels 260 yet to be played on a map 262. A patient 12 will return to the map 262 upon completion of each game component 260. To begin the next game component 260, a patient 12 taps on the game component 260 that is no longer covered by a cloud 258. If a patient 12 wishes to skip to a particular game component 260, she may use one finger to swipe down from the top of the screen 256 and a list of the game components 260 will appear as shown in FIG. 16B. By tapping on a button 266 associated with the desired game component 260, it will begin playing. Illustrative game components include a first, or "Walk to Zoo" game component 260a (associated with button 266a); a second, or "Zoo Gate" game component 260b (associated with button 266b); a third, or "Dry off Lion" game component 260c (associated with button 266c); a fourth, or "Canyon Level" game component 260d (associated with button 266d); and a fifth, or "Tap mini game" game component 260e (associated with button 266e). A "Reset Progress" button 268 may be tapped by the patient 12 to restart a selected game component 260.

Figures 17, 18:
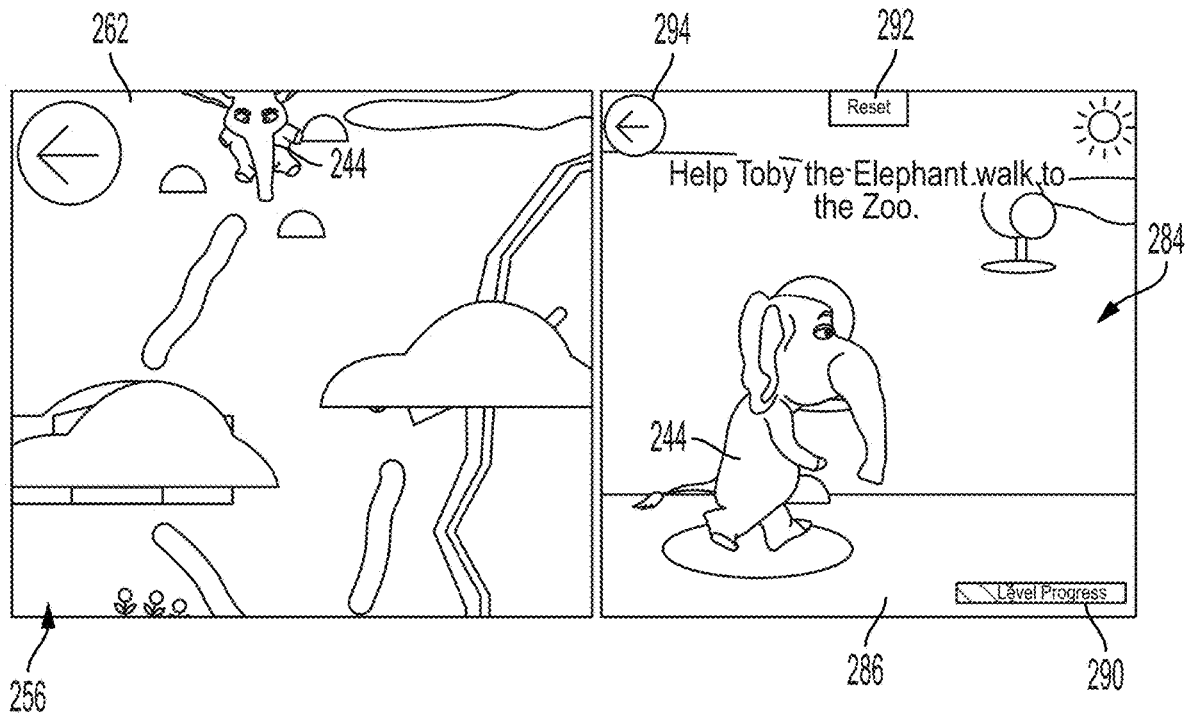
FIG. 17 is the illustrative automatic-calibration-mode screen, in accordance with at least one embodiment.
FIG. 18 is an illustrative walking-component screen of an automatic calibration mode, in accordance with at least one embodiment.

Returning to FIG. 13, the calibration module 206 of the illustrative method begins at block 270. The calibration module 206 is illustratively executed in a pre-operative or baseline phase. FIG. 17 shows an enlarged portion of the illustrative main menu screen 256 upon entering the automatic calibration mode. At block 274, the controller 16 detects when the patient 12 places the mask 74 over her mouth and/or nose by detecting air flow (inhaling and/or exhaling) via the pressure sensor 56. At block 276, the patient 12 breaths at a normal calm rate by playing an interactive game component 260 facilitating baseline establishment, illustratively the "Walk to Zoo" or walking game component 260a. FIG. 18 illustrates the interactive game display screen 278 upon entering the walking game component 260a. During the interactive game 260a, data is transmitted between the controller 16 and the patient interface 18 at block 280 (i.e., via the data collection module 204).

With further reference to FIG. 13, while the patient 12 breaths at a normal calm rate at block 276, she taps on the elephant 244 in the map 262 on screen 256 to initiate the first game component 260a. Screen 284 appears on the display 72, where the elephant 244 walks down a path 286 over a predetermined duration (illustratively, a 30 second duration). The illustrative screen 284 of FIG. 18 includes a progress bar 290 in the lower right corner. When the progress bar 290 fills up, the game component 260a has been completed as indicated by block 282 in FIG. 13. Touching a reset button 292 at the top of the screen 284 will reset the current game component 258. Tapping an arrow 294 in the top left of the screen 288, will illustratively return the patient 12 back to the main menu screen 256 of FIG. 16A.

The illustrative purpose of the walking game component 260a is to collect the user's data for calibration (e.g., so a normal breath line can be generated) in the induction module 210, as further detailed below. The average time to complete the walking game component 260a is approximately 30 seconds. The game component 260a may be restarted anytime by touching the "Reset Progress" button 268 (FIG. 16B), for example, if it is believed that inaccurate data has been acquired. Operation of the calibration module 206 illustratively ends at block 295 of FIG. 13.

Illustratively, there are two components of the interactive game 14 that may require adjustment. In an illustrative embodiment, the sensitivity of the interactive game 14 (which can be manually adjusted) does not automatically adjust. However, in this illustrative embodiment, the calibrated curve may be automatically adjusted (but cannot be manually adjusted). In alternative embodiments, both the sensitivity and the calibrated curve may have both an automatic adjustment option and a manual adjustment option.

Figures 19A, 19B, 19C:
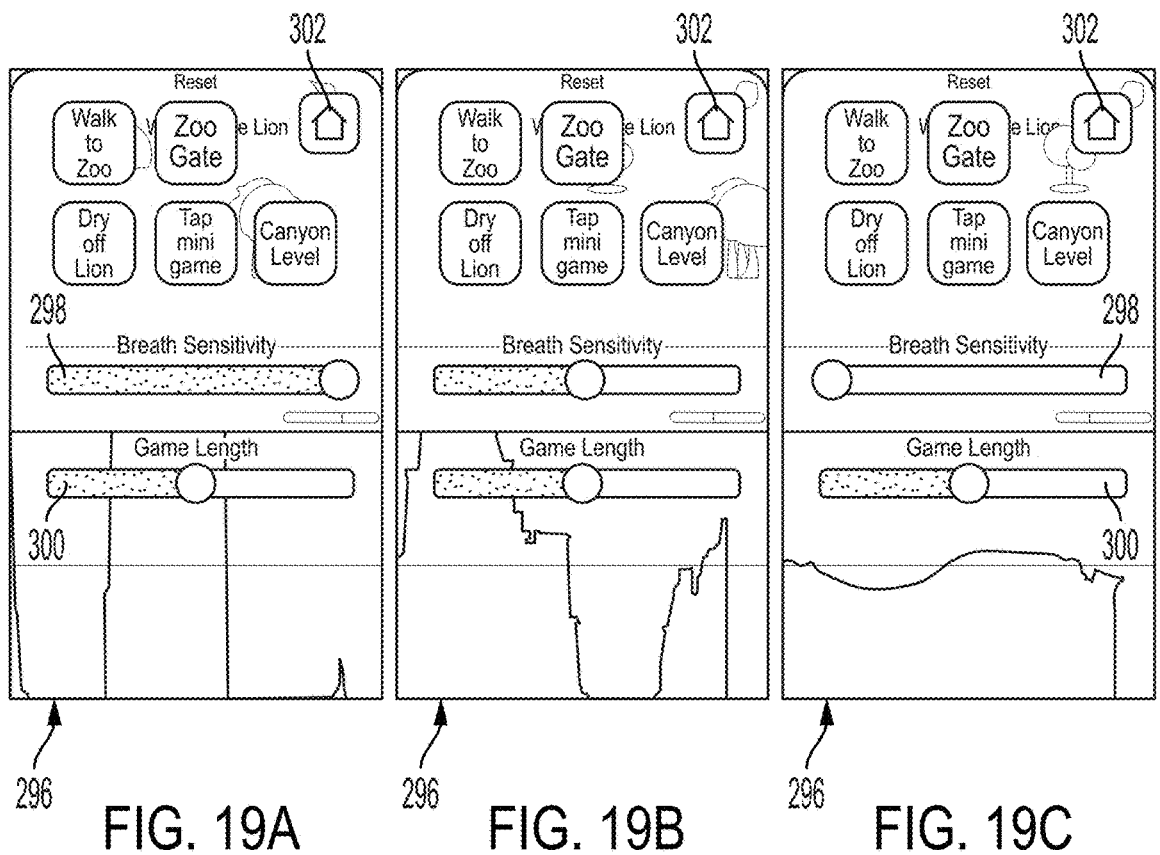
FIG. 19A is an illustrative manual-calibration-mode screen, showing a maximum breath sensitivity selected, in accordance with at least one embodiment.
FIG. 19B is the illustrative manual-calibration-mode screen of FIG. 19A, showing a moderate breath sensitivity selected, in accordance with at least one embodiment.
FIG. 19C is the illustrative manual-calibration-mode screen of FIG. 19A, showing a minimum breath sensitivity selected, in accordance with at least one embodiment.

More particularly, while the walking game component 260a may be configured to provide automatic calibration based upon baseline breathing input determined via the mask assembly 20, such calibration may also be manually adjusted. FIGS. 19A-19C show an illustrative manual configuration screen 296 of the patient interface 18. The configuration screen 296 illustratively includes a breath sensitivity slide bar 298 for adjusting breath sensitivity, and a game length slide bar 300 for adjusting the duration of the game 14. A home icon button 302 may be touched to return to the home menu screen of FIG. 16A. FIG. 19A shows a maximum breath sensitivity selected by the slide bar 298, FIG. 19B shows a moderate breath sensitivity selected by the slide bar 298, and FIG. 19C shows a minimum breath sensitivity selected by the slide bar 298.

Illustratively, automatic adjustment may be based upon the first interaction of the patient 12 with the mask assembly 20. It may be set at the highest sensitivity initially (so any age will be recognized), then adjust appropriately as a baseline is established, so that subsequent games 260 won't be too hard or too easy for the patient 12. This would be based on volume of breath (tidal volume for small children will almost always be less than older children), but there is some variation among children of the same age.

Returning to FIG. 13, operation of the exhale detection module 208 of the illustrative method begins at block 306. The second and third game components 260b and 260c may be executed as part of the exhale detection module 208 and/or the match generated breathing curve module 210. The exhale detection module 208 is illustratively executed in a pre-operative phase. As further detailed herein, the third game component 260c may comprise the match generated breathing curve level or function. Illustratively, the baseline for the third game component 260c is generated from the first game component 260a. In certain illustrative embodiments, the second game component 260b may provide input to the baseline for the third game component 260c. In other illustrative embodiments, the first game component 260a, the second game component 260b and/or the third game component 260c may establish a baseline breathing curve (or calibrated parameters based upon baseline rate and/or depth of breathing) for the fourth game component 260d. If an adequate baseline is not obtained, then the breathing curve (or parameters) may be calibrated to normal parameters for the age and/or size of the patient 12.

Figures 20, 21:
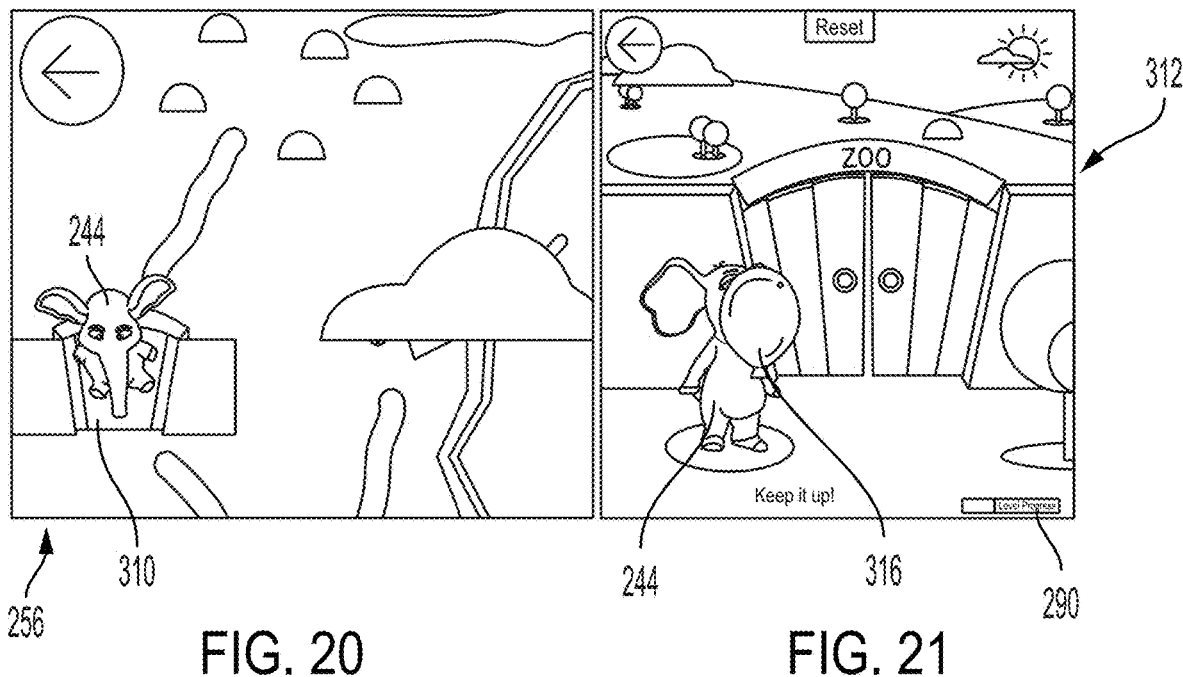
FIG. 20 is the illustrative sequential-phase-map screen of FIG. 16A, depicting the illustrative character having traversed to and about to enter an illustrative balloon-blow-up game component of an illustrative exhalation-validation phase, in accordance with at least one embodiment.
FIG. 21 is an illustrative initial screen of the illustrative balloon-blow-up game component of the illustrative exhalation-validation phase, in accordance with at least one embodiment.

FIG. 20 shows the illustrative main menu screen 256 upon initiating the exhale detection module 208. At block 308, the controller 16 detects when the patient 12 places the mask 74 over her mouth and/or nose by detecting air flow (inhaling and/or exhaling) via the pressure sensor 56.

The second game component 260b illustratively comprises a Zoo Gate or Balloon Blow-up game component. The illustrative purpose of the second game component 260b is to familiarize the patient 12 with using the mask assembly 20 and teach slow, deep breathing. The average time to complete this game component 260b is illustratively between 30 to 60 seconds.

With further reference to the illustrative main menu screen 256 of FIG. 20, the patient 12 taps on zoo doors or gates 310 that are now uncovered by the cloud 258. In response, the elephant 244 will walk to the zoo as shown in the screen 312 of FIG. 21. Tapping on the elephant 244 again will start the second game component 260b. The goal of the second game component 260b is to exhale into the mask 74 as indicated by block 314 of FIG. 13. This will "fill" the balloon 316 shown in the screen 312 of FIG. 21. When the progress bar 290 is completely filled, the gates 310 open and the elephant 244 goes into the zoo, as indicated by block 318 of FIG. 13. Operation of the exhale detection module 208 ends at block 320 of FIG. 13.

In an illustrative embodiment, operation of the exhale detection module 208 continues by returning to block 306 of FIG. 13 to begin the third game component 260c. The third game component 260c illustratively comprises the Dry off the Lion or drying game component. The illustrative purpose of the third game component 260c is to help the patient 12 understand the rate at which she should breathe. More particularly, the third game component 260c detects inhalation/exhalation and is calibrated based upon the first (i.e., walking) game component 260a to illustratively generate a matched generated breathing curve (or alternative baseline/normal parameters of breathing). The average time to complete the third game component 260c is illustratively between 1 minute and 2 minutes.

Figure 22:
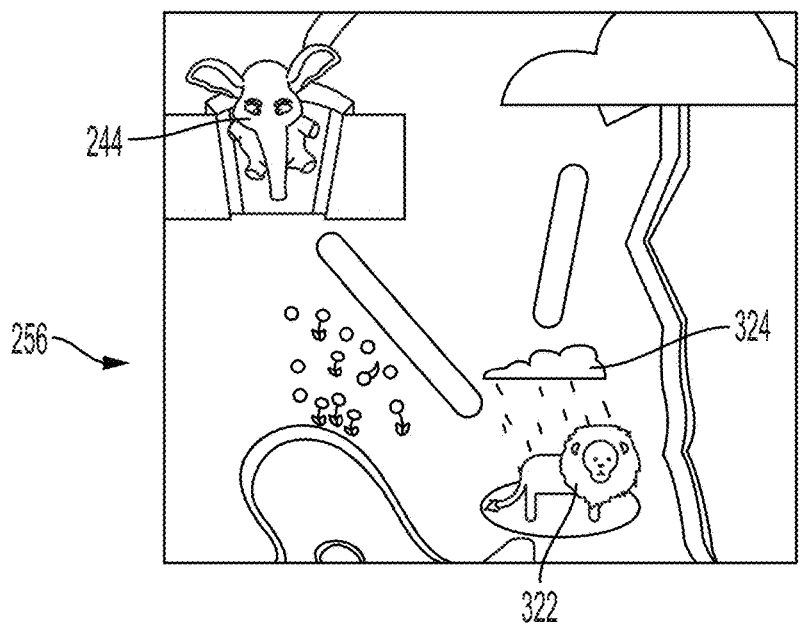
FIG. 22 is the illustrative sequential-phase-map screen of FIG. 16A, depicting the illustrative character having just exited the illustrative balloon-blow-up game component of the illustrative exhalation-validation phase and about to traverse to an illustrative animal-drying game of an illustrative breathing-pattern phase, in accordance with at least one embodiment.

FIG. 22 shows an illustrative main menu screen 256 upon initiating the third game component 260c. The patient 12 taps on a lion 322 under a rain cloud 324 but now uncovered. The elephant 244 will walk over to the lion 322. Tapping on the elephant 244 will start the third game component 260c.

Figures 23A, 23B:
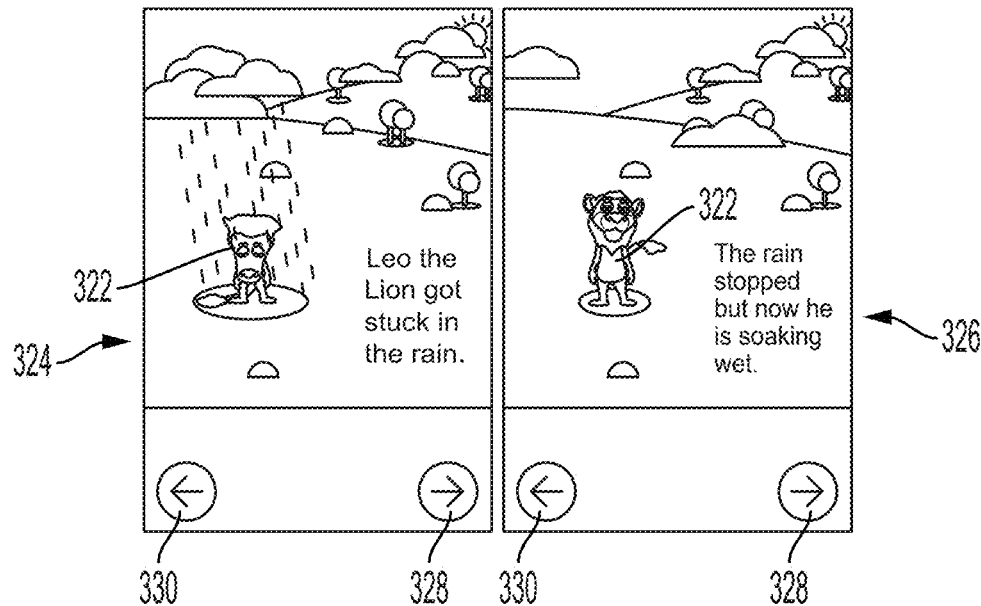
FIG. 23A is an illustrative first instructional screen of the illustrative animal-drying game of the illustrative breathing-pattern phase, in accordance with at least one embodiment.
FIG. 23B is an illustrative second instructional screen of the illustrative animal-drying game of the illustrative breathing-pattern phase, in accordance with at least one embodiment.

The third game component 260c continues to screens 324 and 326 of FIGS. 23A and 23B, respectively, where a story is displayed. As noted above, the third game component 260c may be the match generated breathing curve level or function. Some embodiments involve prompting a user to match breathing to a specific curve, while other embodiments do not. In some embodiments, instead of prompting a user to match breathing to a specific curve, the user is prompted to match (i.e. and e.g., encouraged to match and/or rewarded for matching) their breathing to parameters such as rate and/or depth. Early testing has revealed that matching breathing to the exact timing of a curve is challenging for some pediatric patients, while matching breathing to specified depths and approximate rates has proven more feasible for patients as a general matter. Both approaches are contemplated and considered to be valid techniques. Pressing the arrow 328 in the bottom right of the screen 324 will progress through the story from FIG. 23A to FIG. 23B, while pressing the arrow 330 in the bottom left of the screen 326 will return the story from FIG. 23B to FIG. 23A.

Figures 24A, 24B:
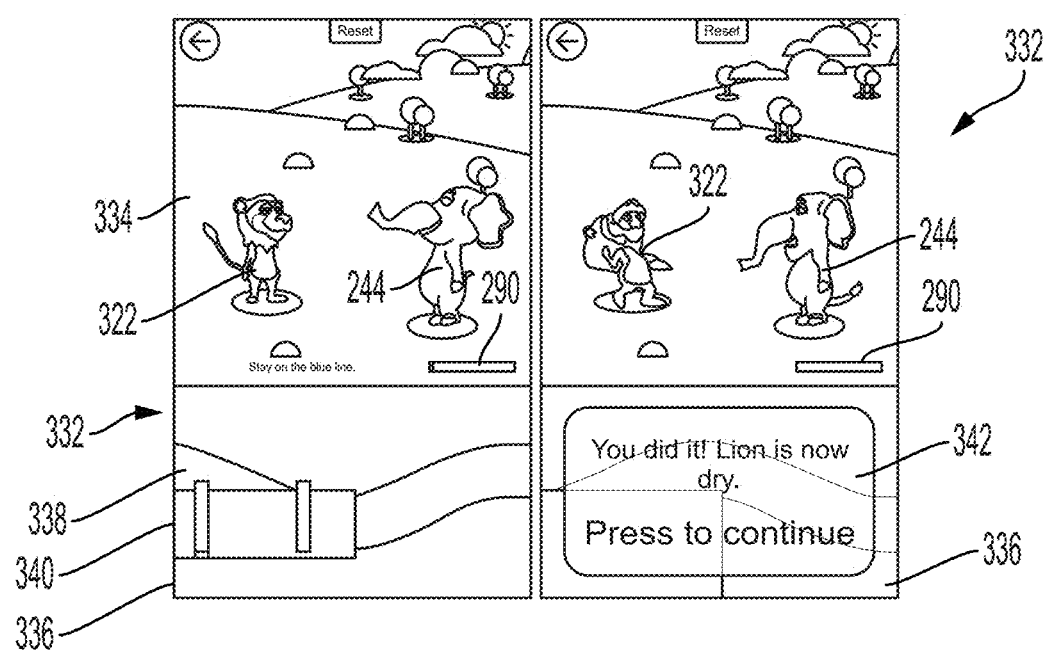
FIG. 24A is an illustrative first gameplay screen of the illustrative animal-drying game of the illustrative breathing-pattern phase, in accordance with at least one embodiment.
FIG. 24B is an illustrative second gameplay screen of the illustrative animal-drying game of the illustrative breathing-pattern phase, in accordance with at least one embodiment.

With reference to FIG. 24A, the screen 332 includes an upper portion 334 including a story board showing the elephant 244 whose trunk is configured to move in response to breathing of the patient 12 to simulate blowing dry the lion 322. The screen 332 further includes a lower portion 336 including a breathing curve 338 and an indicator bar 340 indicating the breathing (inhaling and exhaling) as detected by the pressure sensor 56. If the patient 12 breathes too deep or shallow, the indicator bar 340 will turn red. If the patient 12 breathes slightly off from the curve 338, the indicator bar 340 will turn yellow. If the patient 12 breathes within a predetermined tolerance of the curve 338, the indicator bar 340 will remain green.

When the progress bar 290 is completely filled, the lion 322 is shown as dry and happy in the upper portion 334 of the screen 332 of FIG. 24B. A button 342 is displayed in the lower portion 336 of the screen 332 providing an indication that the third game component 260c is complete. Tapping the button 342 returns the display 72 to the main menu screen 256.

Figure 25:
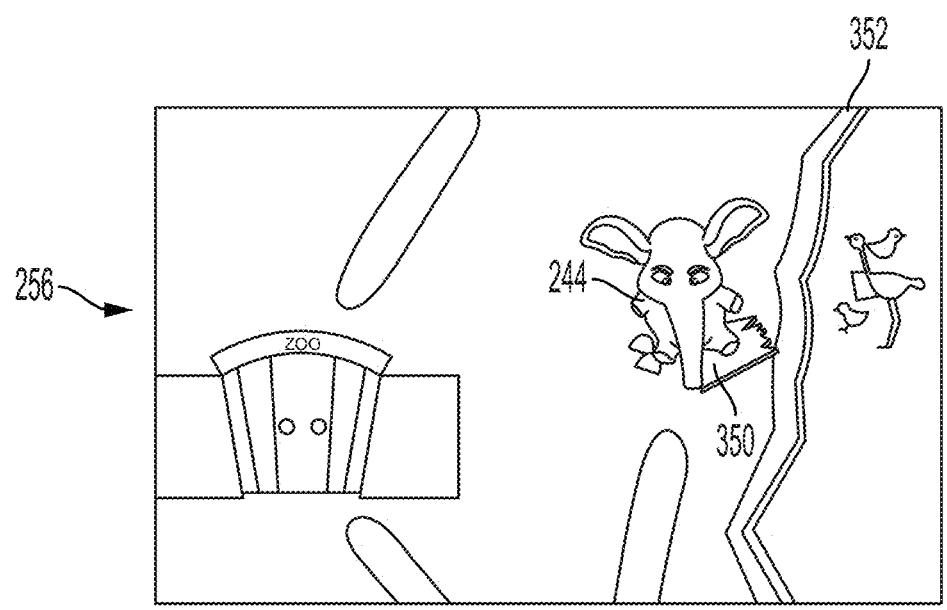
FIG. 25 is the illustrative sequential-phase-map screen of FIG. 16A, depicting the illustrative character having traversed to an illustrative canyon-crossing game of an illustrative active-induction phase, in accordance with at least one embodiment.

Referring again to FIG. 13, operation of the induction module 210 of the illustrative method begins at block 346, where the anesthesia machine 90 of the breathing circuit 22 has been activated by the caregiver. The fourth game component 260d is illustratively executed as part of the induction module 210. The calibration module 206 is illustratively executed in an induction phase of the patient 12. FIG. 25 shows the illustrative main menu screen 256 upon initiating the induction module 210. At block 348, the controller 16 detects when the patient 12 places the mask 74 over her mouth and/or nose by detecting air flow (inhaling and/or exhaling) via the pressure sensor 56.

The fourth game component 260d illustratively comprises the Canyon Level or floating game component. The illustrative purpose of the fourth game component 260d is to familiarize the patient 12 with using the mask assembly 20, and to engage and calm the patient 12 as she undergoes anesthesia induction. The average time to complete the fourth game component 260d is illustratively between 30 seconds and 90 seconds. The fourth game component 260d will illustratively play continuously (i.e., in a loop) until the patient 12 is induced (~2-4 minutes). Illustratively, an "auto" (or "autoplay") mode is provided so that a caregiver or clinician can tap when the patient 12 is becoming sleepy, so that the game component 260d will continue to progress as the patient 12 is anesthetized.

With further reference to the illustrative main menu screen 256 of FIG. 25, the patient 12 taps on a broken piece of wood 350 next to a brown jagged line 352 (e.g., canyon wall) that is now uncovered by the cloud 258. The elephant 244 will walk to the broken piece of wood 350. Tapping on the elephant 244 again will start the fourth game component 260d.

Figure 26B:
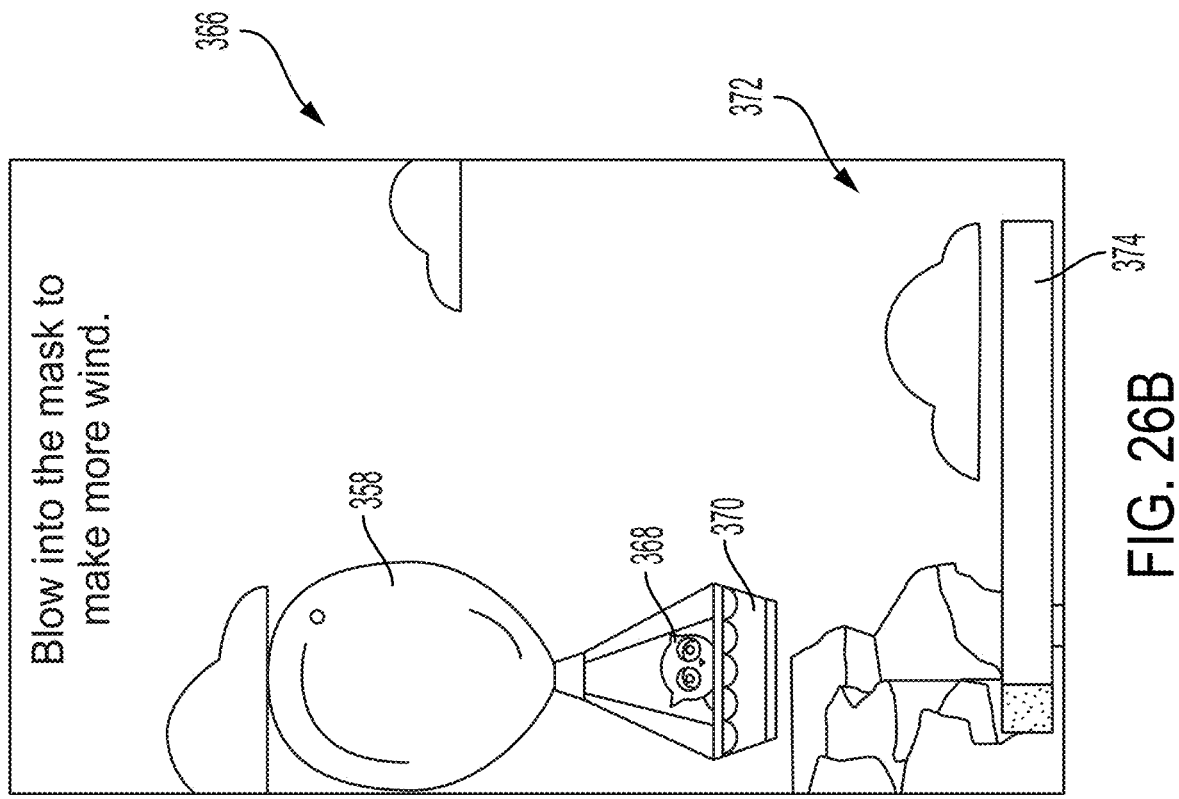
FIG. 26B is an illustrative second gameplay screen of the illustrative canyon-crossing game of the illustrative active-induction phase, in accordance with at least one embodiment.
Figure 26A:
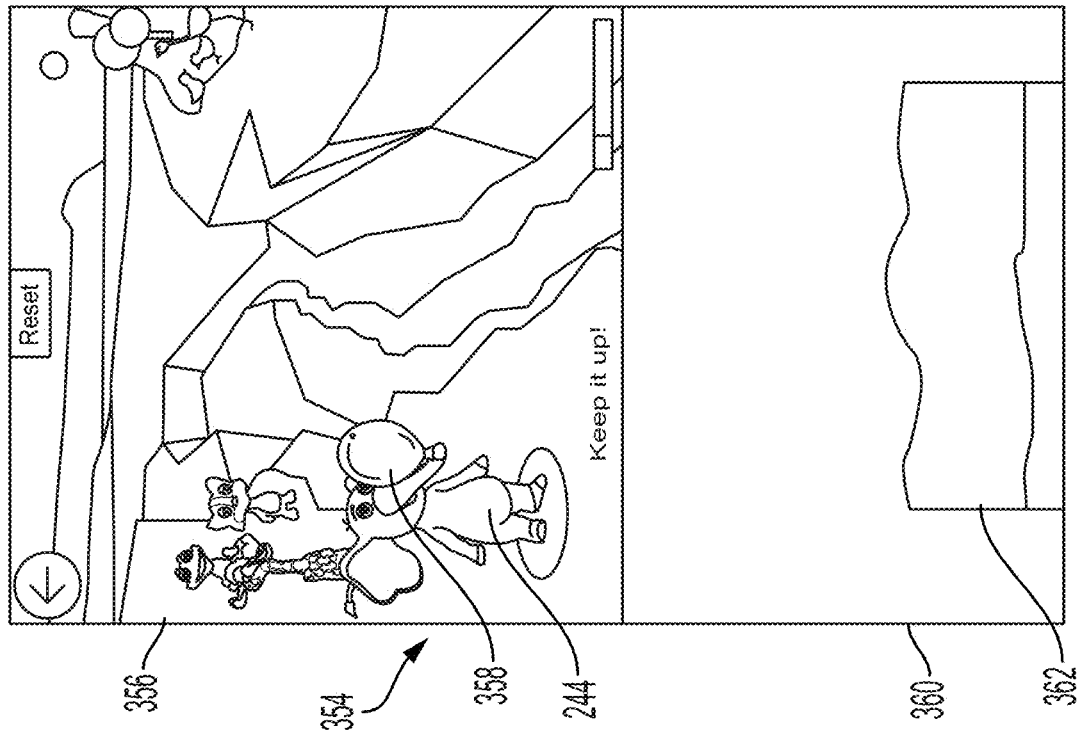
FIG. 26A is an illustrative first gameplay screen of the illustrative canyon-crossing game of the illustrative active-induction phase, in accordance with at least one embodiment.

With reference to FIG. 26A, the screen 354 includes an upper portion 356 defining a story board showing the elephant 244 whose trunk is configured to fill a balloon 358 in response to breathing of the patient 12. The screen 354 may further include a lower portion 360 including an indicator graph 362 providing an indication of patient breathing (inhaling and exhaling) as detected by the pressure sensor 56 as defined by block 364 in FIG. 13. The indicator graph 362 may change colors as breathing moves relative to a tolerance range. For example, if the patient 12 breathes too deep the indicator graph 362 will turn red. If the patient 12 breathes slightly off from an optimal path, the indicator graph 362 will turn yellow. If the patient 12 breathes within a tolerance of the optimal path, the indicator graph 362 will remain green. While the indicator graph 362 is shown as a calibrated curve based on the previously executed third game component 260c, other illustrative embodiments may use other baseline/normal parameters, such as calibrated parameters based upon baseline rate and/or depth of breathing. If an adequate baseline was not previously obtained in the game components 260b and/or 260c, then the fourth game component 260d will be calibrated to normal parameters for the age and/or size of the patient 12. Other illustrative embodiments for displaying tolerance may include other types of visual or auditory feedback, to indicate whether the patient 12 is breathing within the predetermined parameters.

Once the balloon 358 has been filled (based upon detected breathing volume from sensor 56), the fourth game component 260d continues with block 364 of FIG. 13 by displaying screen 366 of FIG. 26B. An animal 368 within a basket 370 supported by the balloon 358 is blown across the canyon 372 in response to the patient breathing into the mask assembly 20 (as detected by the pressure sensor 56). A progress bar 374 at the bottom of the screen 366 provides an indication of how the patient's breathing rate correlates to the breathing curve as calibrated by the calibration module 206.

In an alternative illustrative embodiment, the progress bar 374 may instead be included in the lower portion 360 of screen 354 (i.e., blowing up the balloon portion) where one to two big breaths complete the progress bar 374. In this illustrative embodiment, the color changing indicator graph 362 may be included in the screen 366, since this portion of the game component 260d takes longer to complete. Other illustrative embodiments may incorporate the "green/yellow/red" concept of the indicator graph 362 into actual game play, where the breathing curve is a part of the game (i.e. flying/jumping/swimming over and under objects, collecting jewels/coins are accomplished only by breathing in a calm and controlled manner).

The goal of the fourth game component 260d is for the patient 12 to exhale into the mask assembly 20. This will "fill" the balloon 358 (FIG. 26A), and blow the animal 368 to the other side of the canyon 372 (FIG. 26B). The balloon 358 will turn into a hot air balloon to carry each of a plurality of animals 368, one by one, across the canyon 372 and safely to the other side.

Figure 26C:
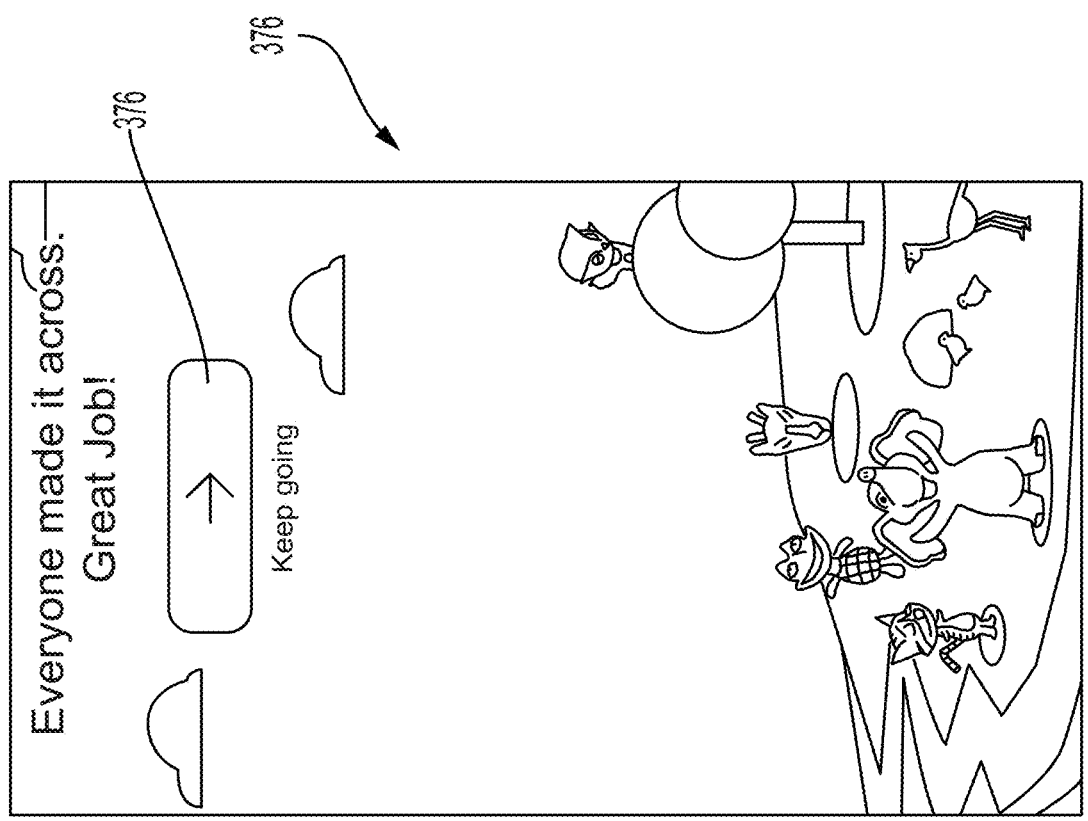
FIG. 26C is an illustrative third gameplay screen of the illustrative canyon-crossing game of the illustrative active-induction phase, in accordance with at least one embodiment.

When the progress bar 374 is completely filled, the elephant 244 and other animals 368 carried across the canyon 372 are shown celebrating in the screen 376 of FIG. 26C. With reference to block 377 of FIG. 13, when the progress bar 374 fills, the game component 260d ends at block 379. A button 378 may be tapped to return to the main menu screen 256 of FIG. 16A.

An illustrative embodiment of the fourth game component 260d only detects mask on/mask off and exhalation (which blows up balloons and propels the balloon across the canyon). An alternative illustrative embodiment of the fourth game component 260d is a combination level, that will have features of all the prior game components: Recognizes mask on/off (like walking to the zoo level), exhalation to blow up balloons (like zoo gates level), and the "matched breathing curve" level (blow-dry lion) which requires the user to stay within the calibrated or designated inhalation/exhalation parameters when crossing the canyon in order to win. This combination level allows the child to use all the skills she has learned in the prior games during the anesthesia induction process and facilitates patient interaction and calm breathing during induction.

Figure 27:
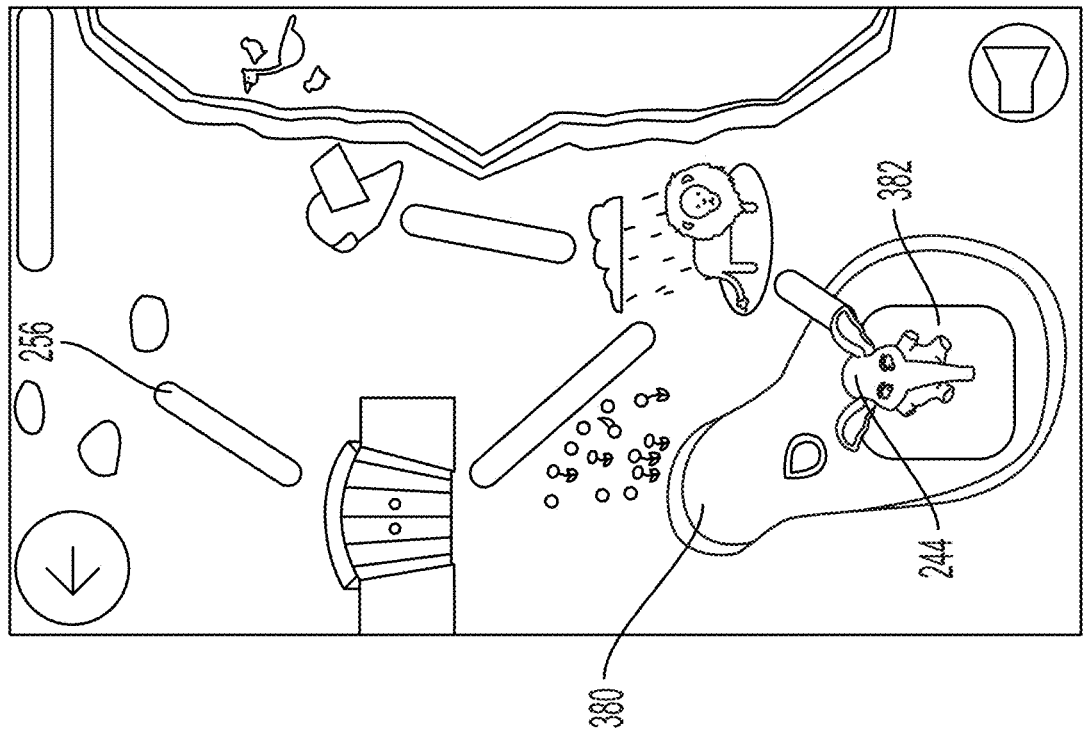
FIG. 27 is the illustrative sequential-phase-map screen of FIG. 16A, depicting the illustrative character having traversed to and about to enter an animal-coloring game of an illustrative transport phase, in accordance with at least one embodiment.

A fifth game component 260e illustratively comprises the Tap mini game component. The illustrative purpose of the fifth game component 260e is to sooth the patient 12 while waiting for anesthesia induction (e.g., during patient transport). As such, this optional fifth game component 260e is configured to occur prior to the anesthesia induction associated with the fourth game component 260d. FIG. 27 shows an illustrative main menu screen 256 upon initiating the fifth game component 260e. The patient 12 taps on a pond 380 now uncovered by the cloud 258. The elephant 244 will walk to an island 382. By tapping on the elephant 244 again, the fifth game component 260e will begin.

Figure 28:
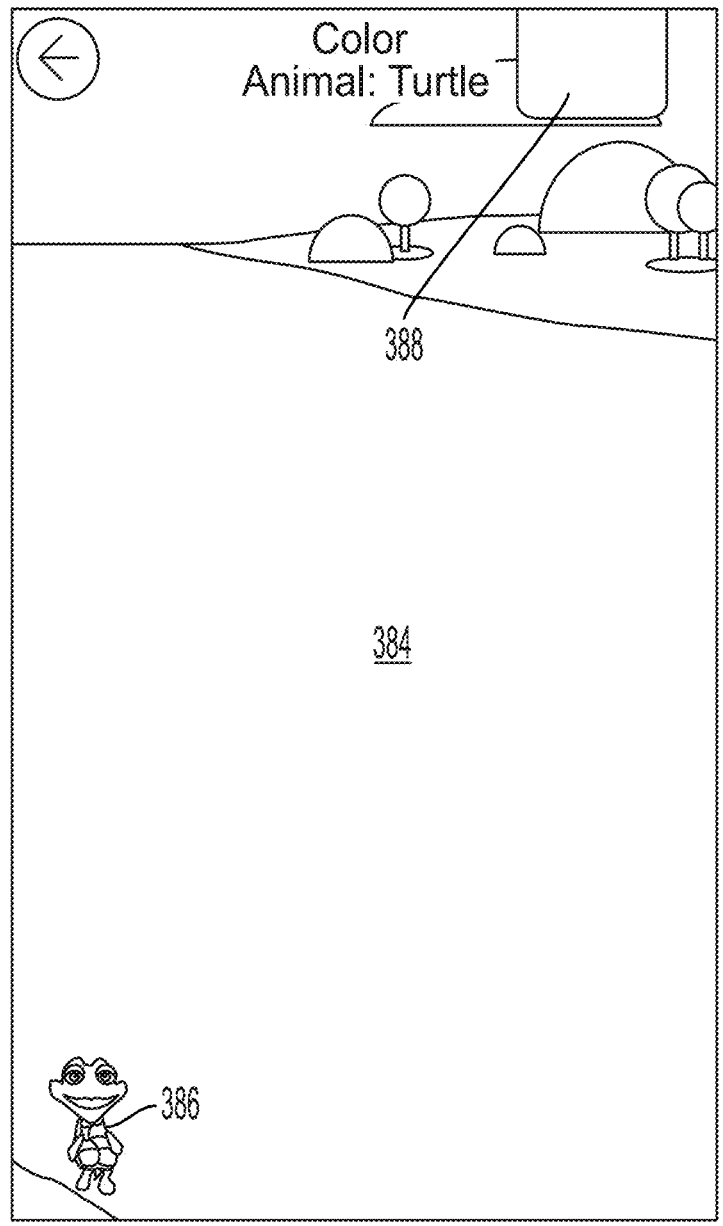
FIG. 28 is an illustrative gameplay screen of the animal-coloring game of an illustrative transport phase, in accordance with at least one embodiment.
Figure 29A:
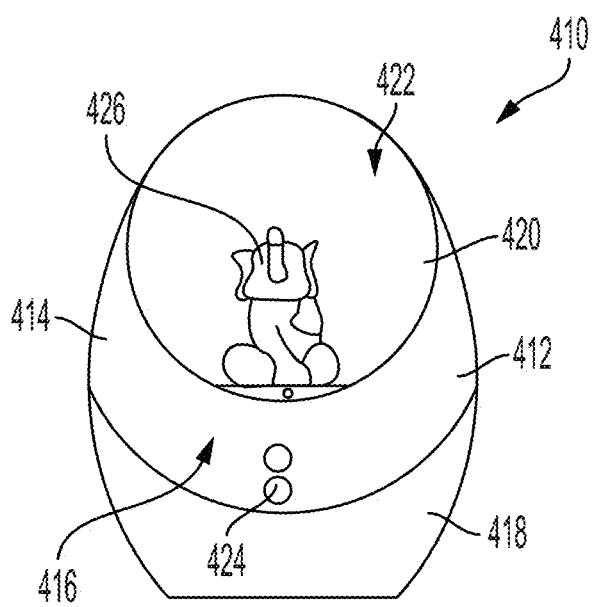
FIG. 29A is a first perspective view of an illustrative three-dimensional (3D) interactive device providing a structural gameplay aspect, in accordance with at least one embodiment.
Figure 29B:
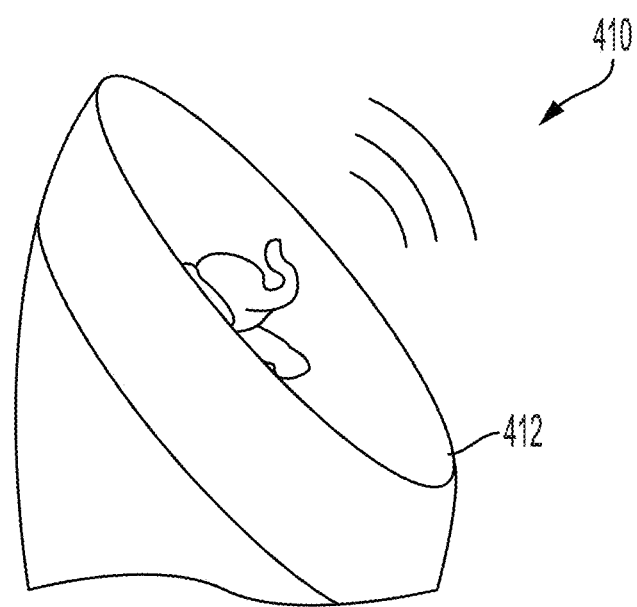
FIG. 29B is a second perspective view of the illustrative 3D interactive device of FIG. 29A, in accordance with at least one embodiment.
Figure 29C:
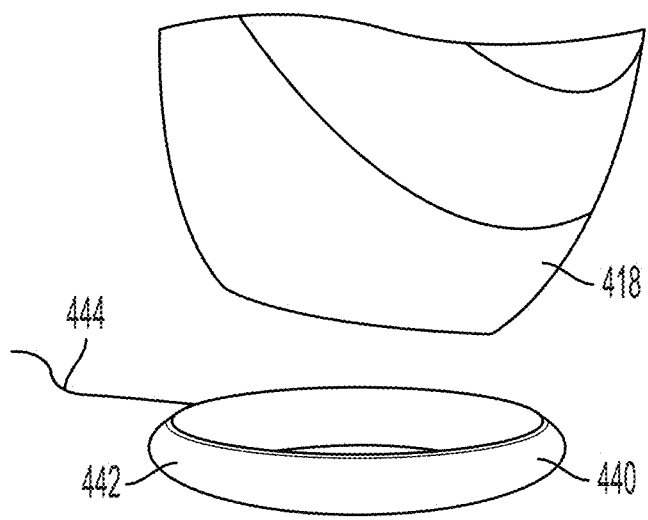
FIG. 29C is a third perspective view of the illustrative 3D interactive device of FIG. 29A, in accordance with at least one embodiment.
Figure 29D:
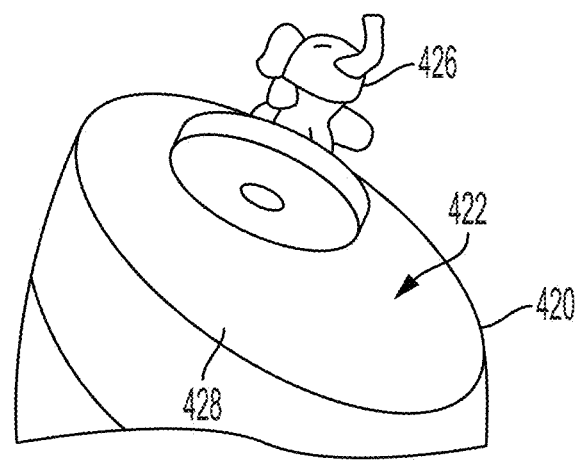
FIG. 29D is a fourth perspective view of the illustrative 3D interactive device of FIG. 29A, in accordance with at least one embodiment.
Figure 29E:
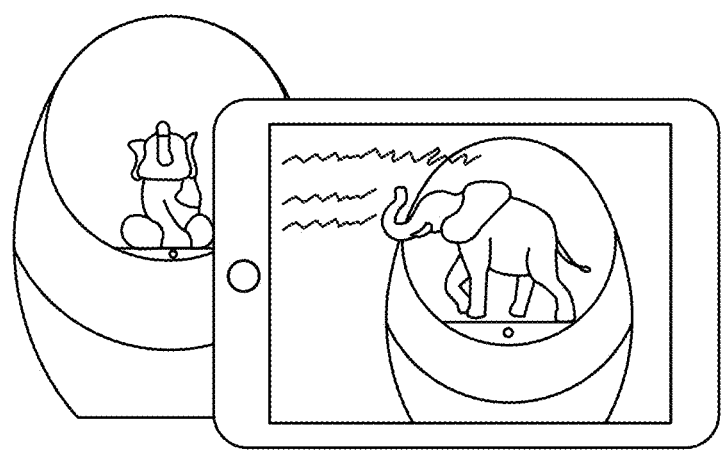
FIG. 29E is a second perspective view of the illustrative 3D interactive device of FIG. 29A, in accordance with at least one embodiment.
Figure 29F:
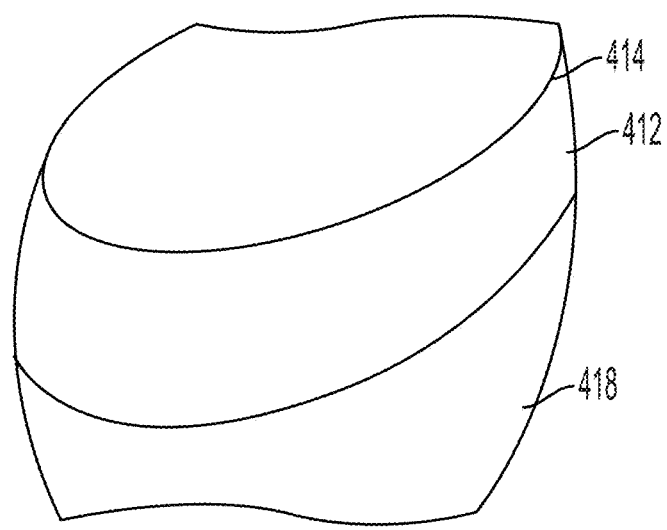
FIG. 29F is a sixth perspective view of the illustrative 3D interactive device of FIG. 29A, in accordance with at least one embodiment.

With reference to FIG. 28, the screen 384 includes an animal 386 and an associated color icon 388. The game component 260e is configured to allow the patient 12 to personalize the features of her induction game 260d (e.g., selecting types and sequences of animals (crossing the canyon, for example), selecting balloon colors, etc.) In one illustrative embodiment, the patient 12 may associate a color icon 388 with an animal 386. It should be appreciated that other games may be utilized as the fifth game component 260e.

With reference to FIGS. 29A-29F, another illustrative respiratory feedback system 410 of the present disclosure is shown as including an interactive patient device 412 in a three-dimensional (3D) form. The patient device 412 illustratively includes a housing or shell 414 defining a user interface 416. A lower portion or base 418 of the housing 414 may be formed of a relatively soft material, such as an elastomer based material, to facilitate comfortable contact by the patient 12. An upper portion or bowl 420 is coupled to the base 418 and defines a receiving chamber 422 and a front interface 424. The bowl 420 may be formed of a thermoplastic, such as a relatively hard acrylonitrile butadiene styrene (ABS) or polylactide (PLA).

In an illustrative embodiment, a removable object 426, such as an animal, a doll or a figurine, is removably supported on a platform 428 within the receiving chamber 422 of the bowl 420. A conventional coupler 430, such as a friction fit, adhesive or magnet, may releasably couple the object to the platform 428. The object 426 illustratively includes an identification member, such as an RFID tag, configured to be detected by a sensor or receiver supported by the housing 414. A controller is operably coupled to the sensor and is received within the housing 414. The sensor is configured to read the identification member and provide a signal thereof to the controller. As such, the controller may customize operation of the system 410 based upon the detected identification member and associated object 426. Illustratively, the controller activates the system 410 upon detecting the object 426 is in contract with the platform 428.

A first light emitter is illustratively provided on the inside of the bowl 420, and a second light emitter is illustratively provided on the front interface 424. The light emitters are operably coupled to the controller and provide breathing feedback based upon respiratory parameters (e.g., gas pressure) detected by sensor(s). Illustratively, the intensity and/or color of the light emitters may vary to provide a soothing effect to the patient, and/or to indicate compliance with a desired breathing pattern and/or volume. For example, the light emitters may provide flashing light when the desired breathing pattern is satisfied.

An audible device or speaker may be supported within the housing 414 and accompany the light emitters. The speaker may emit a peaceful ascending white noise to provide a soothing effect to the patient 12.

A power supply may be defined by rechargeable batteries received within the base 418 of the housing 414. A charging station 440 may operably couple with the base 418 to charge the batteries. Illustratively, the charging station 440 may be defined by an annular ring 442 supporting the base 418 and wirelessly charging the batteries. An electrical cord 444 may electrically connect the ring 442 with a conventional source of power (electrical outlet).

In certain illustrative embodiments, augmented reality may provide informational interactions for the patient. For example, a camera, a tablet (e.g., iPad) or smartphone can bring the patient's chosen object (e.g., animal) to life with virtually displayed information.

Figure 30A:
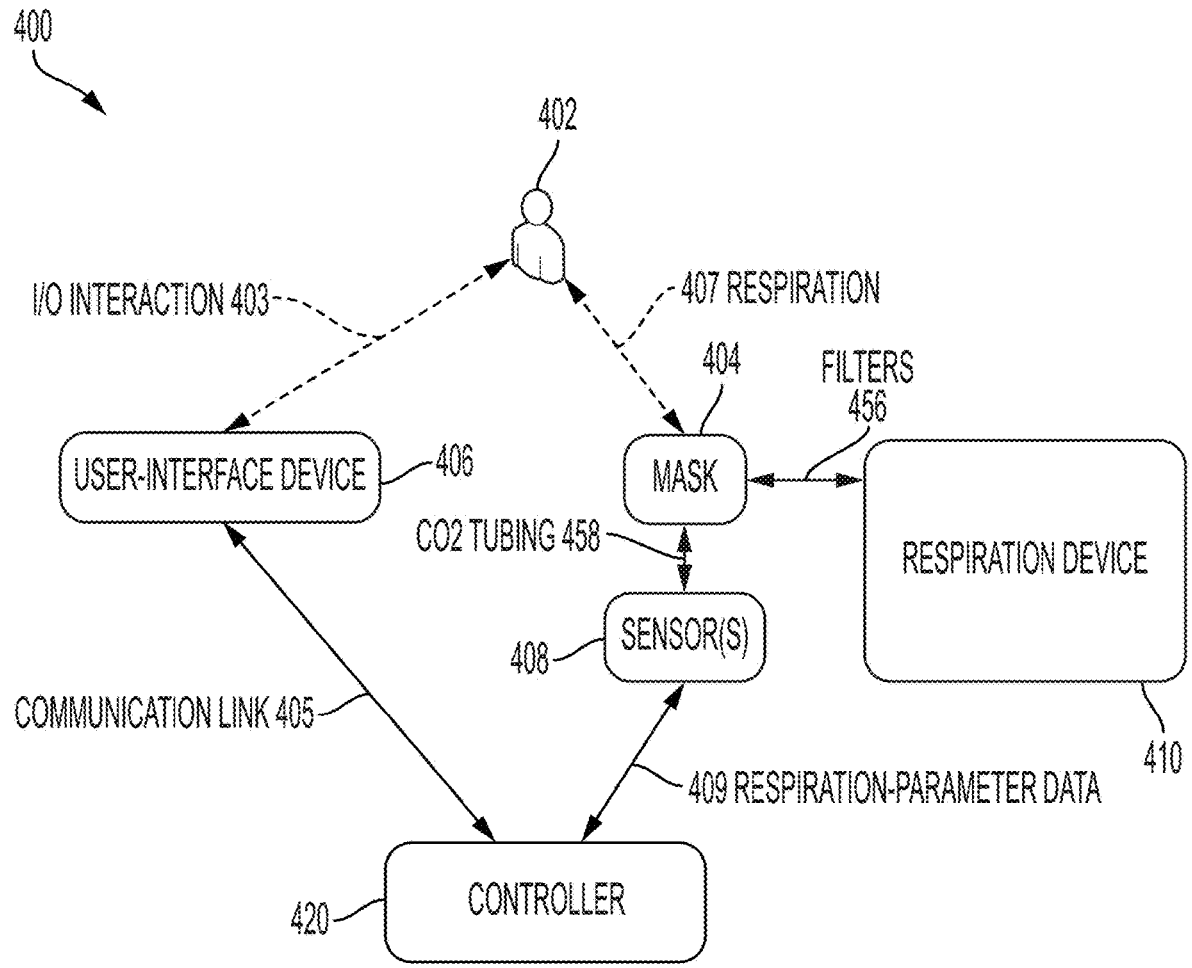
FIG. 30A is a diagram depicting an illustrative arrangement, in accordance with at least one embodiment.

FIG. 30A is a diagram depicting an illustrative arrangement, in accordance with at least one embodiment. The illustrative arrangement 400 includes a user 402, a user-interface device 406, a mask 404, one or more sensors 408 (e.g., pressure sensors, flow sensors, temperature sensors, and/or other types of sensors), a respiration device 410, and a controller 420. In an illustrative scenario, the user 402 is a pediatric surgery patient. As shown at 403, the user 402 interacts at an input/output (I/O) level with the user-interface device 406, which is connected via a wired (e.g., Ethernet or USB) or wireless (e.g., Bluetooth or Wi-Fi) communication link 405 to the controller 420.

The user 402 is also operably engaged (e.g., wearing) the mask 404 and respiring into and out of the mask 404 as shown generally at 407. The mask 404 is connected via $CO_2$ tubing 458 to the sensors 408, which in turn passes respiration-parameter data to the controller 420 as shown generally at 409. The mask 404 is also fluidly connected with the respiration device 410 via filters 456. In an embodiment, the respiration device 410 is an anesthesia machine, though other types of respiration devices could be used instead, some examples of which are described herein. In some embodiments, the sensors 408 and/or the controller 420 are components of the respiration device 410. For instance, the respiration device 410 could be an anesthesia machine that includes the sensors 408. In another example, the controller 420 could be realized on a chip that is a component of the respiration device 410. And other configurations could be used.

The controller-on-a-chip approach is also used in an embodiment in which the respiration device is a CPAP machine. Whether in an anesthesia machine, a CPAP machine, or another type of machine, the controller chip in some embodiments sends breathing data that is already being collected by its host machine to the user-interface device 406 via the communication link 405. In general, a number of different types of respiration devices could be used, including but not limited to PAP devices such as CPAP devices and BiPAP devices, nebulizers, anesthesia machines, PEP devices, ventilators, inhalers, spirometry devices, incentive spirometry devices, and/or any other types of respiration devices deemed suitable by those of skill in the art for a given implementation or in a given context. As the term respiration device is used herein, a respiration device could be any of these possibilities, could include any of these possibilities, and could be included in any of these possibilities. Some example adapters are discussed herein for facilitating the use of the present systems and methods with various examples of these possibilities.

Figure 30B:
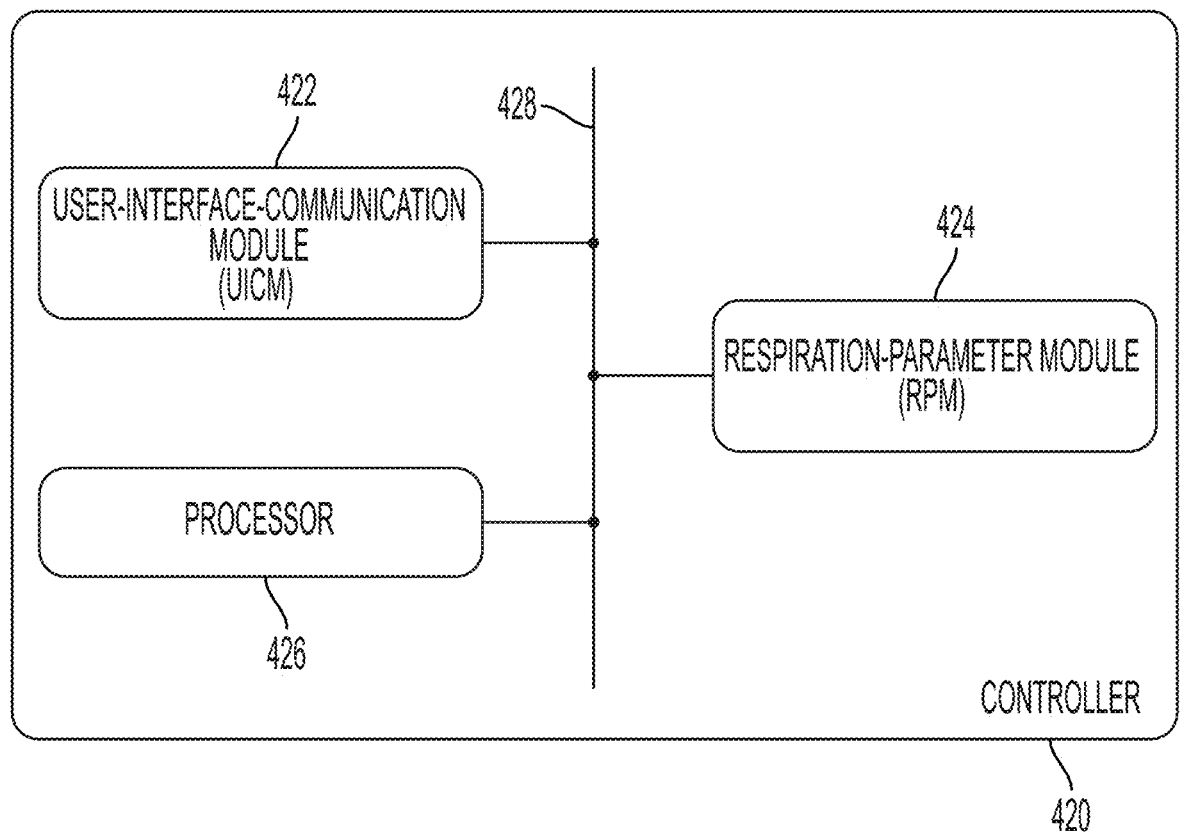
FIG. 30B is a diagram depicting an illustrative architecture of an illustrative controller, in accordance with at least one embodiment.

FIG. 30B is a diagram depicting an illustrative architecture of the controller 420, which is shown as including a system bus 428 that communicatively interconnects a user-interface-communication module (UICM) 422 that is configured to operably communicate with the user-interface device 406 via the communication link 405. The controller 420 further includes a respiration-parameter module (RPM) 424 that is configured to output the respiration-parameter data 409, which in at least one embodiment includes a respiration-data stream that is reflective of one or more respiration-parameter values of one or more respiration parameters associated with ongoing respiration 407 of the user 402 via the mask 404, which itself is operably engaged with the respiration device 410. As such, the user is operably engaged with at least the mask 404 and the respiration device 410. The controller 420 also includes a processor 426 that is configured to operably communicate with both the UICM 422 and the RPM 424 and that is further configured to carry out a set of functions such as the herein-described method 430, the herein-described method 700, and/or one or more variations thereof.

With respect to the physical arrangement of the various entities that are depicted in the arrangement 400, other possibilities are contemplated as well. For example, the controller and 420 the user-interface device 406 could be components of a single device. As another example, the controller 420 and the user-interface device 406 could be realized in different devices that are communicatively connected with one another, as depicted in the illustrative arrangement 420. In another example, the user-interface device 406 and the controller 420 could be realized in different devices that are nevertheless received in and supported by a single case. And other configurations will occur to those of skill in the art having the benefit of this disclosure. In some implementations, in order to reduce chances of infection, collect less noisy breathing data, and/or for one or more other purposes, the mask 404 and the sensors 408 are decoupled from one another by a distance that is on the order of 8-10 feet, perhaps connected across that distance by a cord and/or tubing of sufficient length.

Figure 30C:
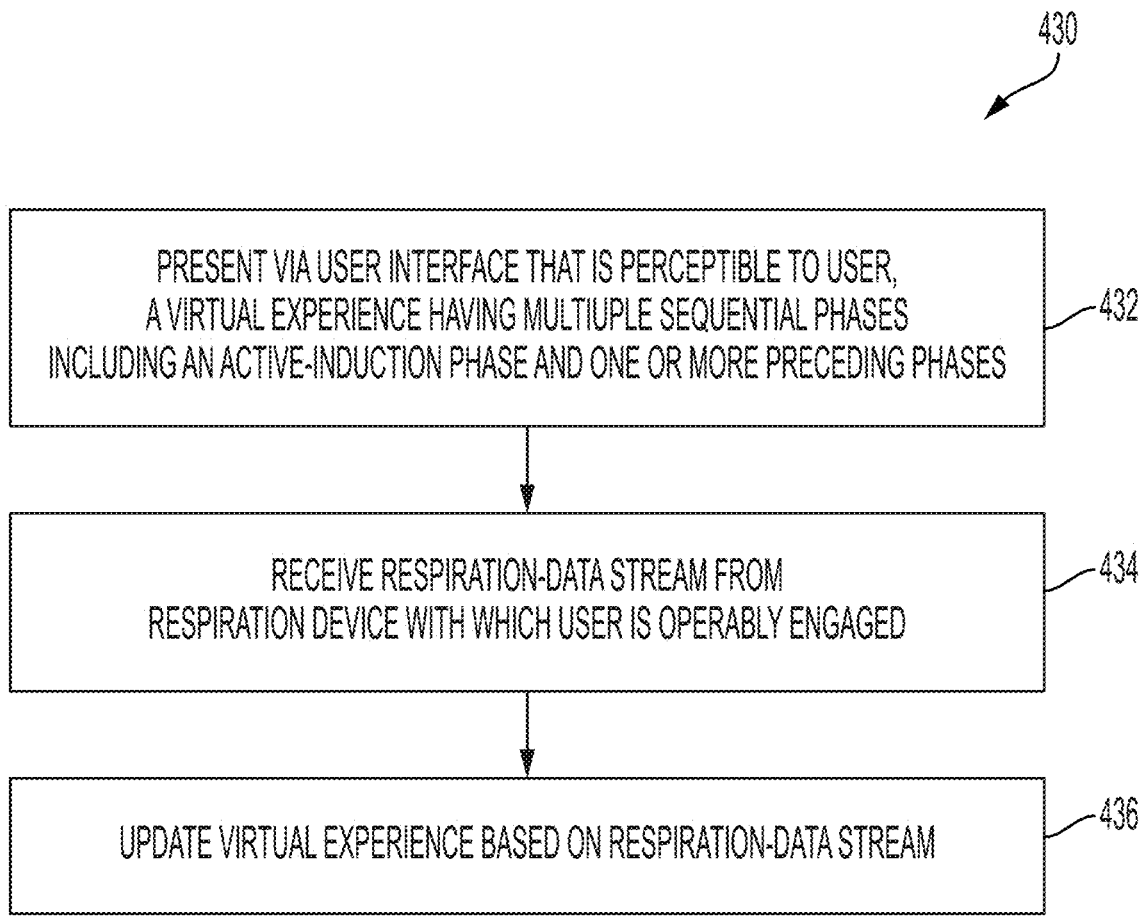
FIG. 30C is an illustrative flowchart of a first illustrative method, in accordance with at least one embodiment.

FIG. 30C is an illustrative flowchart of a method 430 that in at least one embodiment is carried out by the controller 420. At step 432, the controller 420 presents a virtual experience via a user interface that is perceptible to a user. In an embodiment, the controller 420 carries out step 432 at least in part by transmitting data via the communication link 405 to the user-interface device 406 for presentation via the user interface of that device, which could be a smartphone, a tablet, a laptop computer, and/or another suitable device. The virtual experience could be visual, audible, and/or tactile. Example virtual experiences are described herein in connection with various series of screenshots of animal-based video games meant for children, but any sort of visual experience could be implemented.

Moreover, some embodiments include an olfactory component as well, in some cases contemporaneously with a virtual experience, in some cases integrated with the virtual experience. Some contemporaneous embodiments involve scenting the masks pre-operatively and the anesthesia circuit during induction. It is noted that sevoflurane gas is particular known for having a pungent odor. As a general matter, some pediatric patients in particular are more receptive to having the mask on in preop and during induction when a pleasant scent is added to the equipment. In some embodiments, the olfactory component is incorporated into the virtual experience in that there is a *nexus* between a scent provided to the patient and something visual and/or audible occurring in the visual experience. Virtual images are selectable in some embodiments to cause corresponding scents being introduced to the patient (e.g., an image of an orange and an orange-fruit or orange-candy scent). In some cases, a mask has an additional port operable for providing scents to the patient. Some examples of incorporating an olfactory component into a virtual experience are described in U.S. Pat. No. 5,610,674, issued Mar. 11, 1997 and entitled "Precision Fragrance Dispenser Apparatus," the entire disclosure of which is hereby incorporated herein by reference.

At step 434, the controller 420 receives the respiration-parameter data 409 from the mask 404 with which the user is operably engaged. In this example, the combination of the mask 404 and the respiration device 410 could be considered to be a respiration device. The mask 404 on its own could be considered a respiration device as well. The respiration-parameter data 409 comes to the controller 420 by way of the sensors 408. Example respiration parameters include pressure, chemical contents of the air in the mask 404, breathing rate, airflow rate, temperature, and/or the like. In some embodiments, the data in the respiration-parameter data reflects respiration parameters such as respiration frequency, strength, and/or duration.

At step 436, the controller 420 updates the virtual experience based at least in part on the respiration-parameter data 409. Various ways in which the controller carries out step 436 in various different embodiments are described herein. Some example ways include depicting a balloon inflating, depicting a hot air balloon rising and falling with the rhythm of the breathing, depicting an elephant spraying water from its trunk on a particular target, and so forth. The possibilities are limitless with respect to the ways in which the values of one or more respiration parameters could be converted into visual, audible, and/or tactile outputs as part of a virtual experience such as a video game.

Described below in connection with a number of screenshots is a virtual experience that includes a plurality of sequential phases that have an associated phase sequence. The plurality of sequential phases includes an active-induction phase that corresponds in time to the user 402 receiving anesthetic induction from the respiration device 410 via the mask 404. In other embodiments involving other types of respiration devices, the active-induction phase is replaced with what is referred to herein using the more general term of active-treatment phase, which could include receiving one or more medicaments and/or one or more form of medical treatment and/or simply interacting with a respiration device at the direction or according to the instructions provided by a medical professional such as a doctor, nurse, technician, nurse practitioner, physician's assistant, and/or the like or other person such as a meditation leader, therapist, or other caregiver, just to name a few examples.

In addition to the active-induction phase, the plurality of sequential phases also includes a set of one or more phases that each precede the active-induction phase in the phase sequence. Several examples of such preceding phases are described herein as well. In some embodiments, as described herein, the sequential phases correspond respectively with different visual indicia presented via the user interface. FIG. 16A is one such example, there multiple phases are represented simultaneously on a map of a virtual geographic area, which in that case is a zoo but could instead by a wildlife reserve, a park, a city, and/or any other option deemed suitable for a given audience.

Figure 31A:
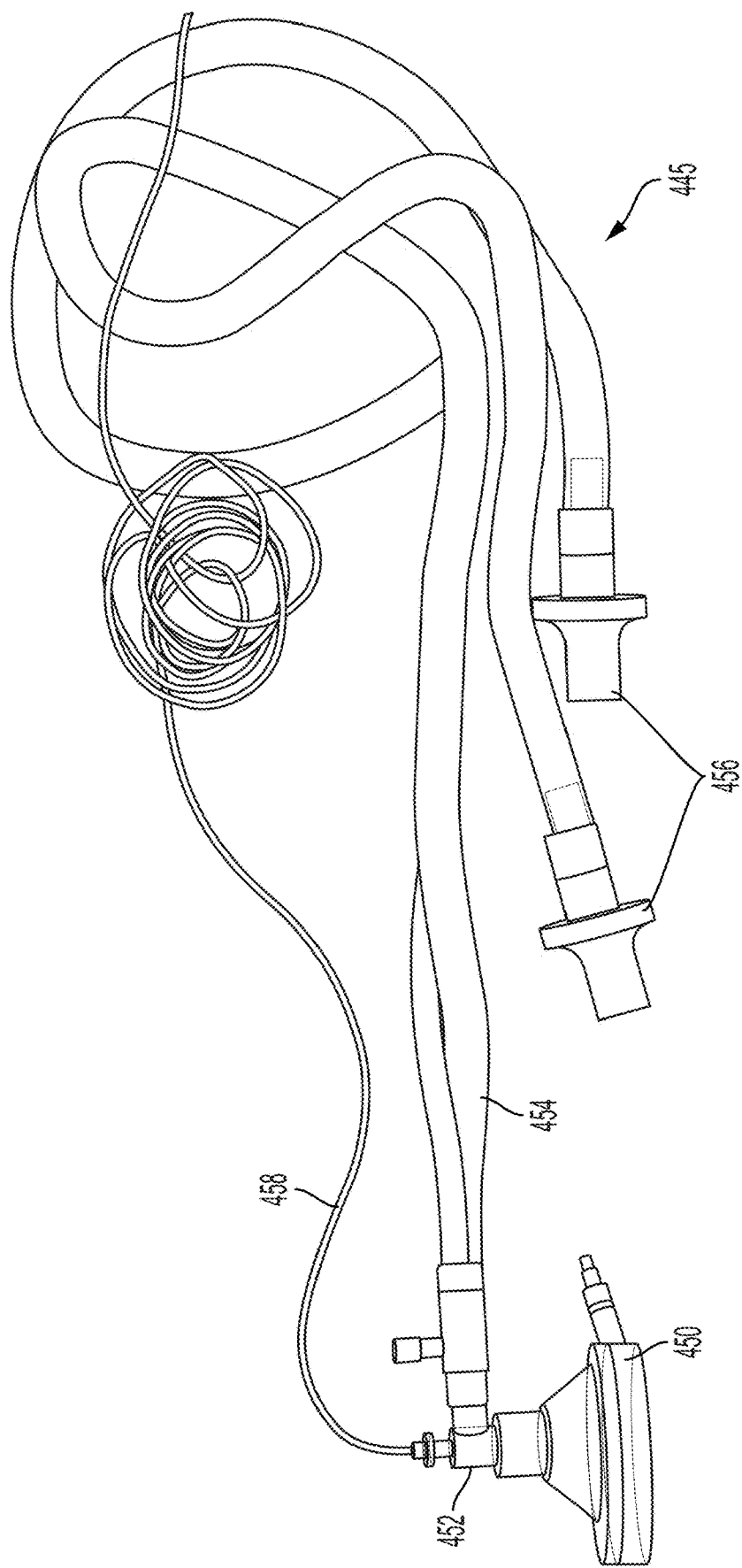
FIG. 31A is a perspective view of an illustrative standard setup for anesthesia equipment, said equipment being usable in accordance with at least one embodiment.

FIG. 31A is a perspective view of an illustrative standard setup for anesthesia equipment that is usable in accordance with at least one embodiment. In particular, FIG. 31A depicts an arrangement 445 that shows an anesthesia mask 450 (which could correspond to the above-mentioned mask 404), an elbow connector 452, anesthesia circuit tubing 454, the above-mentioned filters 456 (that connect to an anesthesia machine), and the above-mentioned $CO_2$ tubing 458, which typically connects to the anesthesia machine to measure carbon dioxide.

Figure 31B:
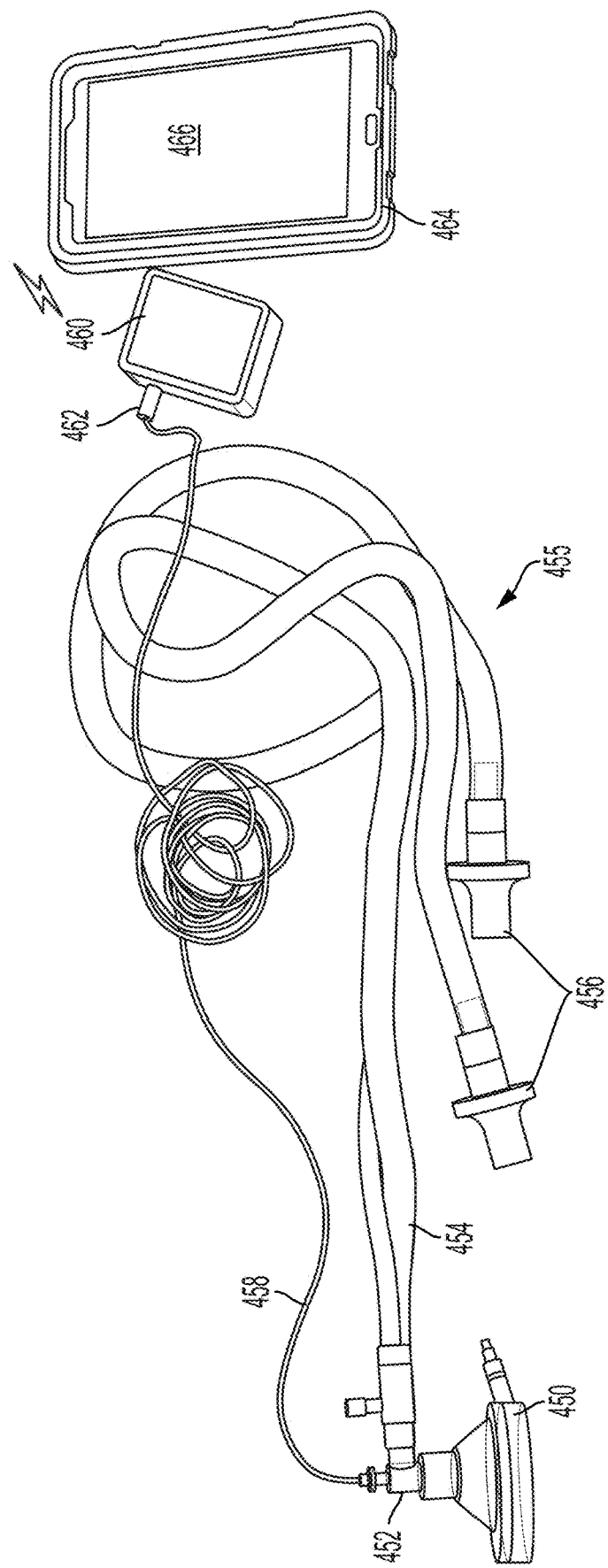
FIG. 31B is a perspective view of an illustrative arrangement that includes both the illustrative standard setup for anesthesia equipment of FIG. 31A as well as an illustrative controller box and an illustrative computing device having an illustrative user interface, in accordance with at least one embodiment.

FIG. 31B depicts an illustrative arrangement 455 that includes all of the equipment that is in the arrangement 445 as well as both the illustrative standard setup for anesthesia equipment of FIG. 31A as well as a controller box 460 that connects to the $CO_2$ tubing 458 at a connection point 462 and a tablet 464 having a touchscreen 466. The tablet 464 is an example of the user-interface device 406. In the arrangement 455, the controller box 460 includes at least the controller 420 and the sensors 408. It is noted that, if needed or desired, given the arrangement 455, a clinician could still measure $CO_2$ by connecting to the lower sampling port by removing a cap on the elbow connector 452.

Figure 32A:
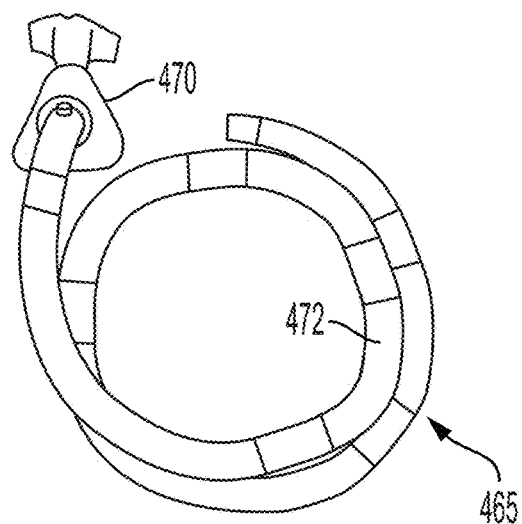
FIG. 32A is a perspective view of illustrative standard equipment for use in a positive-airway-pressure (PAP) application, said equipment being usable in accordance with at least one embodiment.
Figure 32B:
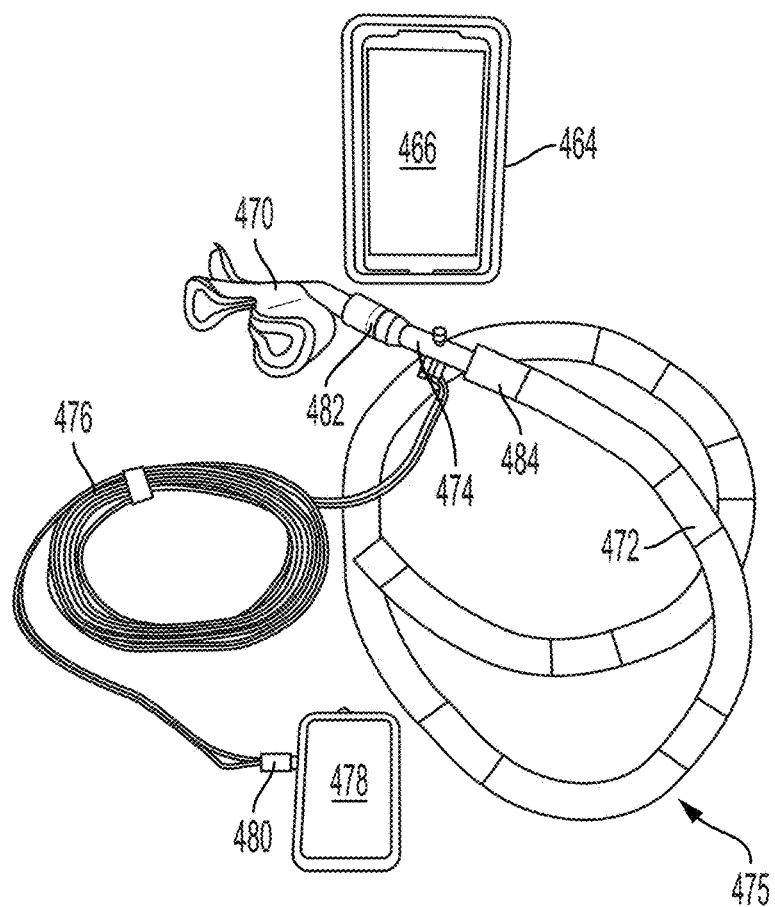
FIG. 32B is a perspective view of an arrangement that includes both the illustrative standard equipment for use in a PAP application of FIG. 32A as well as an illustrative spirometry adapter, illustrative spirometry tubing, an illustrative controller box, an illustrative computing device having an illustrative user interface, and illustrative mask and tubing adapter connectors, in accordance with at least one embodiment.

FIG. 32A depicts an arrangement 465 of equipment usable in a PAP application, including a nasal mask 470 and tubing 472, which connects in illustrative PAP setups to a PAP machine such as a CPAP machine or a BiPAP machine. FIG. 32B depicts an arrangement 475 that adapts the arrangement 465 for use in connection with the present systems and methods. The arrangement 475 includes the nasal mask 470 (which corresponds to the mask 404) and the tubing 472, and further includes a spirometry adapter 474, spirometry tubing 476, a controller box 478 that is connected to the spirometry tubing 476 at a connection point 480, and the above-mentioned tablet 464 having the touchscreen 466. An example of the spirometry adapter 474 and the spirometry tubing 476 is the Pedi-Lite+ Spirometry Kit, Pediatric, 3 m/10 ft, item number M1032634, manufactured by GE Healthcare of Chicago, IL.

Like the controller box 460, the controller box 478 includes both the controller 420 and the sensors 408. The tubing 472 connects to the PAP machine. Also pictured is a connective adapter 482 that adapts the nasal mask 470 to be in operable fluid communication with the spirometry adapter 474, as well as a connective adapter 484 that adapts the spirometry adapter 474 to be in operable fluid communication with the tubing 472. In a CPAP application, it has been determined to be advantageous to "zero out" the pressure being applied to the patient. Such a zeroing-out function removes the impact of background/ambient pressure. In typical CPAP implementations, a differential pressure sensor is used.

Figure 33B:
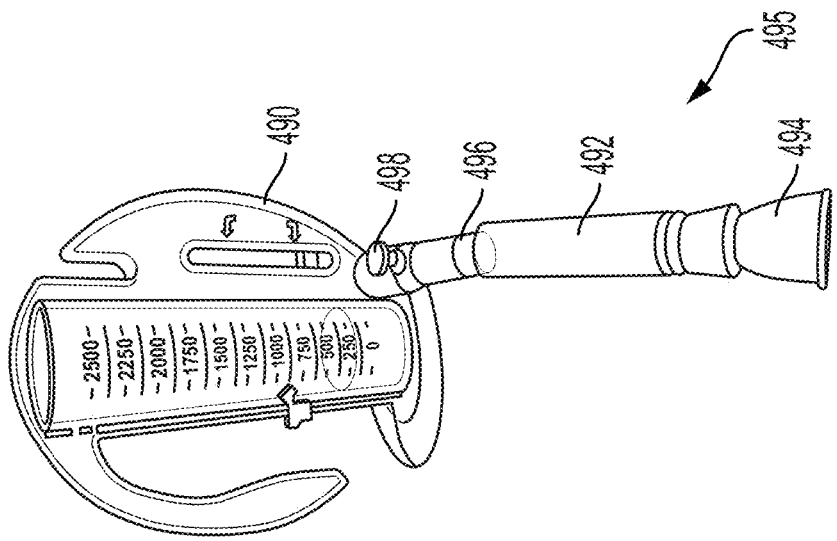
FIG. 33B is a perspective view of an arrangement that includes both the illustrative standard incentive spirometer of FIG. 33A as well as an illustrative adapter for carbon-dioxide ($CO_2$) tubing or oxygen ($O_2$) tubing, in accordance with at least one embodiment.
Figure 33A:
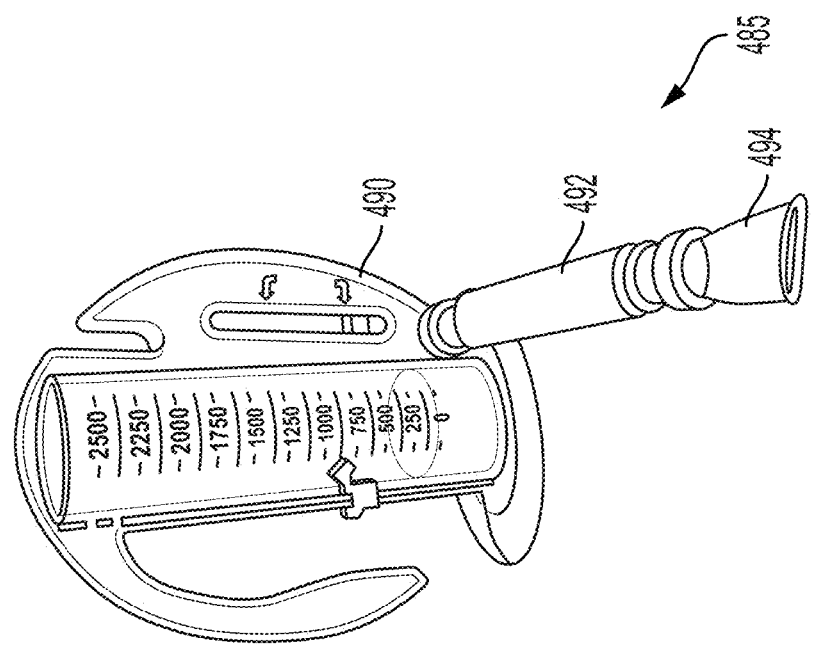
FIG. 33A is a perspective view of an illustrative standard incentive spirometer, said device being usable in accordance with at least one embodiment.

FIG. 33A depicts an arrangement 485 of equipment usable in an incentive spirometry setup that includes an incentive spirometry device 490 fluidly connected to an air tube 492, which is in turn fluidly connected to a mouthpiece 494. FIG. 33B depicts an arrangement 495 that adapts the arrangement 485 for use in connection with the present systems and methods. The arrangement 495 includes all of the elements of the arrangement 485, and additionally includes an illustrative adapter 498 interposed between— and in fluid communication with both—the incentive spirometry device 490 and the air tube 492. The adapter 498 includes a port for connecting to $CO_2$ tubing (and also fits oxygen ($O_2$) tubing), in accordance with at least one embodiment. Some incentive spirometry devices have an existing oxygen ($O_2$) port that could be used to connect to, e.g., a controller box in a manner similar to that described herein with respect to anesthesia and PAP implementations. In an example virtual experience associated with an incentive spirometry device, a hot air balloon is flying over treetops and will only stay above the trees and collect party favors, gifts, animals, and/or the like if the user breaths at a correct pressure for a designated amount of time. Clearly numerous other examples could be listed here as well.

An example virtual experience in accordance with some embodiments of the present systems and methods is described below in connection with FIG. 34A through FIG. 40.

Figure 34A:
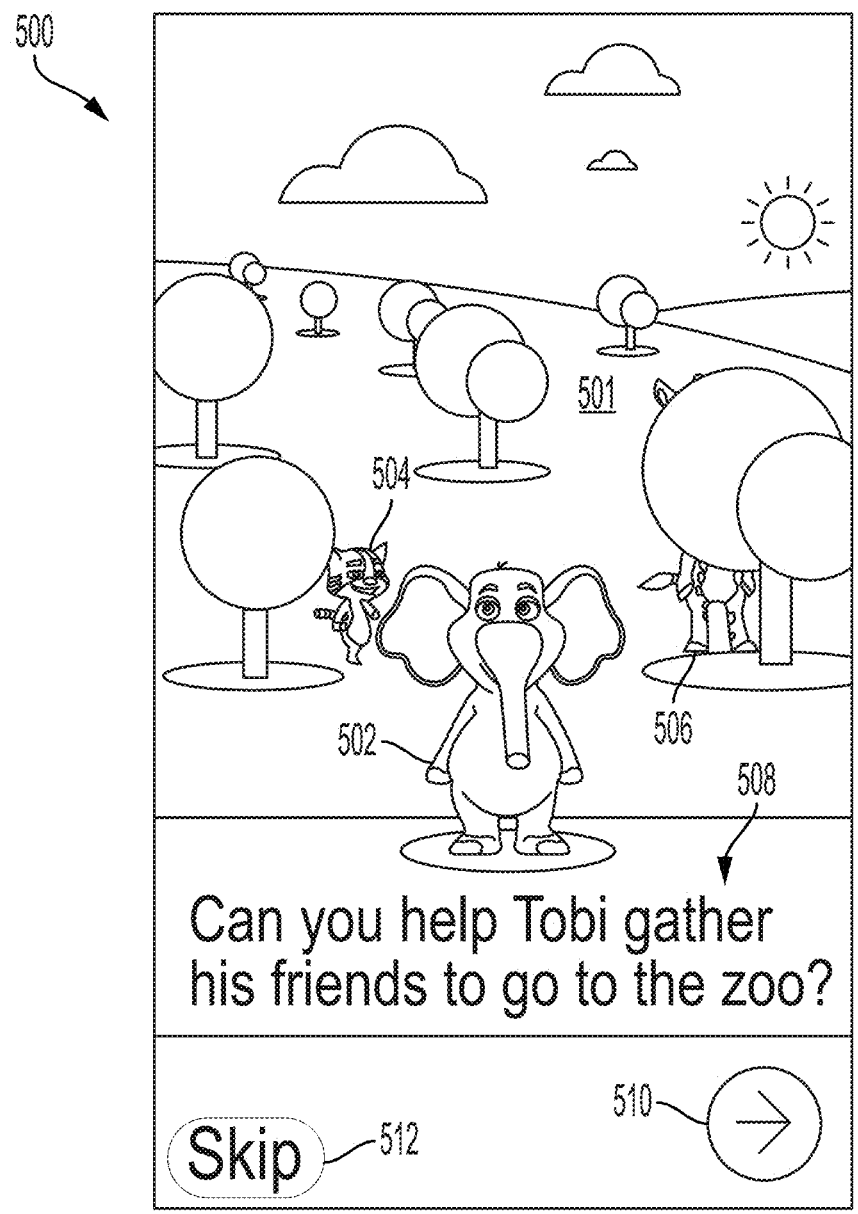
FIG. 34A is an illustrative storybook start screen, in accordance with at least one embodiment.

FIG. 34A depicts an illustrative storybook start screen 500 in which a message 508 reads "Can you help Tobi gather his friends to go to the zoo?" Standing on a landscape 501 is Tobi the elephant 502, and his friends include the cat 504 and the half-visible giraffe 506. Also displayed on the storybook start screen 500 is a skip button 512 and a next (i.e., right-pointing) arrow 510. In an embodiment, a storybook design facilitates parents and/or clinicians and/or older children that may be new to the present systems and methods product (or older children) to work through the various phases of the virtual experience without someone having to direct them. In at least one embodiment, this storybook start screen 500 can be skipped by selection of the skip button 512. When a user is ready, they can select the next arrow 510 to continue.

Figure 34B:
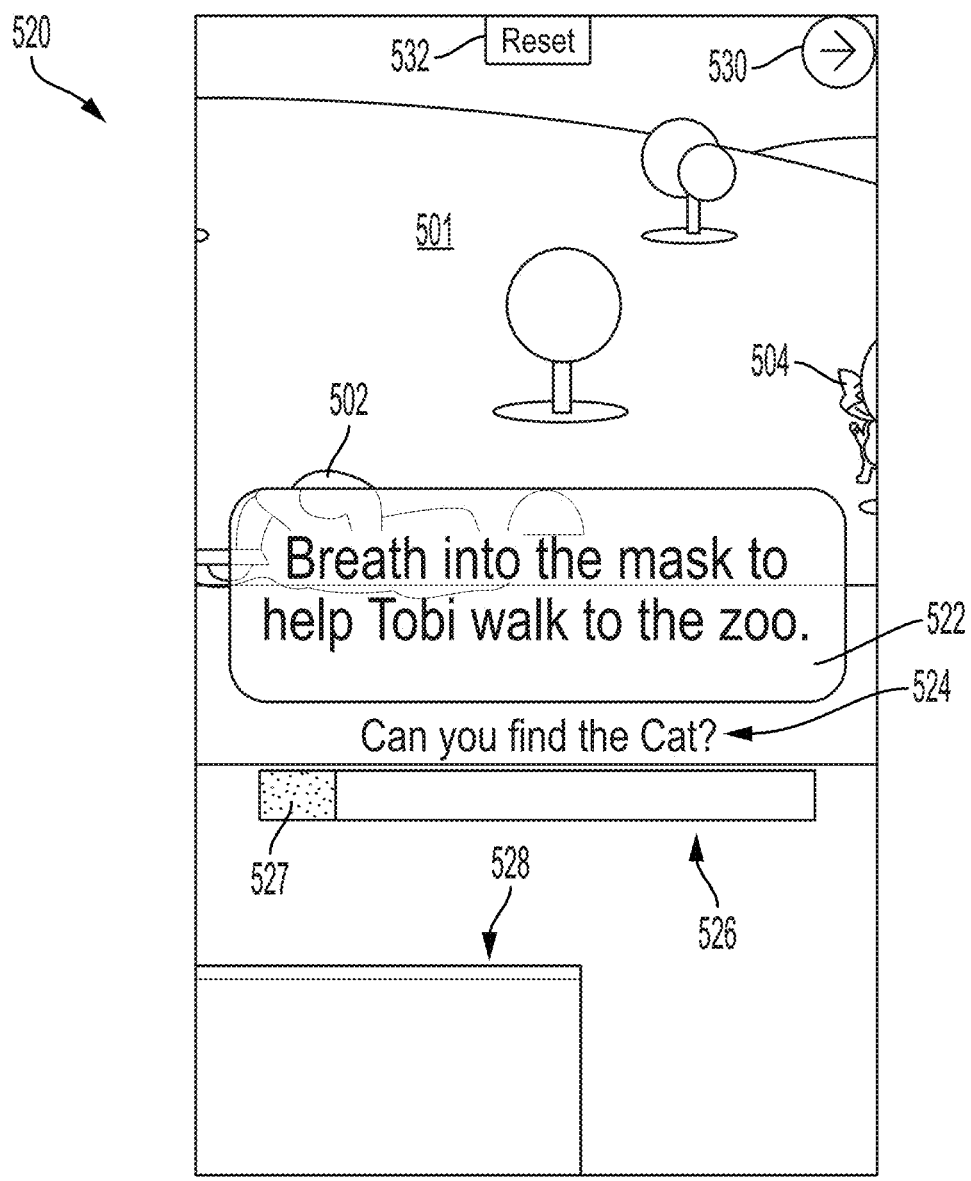
FIG. 34B is an illustrative walking-component screen of an illustrative respiration-device-acclimation phase in a respiration-controlled mode, in accordance with at least one embodiment.

FIG. 34B is an illustrative walking-component screen 520 of an illustrative respiration-device-acclimation phase in a respiration-controlled mode. It is noted that in describing FIG. 34B and the ensuing screenshot figures, elements that have been identified above (e.g., the landscape 501) are not unnecessarily mentioned repeatedly. The screen 520 includes a message 522 in the foreground that says, "Breath into the mask to help Tobi walk to the zoo." Depicted in the background of the screen 520 is Tobi the elephant 502 lying down, perhaps sleeping. Also depicted in the background is the cat 504 hiding behind a tree, a reset button 532 that is selectable in some embodiments to restart the respiration-device-acclimation stage of which the screen 520 is a part. Also depicted in the background are a next arrow 530, a message 524 that reads, "Can you find the Cat?", a status bar 526 having a level indicator 527 in a first color (e.g., orange), and graph 528, perhaps in a second color such as green, indicative of the current breathing or lack of breathing (due to, e.g., mask removal) being detected by the sensors 408.

In some embodiments, such as the one being presently described, the respiration-device-acclimation phase occurs as the first phase after an introductory screen such as the storybook start screen 500. In the respiration-device-acclimation phase, there may be two modes of operation: a respiration-controlled mode and an autoplay mode. When in the autoplay mode, which could be triggered manually and/or automatically (perhaps by detecting no breathing or insufficient breathing into the mask), the ongoing presentation of the virtual experience is independent of the user's contemporaneous respiration pattern. In many instances, in a pre-op phase, the autoplay mode is used in connections with patients that are not able to or having difficulty playing the game in a breath-controlled manner. Often this occurs with very young patients that are not yet old enough to follow game directions and/or take too small or weak of breaths to register with the sensors. In such cases, it is nevertheless advantageous to keep such patients engaged with the mask and the virtual experience, as this reinforces behaviors and actions that prove helpful in later phases of the game. When in the respiration-controlled mode, the virtual experience, such as the walking of the elephant 502, is controlled by the user's contemporaneous respiration pattern. In this example, insufficient breathing being detected via the mask while in the respiration-controlled mode has resulted in the elephant 502 laying down, perhaps to sleep, and autoplay mode to be activated, and the message 522 to appear to encourage the patient to breathe into the mask. Moreover, embodiments that stop gameplay or otherwise present feedback to encourage putting the mask back on inure to the benefit over the long term of health professionals that will thereby be exposed to and inhale lower cumulative amounts of anesthetic gasses.

Among the purposes of the respiration-device-acclimation phase in at least some embodiments is to get the patient used to simply having the mask on. Another purpose is to indicate to the system what a baseline level of breathing for that particular patient is, such that the system can then calibrate the game automatically to the patient's breathing pattern, perhaps in a calm environment. In some embodiments, as described below, this calibration is manually adjustable at one or more times during the presentation of the virtual experience. A baseline breathing pattern is then used in some embodiments to help guide the patient to try to replicate or at least closely approach that calm breathing pattern during a time of anxiety. In some instances, one or more of the phases are testable (i.e., playable) via a practice-type kiosk or other arrangement, perhaps with disposable straws or masks to breathe into, such that patients could practice at the doctor's office on a day prior to the surgery, and therefore get more comfortable with the entire system. A setup in a pre-op room could serve a similar purpose.

Figure 34C:
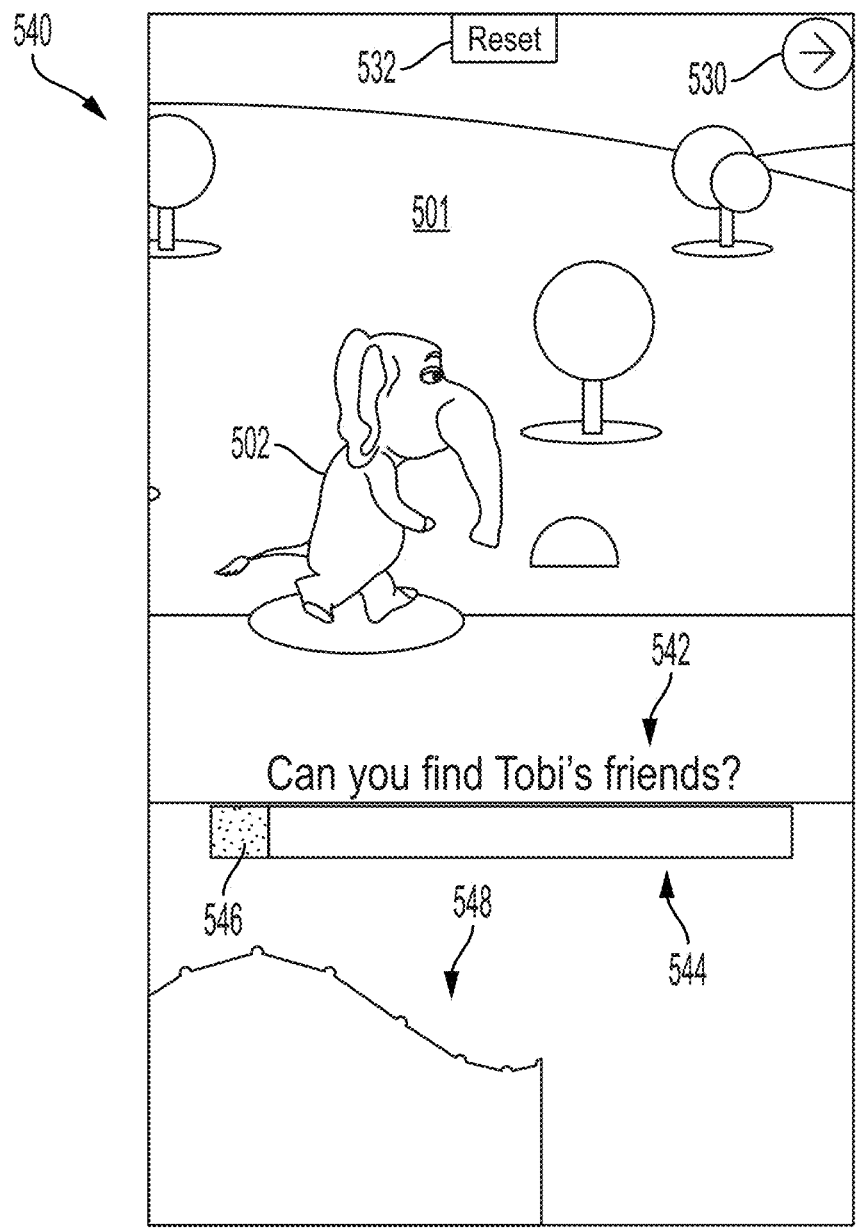
FIG. 34C is an illustrative walking-component screen of the illustrative respiration-device-acclimation phase in an autoplay mode, in accordance with at least one embodiment.

FIG. 34C is an illustrative walking-component screen of the illustrative respiration-device-acclimation phase in the autoplay mode. The system could switch from the respiration-controlled mode to the autoplay mode in response to a timeout period elapsing during which insufficient breathing is detected via the mask, or perhaps by a manual command via the touchscreen. In some embodiments, the status bar or other user-interface element is selectable so as to toggle between the autoplay mode and the respiration-controlled mode. In the screen 540 of FIG. 34C, with the system in the autoplay mode, the elephant 502 is walking at a pace that is independent of any breathing taking place via the mask. A status bar 544 is displayed having a level indicator 546 in a second color (e.g., green) that does not reflect any actual level of respiration. Similarly, the graph 548, which may also be green, shows an idealized curve reflective of simulated respiration data. A message 542 reads, "Can you find Tobi's friends?" The autoplay mode may help a patient get used to having the mask on, and the positive feedback presented on the screen may give the patient confidence that will serve them well in the phases still to come.

Figure 34D:
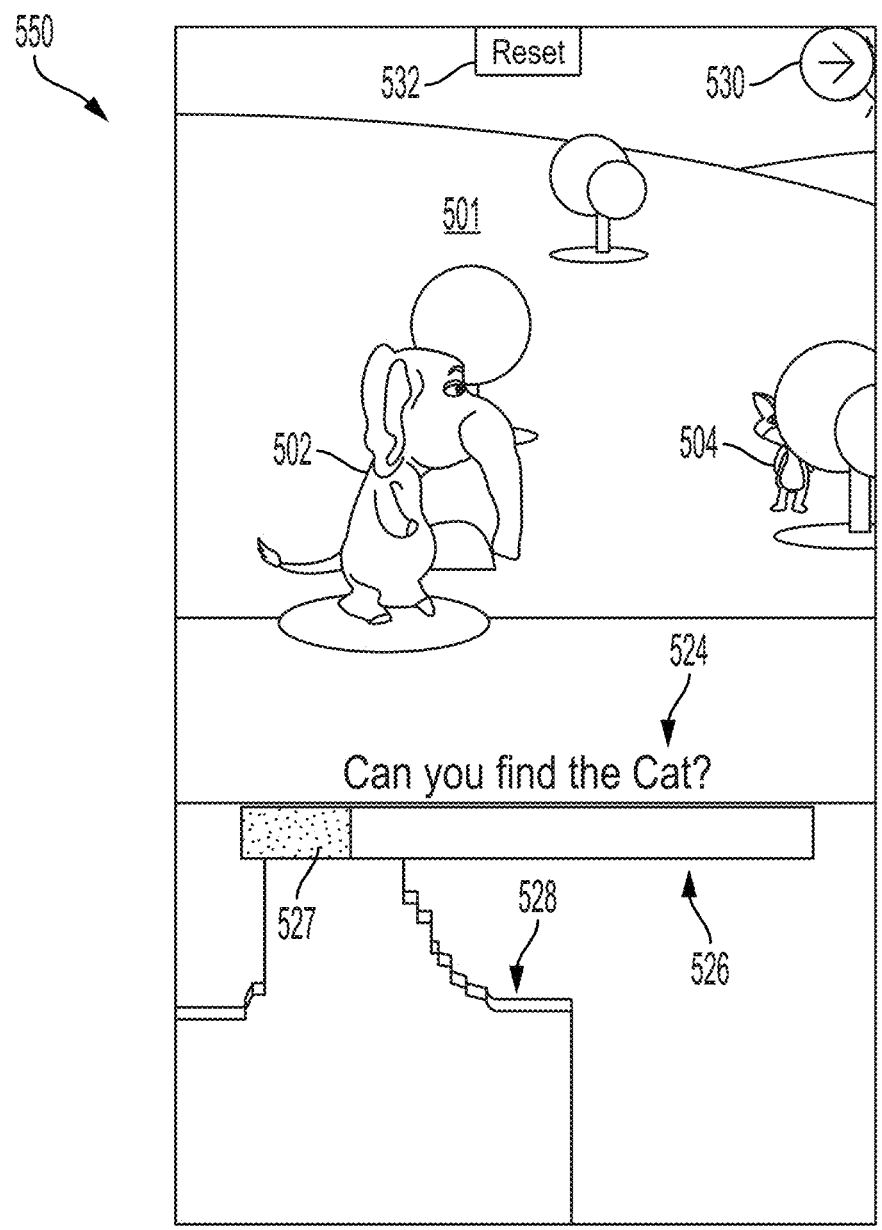
FIG. 34D is an illustrative walking-component screen of the illustrative respiration-device-acclimation phase in the respiration-controlled mode that shows an active-breathing curve, in accordance with at least one embodiment.

FIG. 34D is an illustrative walking-component screen 550 of the illustrative respiration-device-acclimation phase in the respiration-controlled mode that shows an active-breathing curve 528. In this example, the game was returned to the respiration-controlled mode, perhaps by tapping the status bar. Accordingly, the level indicator 527 in the first color (e.g., orange) is now shown on the status bar 526, and the graph 528 reflects actual breathing being detected via the mask.

Figure 34E:
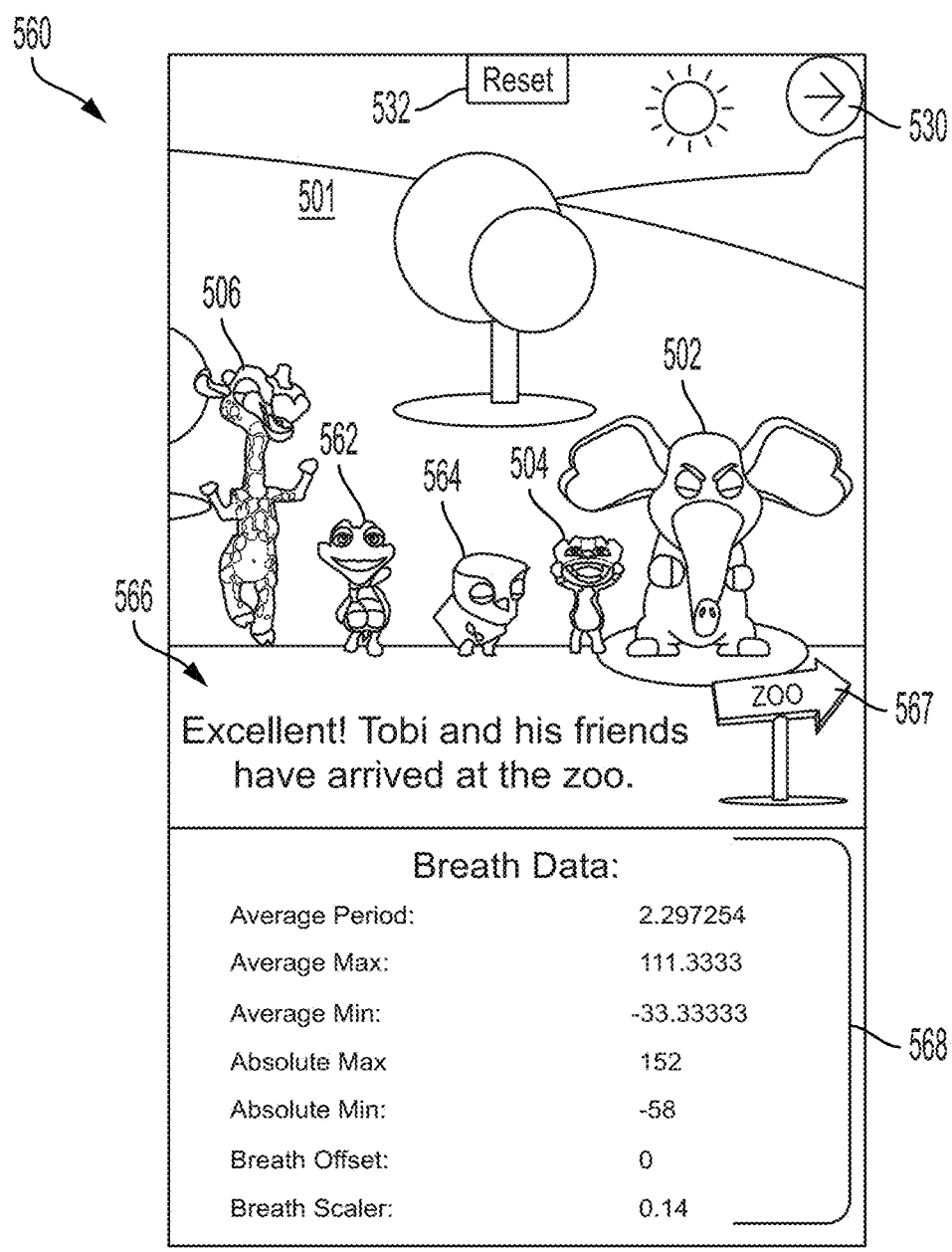
FIG. 34E is an illustrative end screen of the illustrative respiration-device-acclimation phase that shows illustrative breathing data during the illustrative respiration-device-acclimation phase, in accordance with at least one embodiment.

Perhaps entirely in the autoplay mode, perhaps entirely in the respiration-controlled mode, perhaps in some mixture of the two, the user reaches the end of the first phase—i.e., the respiration-device-acclimation phase, and is presented with the screen 560 that is shown in FIG. 34E. On the screen 560, the main character—i.e. Tobi the elephant 502 is show celebrating the arrival at the zoo with his friends the cat 504, the giraffe 506, a turtle 562, and an owl 564. A message 566 reads, "Excellent! Tobi and his friends have arrived at the zoo." This is further indicated by a "Zoo" sign 567.

Also shown on the screen 560 is a breath-data display 568 that includes illustrative values such as average period, average max, average min, absolute max, absolute min, breath offset (which in some embodiments is only shown in the case of an adjustment having been made to account for background pressure), and breath scaler (which is related to any automatic and/or manual calibration that was done with respect to breath sensitivity). In various embodiments, displays of breath data are shown at the end of one or more phases and/or are viewable at any time using a gesture such as a swipe up from the bottom of the screen. is an illustrative end screen of the illustrative respiration-device-acclimation phase that shows illustrative breathing data during the illustrative respiration-device-acclimation phase, in accordance with at least one embodiment.

Figure 35:
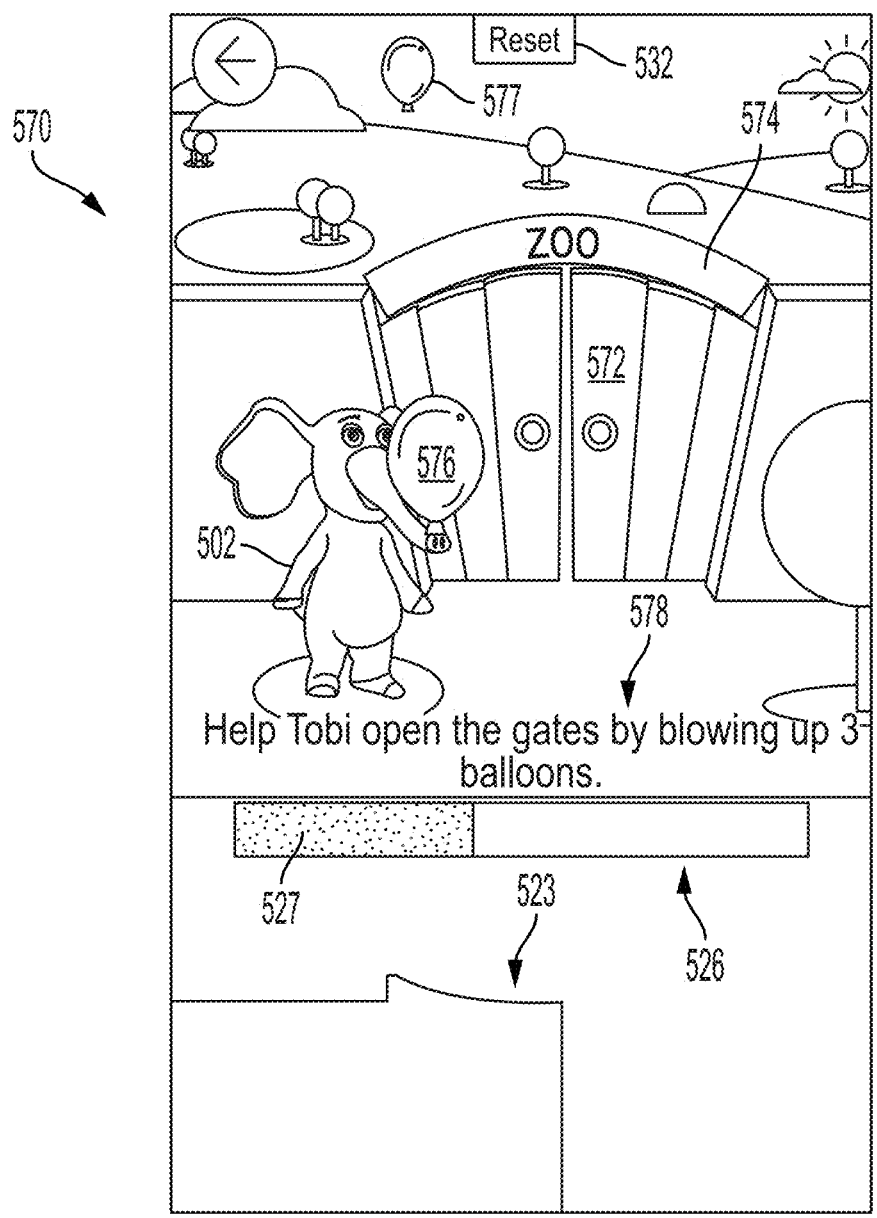
FIG. 35 is an illustrative start screen of an illustrative balloon-blowing-up game of an illustrative exhalation-validation phase, in accordance with at least one embodiment.

In this example, the user next proceeds to what is referred to herein as an exhalation-validation phase, described now with reference to FIG. 35 in the context of an illustrative balloon-blowing-up game. Indeed, FIG. 35 shows an exhalation-validation-phase start screen 570 that includes the elephant 502 blowing up a first balloon 576 in front of a gate 572 having a "Zoo" sign 574 marking the entrance to the virtual zoo. Also depicted is a balloon 577 that is already floating over the zoo, as well as a message 578 that reads, "Help Tobi open the gates by blowing up 3 balloons." Further depicted is the respiration-controlled status bar 526 having the level indicator 527, as well as the graph 528 that is reflective of actual breathing being detected via the mask by the controller. In at least one embodiment, in the exhalation-validation phase, feedback is presented via the user interface to reflect the degree to which one or more respiration parameters measured via the respiration device meet or exceed corresponding thresholds.

In at least one embodiment, among the purposes of the exhalation-validation phase is to assist the patient in learning to actually exhale into the mask with sufficient strength and/or sufficient duration. In this phase, then, the patient gets used to exhaling into the mask, and the exhalations of the patient control the occurrence of positive feedback on the screen (and in some embodiments negative feedback (e.g., encouraging the patient to try again)). In an embodiment, there are 3 balloons to blow up-once each balloon is inflated, it drifts up into the air before the next balloon is shown, to encourage the child to pause between the balloons (and not continually take large and fast breaths).

Figure 36A:
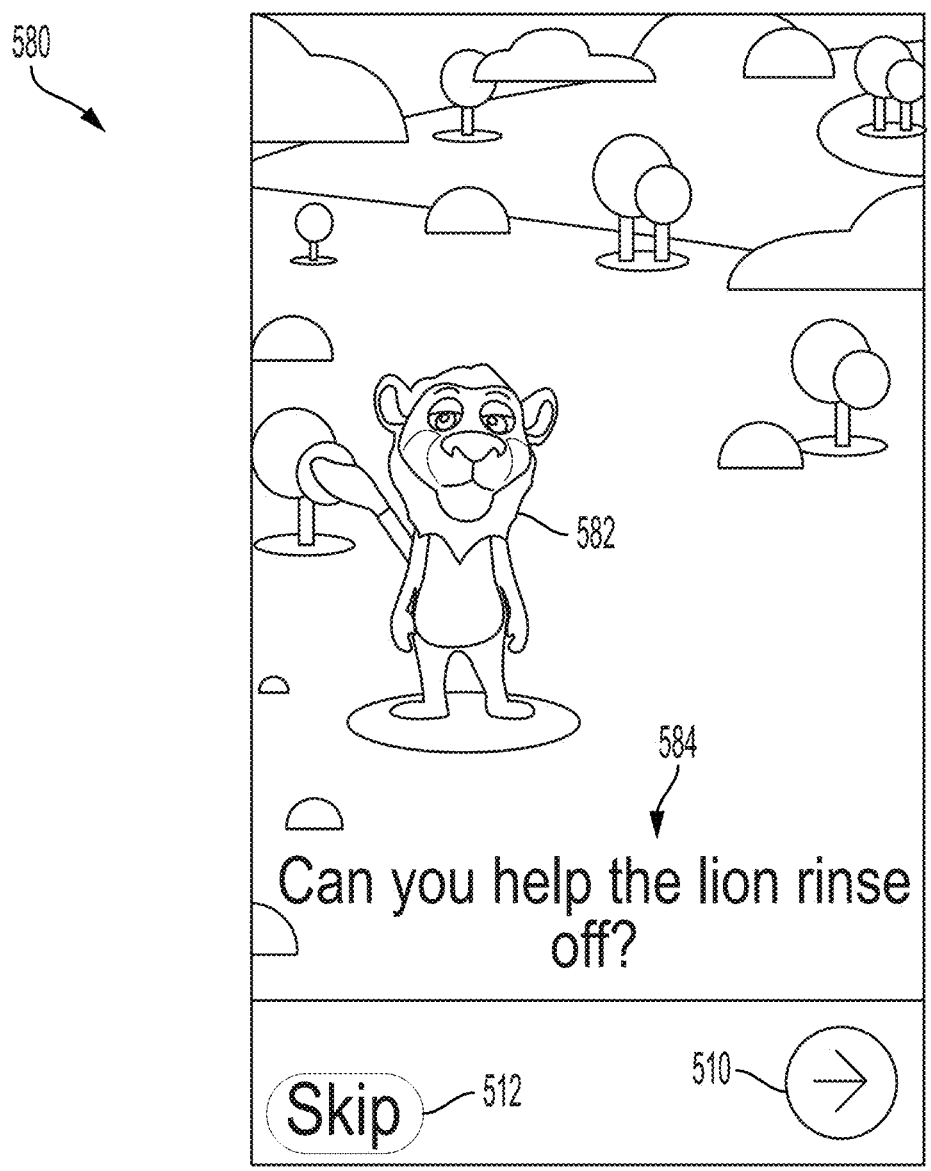
FIG. 36A is an illustrative start screen of an illustrative animal-washing game of an illustrative breathing-pattern phase, in accordance with at least one embodiment.

Upon completing the exhalation-validation phase, in at least one embodiment the user proceeds next to what is referred to herein as a breathing-pattern phase, an example of which is now described with initial reference to FIG. 36A, which depicts an illustrative start screen 580 of an illustrative animal-washing game of an illustrative breathing-pattern phase. In at least one embodiment, among the aims of the breathing-pattern phase is to get the patient used to breathing in a predefined rhythm into the mask. As such, in at least one embodiment, while in the breathing-pattern phase, the rhythmic nature of the patient's breathing contributes to whether positive or negative (e.g., try again) feedback is presented via the user interface. It is among the goals of the breathing-pattern phase to help patients such as children learn to and practice how to breath slowly and calmly, which may reduce their anxiety and which is effective for induction of anesthesia. The patient is helped by virtue of the breathing-pattern phase to learn to exhale according to an acceptable breathing pattern, which relates to sub-characteristics including breathing rate or rhythm, strength, duration, and/or the like.

An example breathing-pattern phase is described above in connection with drying off a lion. The example breathing-pattern phase that is described here involves cleaning off or rinsing off a lion. Other examples of rhythmic virtual experiences that are amenable to the breathing-pattern phase include rowing, speedskating, playing a musical instrument (e.g., the drums), and innumerable others that could be listed here. On the screen 580, a lion 582 is shown, as well as a message that reads, "Can you help the lion rinse off?"

Figure 36B:
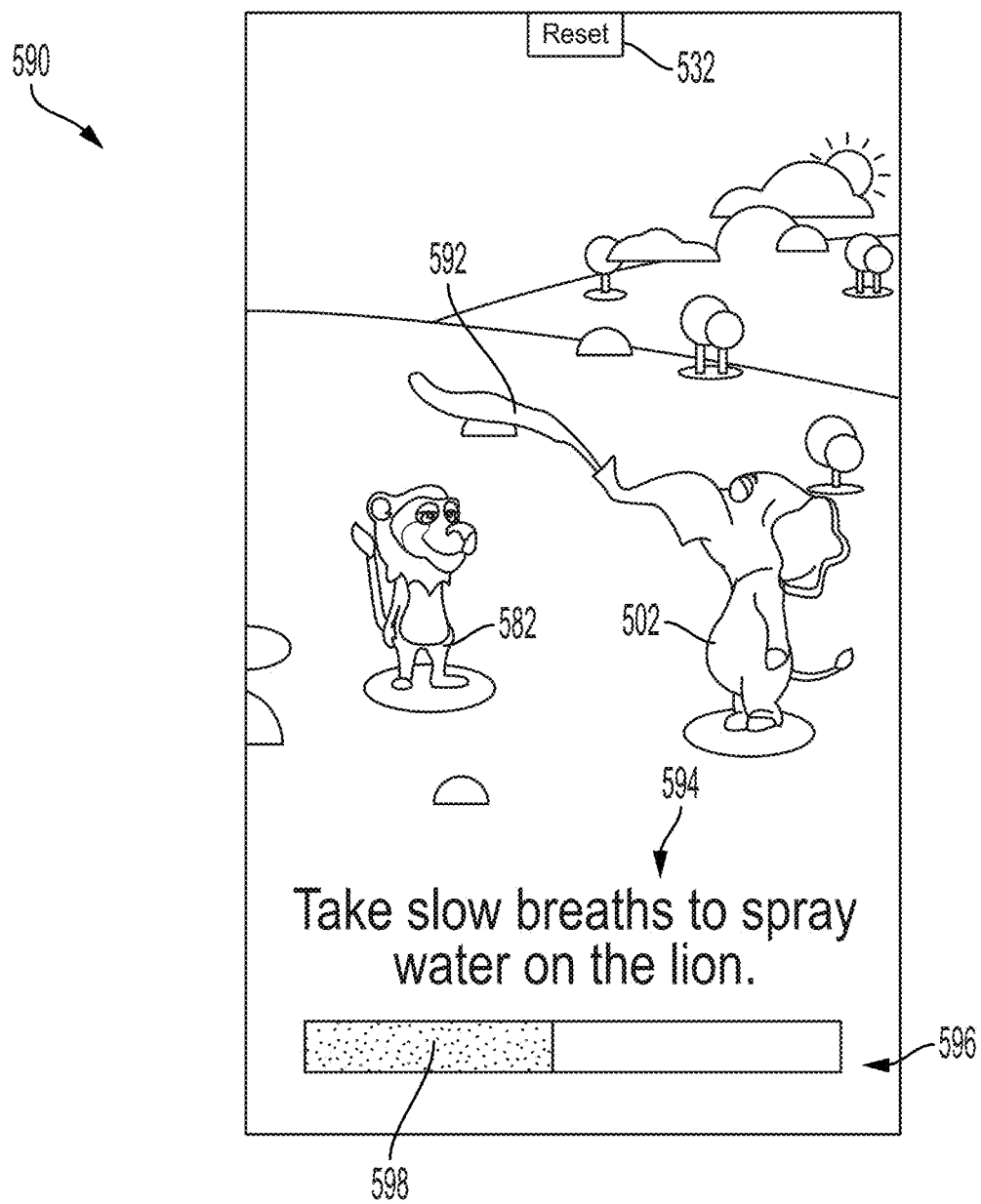
FIG. 36B is an illustrative first gameplay screen of the illustrative animal-washing game of the illustrative breathing-pattern phase, in accordance with at least one embodiment.
Figure 36C:
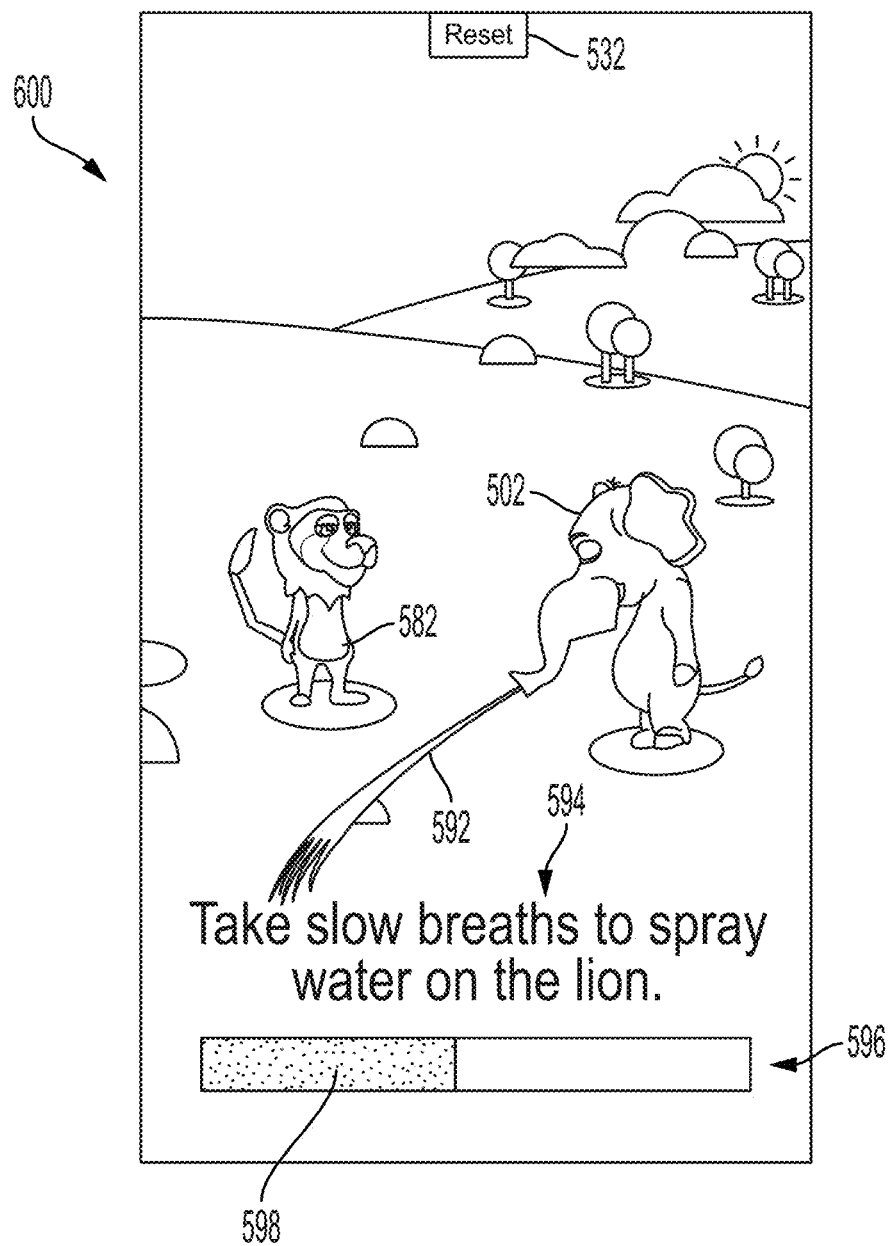
FIG. 36C is an illustrative second gameplay screen of the illustrative animal-washing game of the illustrative breathing-pattern phase, in accordance with at least one embodiment.
Figure 36D:
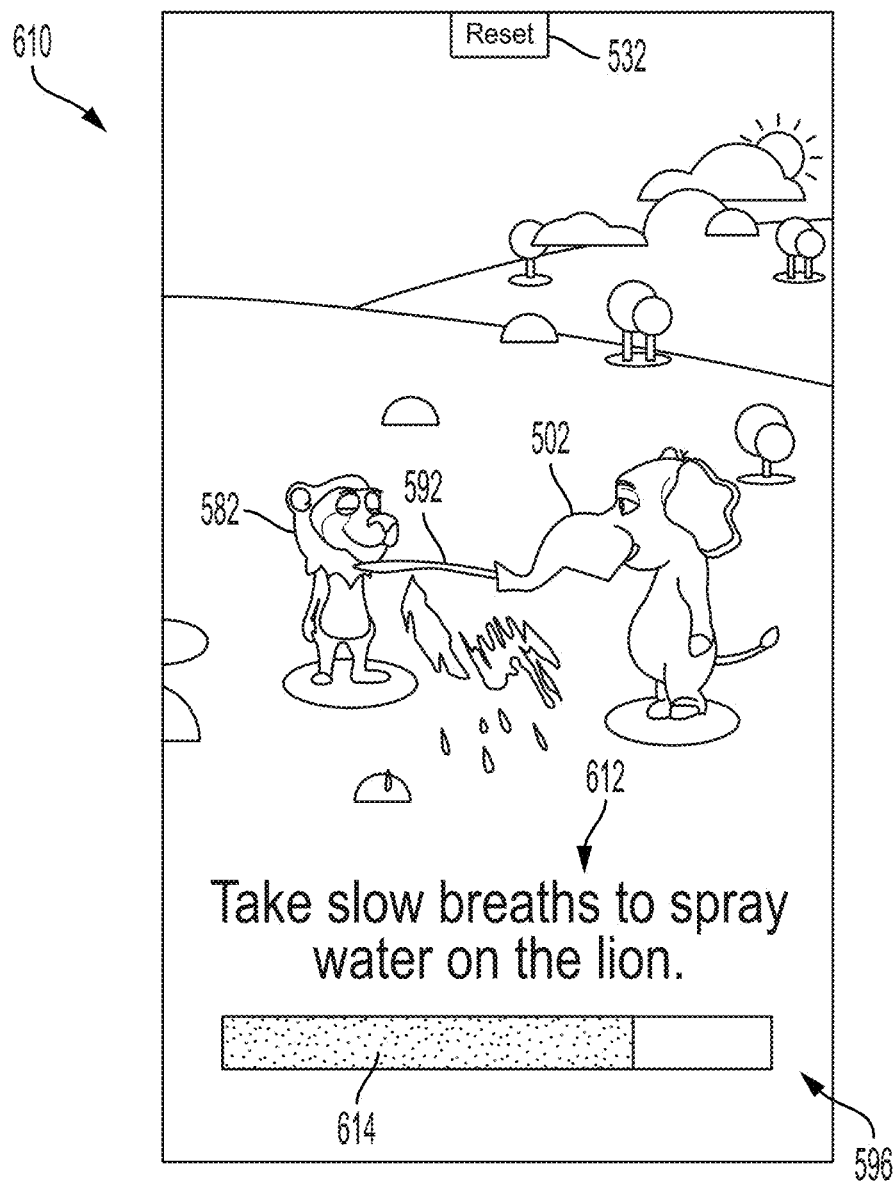
FIG. 36D is an illustrative second gameplay screen of the illustrative animal-washing game of the illustrative breathing-pattern phase, in accordance with at least one embodiment.

In this example, the user proceeds next to the screen 590 as shown in FIG. 36B. On the screen 590, a message 594 reads, "Take slow breaths to spray water on the lion." Also depicted on the screen 590 is a status bar 596 with a level indicator 598. The elephant 502 is positioned to the right of the lion 582, and the elephant 502 is using its truck to spray a water stream 592 in the general direction of the lion 582. In an embodiment, breaths that are too fast and/or different from a desirable value with respect to one or more other respiration parameters result in the water stream 592 being either too high or too low to properly rinse off the lion 582. In the example shown in the screen 590, the water stream 592 is too high. In the screen 600 that is depicted in FIG. 36C, the water stream 592 is too low. In the screen 610 that is depicted in FIG. 36D, the water stream is just right, indicating that the breathing pattern matches the target breathing pattern within an acceptable margin, tolerance, or the like.

In some embodiments, the breathing-pattern phase involves presenting both an actual breathing pattern and a predefined (i.e., acceptable or target) breathing pattern via the user interface. FIG. 24A shows an example of that type of display, where a sinusoidal breathing pattern 338 is presented as a target for a user to attempt to match with actual breathing, the pattern of which is reflected in the graph 340.

Figure 37:
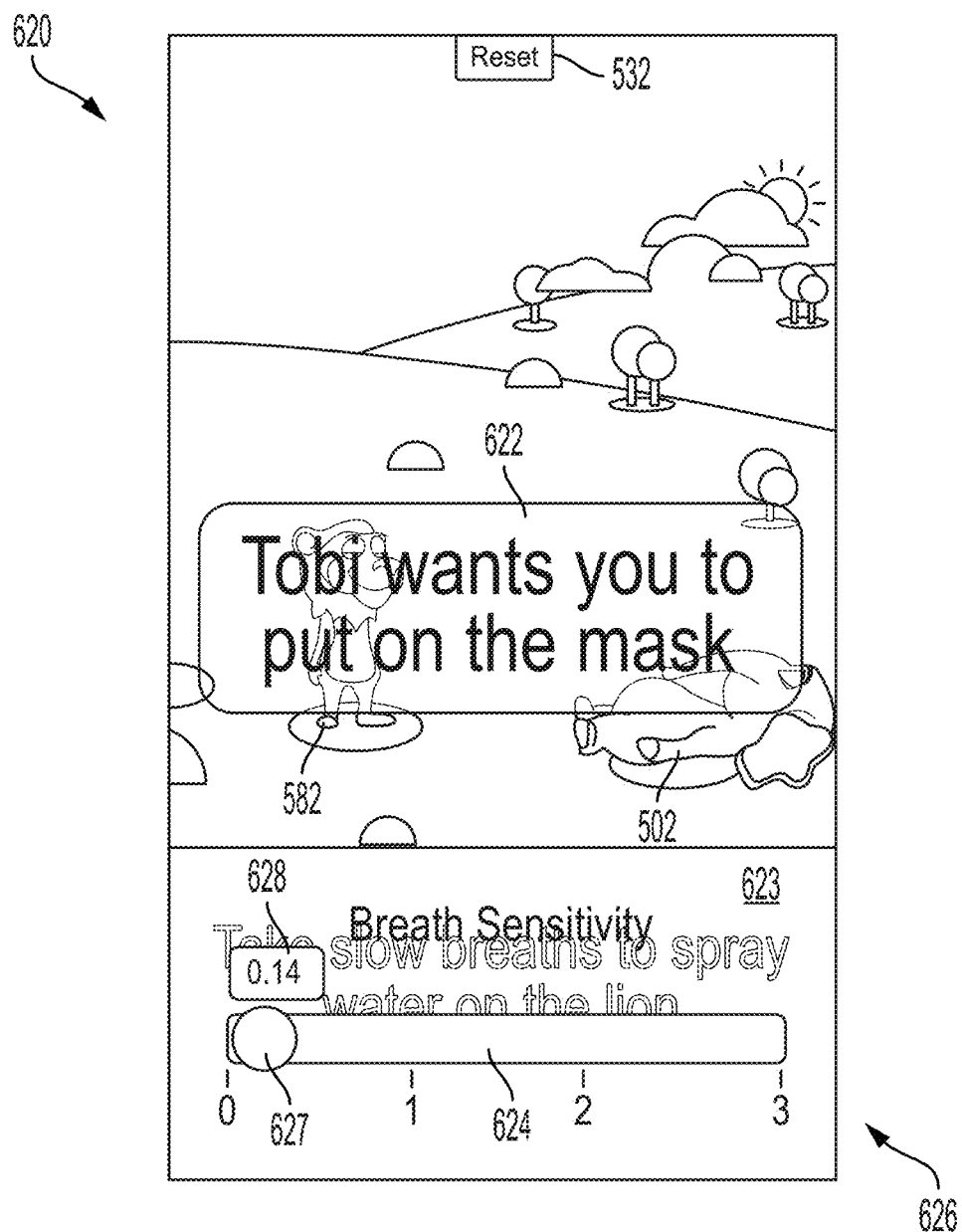
FIG. 37 is an illustrative breath-sensitivity manual adjustment screen, in accordance with at least one embodiment.

FIG. 37 depicts a screen 620, which is similar to the screen 520 of FIG. 34B in that insufficient breathing being detected via the mask has resulted in most of the normally foreground elements being displayed in the background and a message 622 being displayed in the foreground and reading "Tobi wants to you put on the mask." Unlike the screen 520 of FIG. 34B, however, screen 620 of FIG. 37 displays a dialog 623 that is operable to manually calibrate a breath-sensitivity level of the system. In some embodiments, the dialog 623 is displayable using a gesture such as swiping up from the bottom or one side or the other, as examples. The dialog 623 includes a slider 627 that is movable on a slider bar 624 to adjust a breath-sensitivity scaling factor within a range 626 that spans from 0 to 3, inclusive.

In an embodiment, 0 corresponds to not scaling at all, whereas any number above 0 corresponds to scaling breath measurements up by the sum of 1 and the selected value. In the example shown in FIG. 37, then, the scaling factor would be 1.14. Other implementations are certainly possible as well, including the scaling factor simply being equal to what is selected along the slider, such that no scaling would correspond to a 1 on the slider bar 624, less than one would involve scaling down, and greater than 1 would involve scaling up. And certainly many other implementations are possible as well. In various different embodiments, a breath-sensitivity level is manually adjustable during one or more of the sequential phases.

In some embodiments, the option to manually adjust the breath-sensitivity level complements an automatic calibration process that occurs. In some embodiments, a breath-sensitivity level is saved during an earlier training session with a patient and retrieved for implementation during the lead-up to, e.g., an anesthesia induction. In some embodiments, a breath-sensitivity level is adjustable from a device other than one with which the patient is interacting. For example, a nurse could have a smartphone connected via Bluetooth or Wi-Fi and be able to manually configure a breath-sensitivity level and/or one or more other parameters via that other device.

Figure 38A:
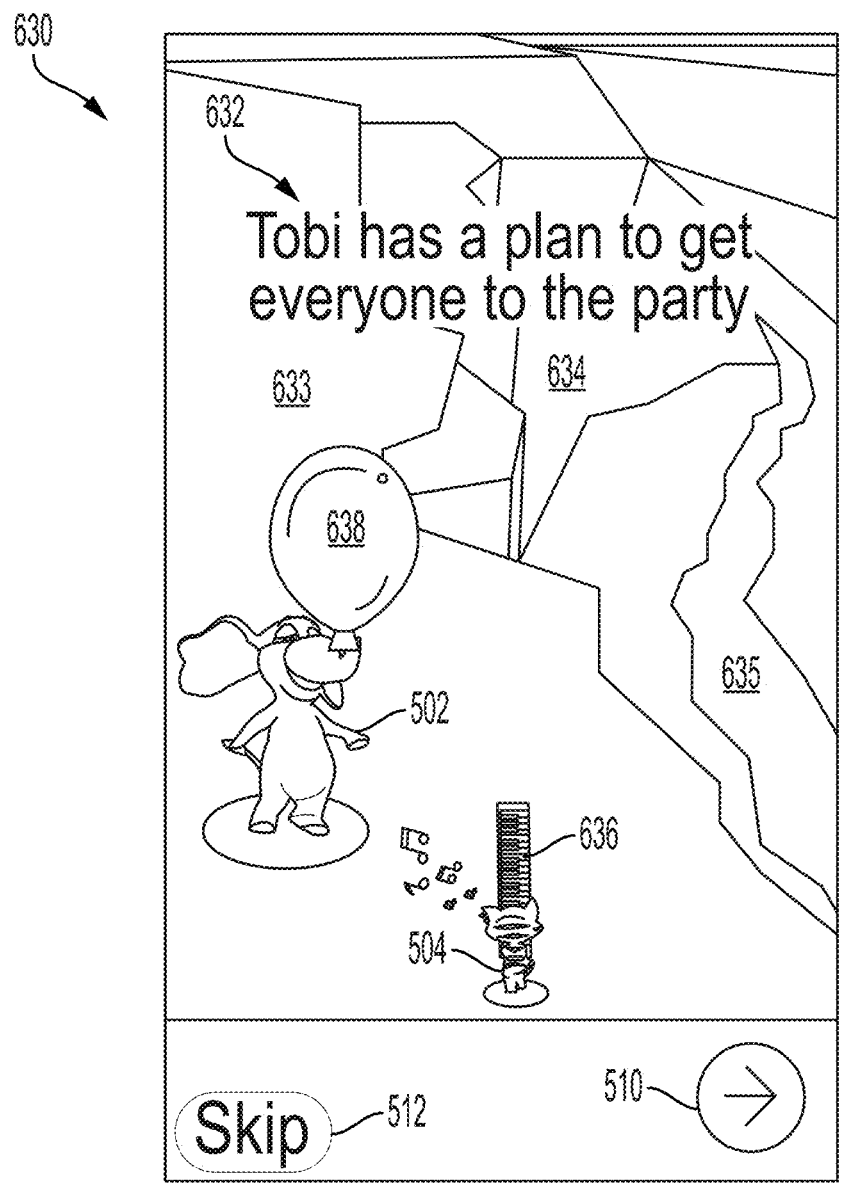
FIG. 38A is an illustrative start screen of an illustrative canyon-crossing game of an illustrative active-induction phase, in accordance with at least one embodiment.

After completing the breathing-pattern phase, in at least one embodiment the patient proceeds immediately to what is referred to herein as an active-induction phase, which is described now with initial reference to FIG. 38A, which depicts an illustrative start screen 630 of an illustrative canyon-crossing game of an illustrative active-induction phase. In at least one embodiment, the active-induction phase corresponds in time with the patient actually receiving anesthetic induction. Similar to the above-described breathing-pattern phase, in at least one embodiment the active-induction phase rewards (with positive user-interface feedback) depth and rhythm of breathing that correspond with a predefined pattern. In some embodiments, deviation by a sufficient amount from the predefined pattern results in negative feedback (try again) being presented.

As shown in FIG. 38A, the screen 630 includes a message 632 that reads "Tobi has a plan to get everyone to the party." Also depicted is a near side 633 of a canyon 634 having a river 635 running through it. Further, the cat 504 is depicted playing a musical instrument 636. The elephant 502 is depicted with a balloon 638.

Figure 38B:
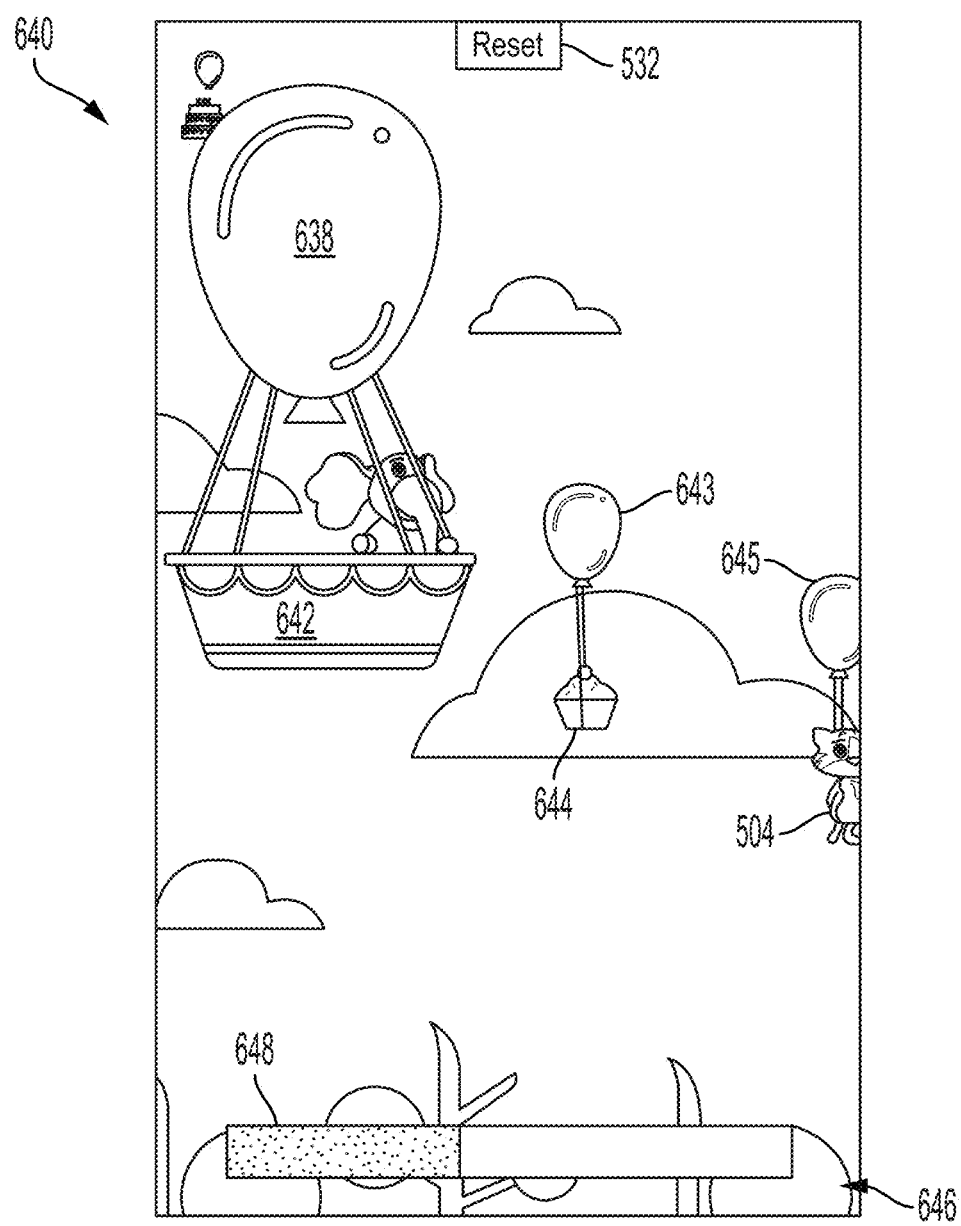
FIG. 38B is an illustrative first gameplay screen of the illustrative canyon-crossing game of the illustrative active-induction phase, in accordance with at least one embodiment.

After the start screen 630, the user proceeds next to the screen 640, which is depicted in FIG. 38B. Now, the elephant 502 is riding in a basket 642 that is supported by the balloon 638. Also depicted is a balloon 643 supporting a dessert 644 and a balloon 645 supporting the cat 504. Further, a status bar 646 having a level indicator 648 provides real-time feedback to the user regarding their current breathing parameters. It is noted that the balloon 638 is at a higher altitude than the balloon 643, which in turn is at a higher altitude than the balloon 645. In an embodiment, this arrangement is designed to coach and coax the user into breathing according to a predefined pattern, where the left-to-right arrangement of the balloons in the screen 640 corresponds with a decreasing part of an idealized sinusoidal breathing pattern. Positioning prizes and friends higher up in an ensuing part of the virtual sky coaxes the user into breathing according to a rising portion of that idealized sinusoid.

Figure 38C:
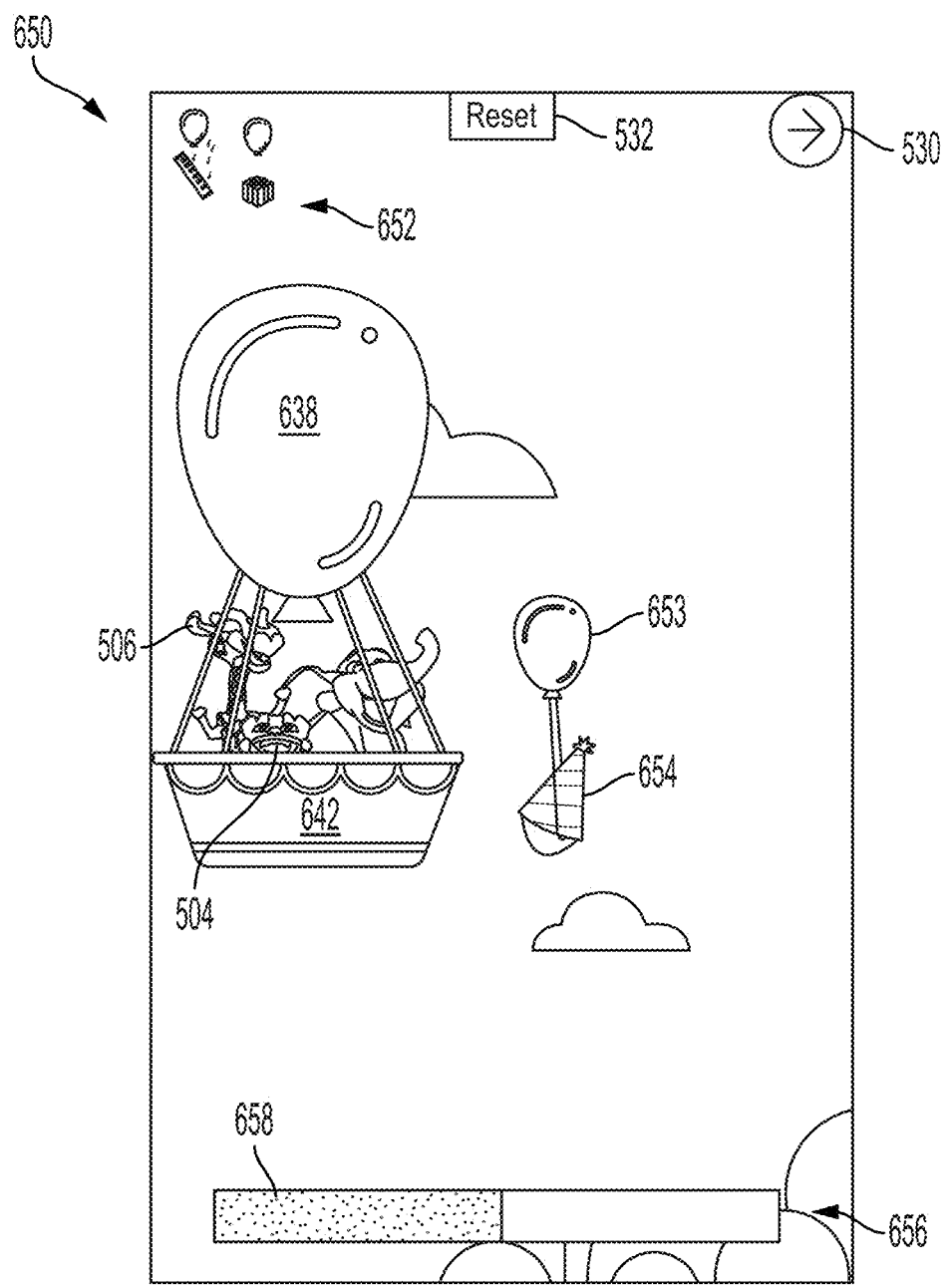
FIG. 38C is an illustrative second gameplay screen of the illustrative canyon-crossing game of the illustrative active-induction phase, in accordance with at least one embodiment.

The user may then proceed to a screen such as the screen 650 that is shown in FIG. 38C. In the screen 650, the elephant 502 has added the cat 504 and the giraffe 506 to the basket 642, and is closing in on a balloon 653 that is supporting a party hat 654. In an embodiment, the status bar 656 as a level indicator 658 that has turned a positive color (e.g., green), which could indicate autoplay mode has been engaged, but in some embodiments indicates that the user is breathing right on pattern, a situation that may also be reflected in some embodiments by the elephant 502 being at approximately the same altitude as the party hat 654. Also depicted is a tally 652 of prizes and/or friends already collected by the player. In at least one embodiment, fast breathing does not make the balloon 638 move faster; rather, it is slow, calm breaths that move the balloon 638 closer to favors, friends, and/or the like, to encourage calm breaths.

Figure 38D:
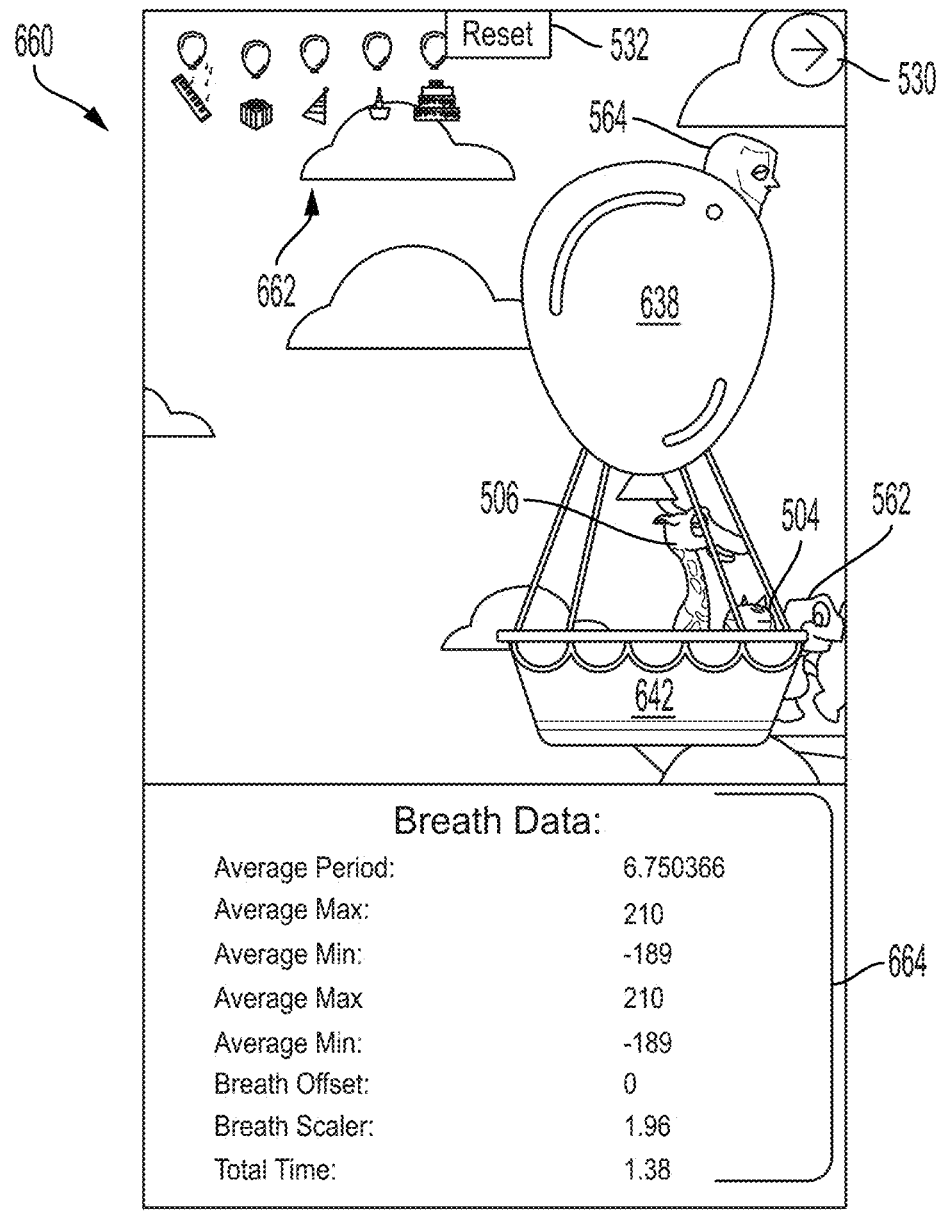
FIG. 38D is an illustrative third gameplay screen of the illustrative canyon-crossing game of the illustrative active-induction phase showing breath data, in accordance with at least one embodiment.

The user may then proceed to a screen such as the screen 660 that is depicted in FIG. 38D. In the screen 660, the tally 662 shows even more prizes collected, and the balloon 638 has now been joined by the owl 564. It can also be seen that the basket 642 is approaching the far side of the canyon 634. In some embodiments, the active-induction phase proceeds endlessly (e.g., the user keeps collecting friends and prizes but never reaches the other side of the canyon 634). In other embodiments, the active-induction phase proceeds endlessly but in a repeating fashion (e.g., the user makes multiple successful trips across the canyon 634). The active-induction phase may continue until manually shut off (perhaps on the device the patient was using, perhaps remotely from another device) by a healthcare professional once the patient is unconscious, until some time period expires, until one or more biometric parameters indicate that the patient is unconscious, and/or until one or more other triggering events occur.

In some embodiments, during the active-induction phase, a respiration-data spike is detected that corresponds to the introduction of a certain anesthetic gas such as sevoflurane, and that data spike is responsively filtered out of the presentation of the virtual experience. The screen 660 in FIG. 38D shows another example of a breath-data display, this time the breath-data display 664. An additional parameter, total time to induction, is displayed in the breath-data display 664. As a general matter, calm breathing with a good mask seal may facilitate faster induction time and less chronic exposure of the anesthetist to potentially harmful anesthesia gases.

Figure 39:
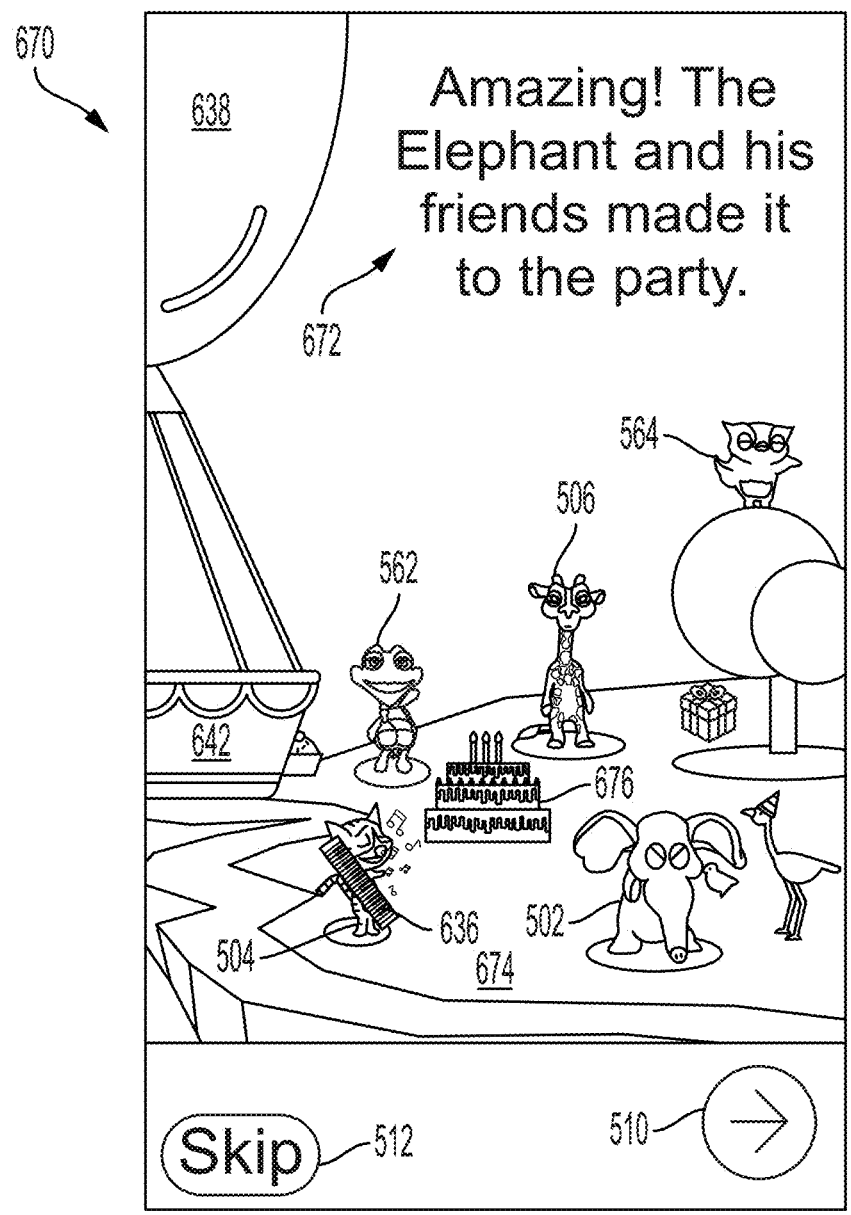
FIG. 39 is an illustrative end screen of the illustrative canyon-crossing game of an illustrative post-operative phase, in accordance with at least one embodiment.

In some embodiments, a post-operative phase is included. FIG. 39 depicts an example end screen 670 of the illustrative canyon-crossing game of an illustrative post-operative phase. On the screen 670, a message 672 reads, "Amazing! The Elephant and his friends made it to the party." Also displayed are the elephant 502, the cat 504 playing the instrument 636, the giraffe 506, the owl 564, the turtle 562, and a cake 676, all on the far side 674 of the canyon 534. In some embodiments, this scene may echo a scene shown to the child prior to induction, perhaps as a distraction while the medical team is prepping for the induction.

Figure 40:
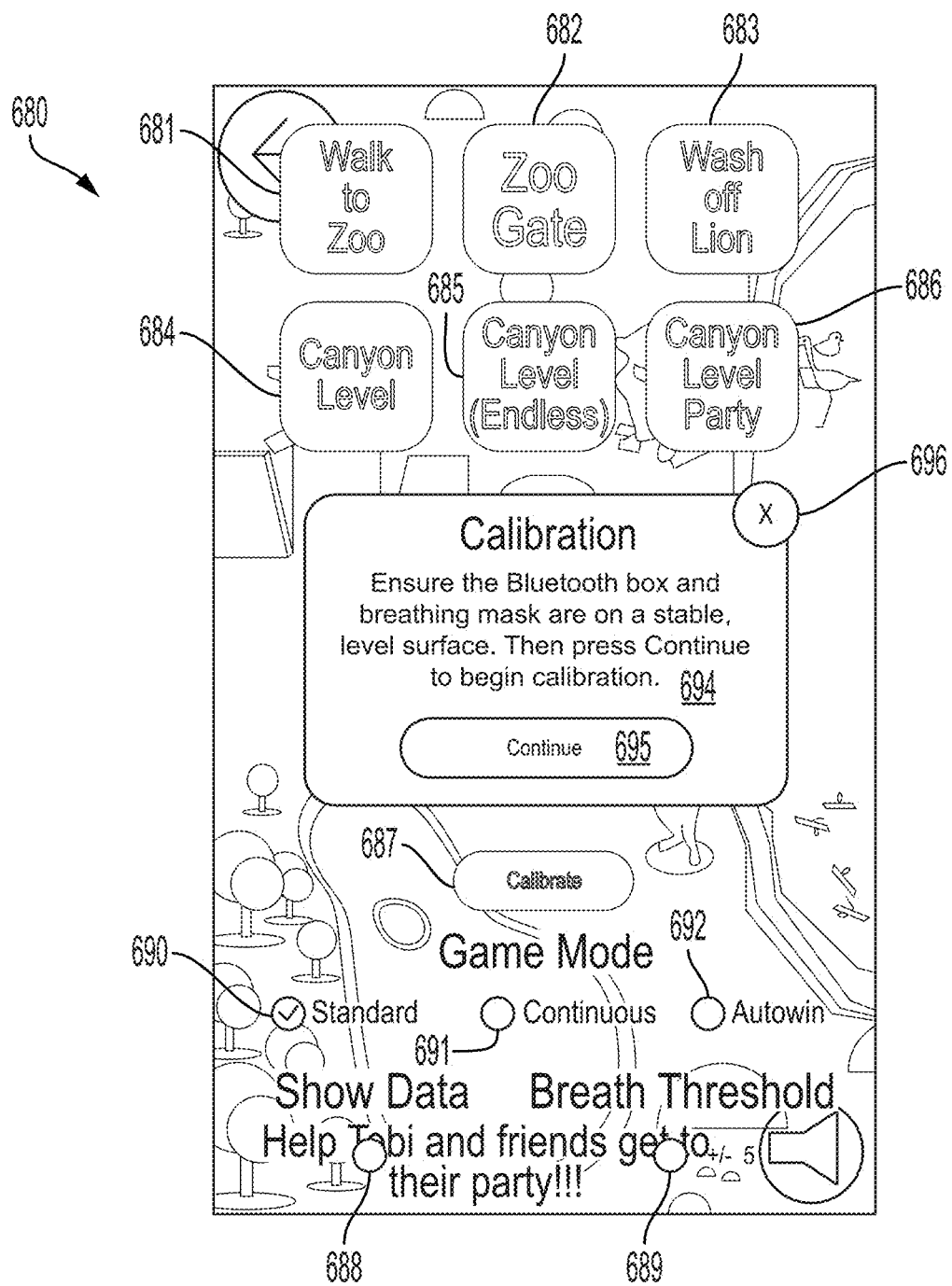
FIG. 40 is an illustrative main-menu screen showing an illustrative calibration dialog, in accordance with at least one embodiment.

FIG. 40 depicts an illustrative main-menu screen 680 showing an illustrative calibration dialog 694. Depicted in the screen 680 are a shortcut button 681 to the respiration-device-acclimation phase (Walk to Zoo), a shortcut button 682 to the exhalation-validation phase (Zoo Gate) a shortcut button 683 to the breathing-pattern phase (Wash off Lion), a shortcut button 684 to play a finite version of the active-induction phase (Canyon Level), a shortcut button 685 to play the non-finite version of the active-induction phase (Canyon Level (Endless)), and a shortcut button 686 to the post-operative phase (Canyon Level Party). Further depicted are game-mode selection radio buttons 690 (Standard), 691 (Continuous), and 692 (Autowin), as well as a Show Data button 688 and a Breath Threshold button 689, in accordance with at least one embodiment. In an embodiment, the Show Data button 688 is selectable to show real-time pressure data while the game is being played. In an embodiment, the main menu of the screen 680 is viewable via a gesture such as swiping down from the top. Also depicted is a Calibrate button 687, which in the screen 680 has been selected to display the calibration dialog 694, which can be closed using the "X" 696, or instead the user can select a Continue button to proceed to calibrating the breath-sensitivity level or perhaps to zero out background pressure in an application such as a CPAP application.

Figure 41:
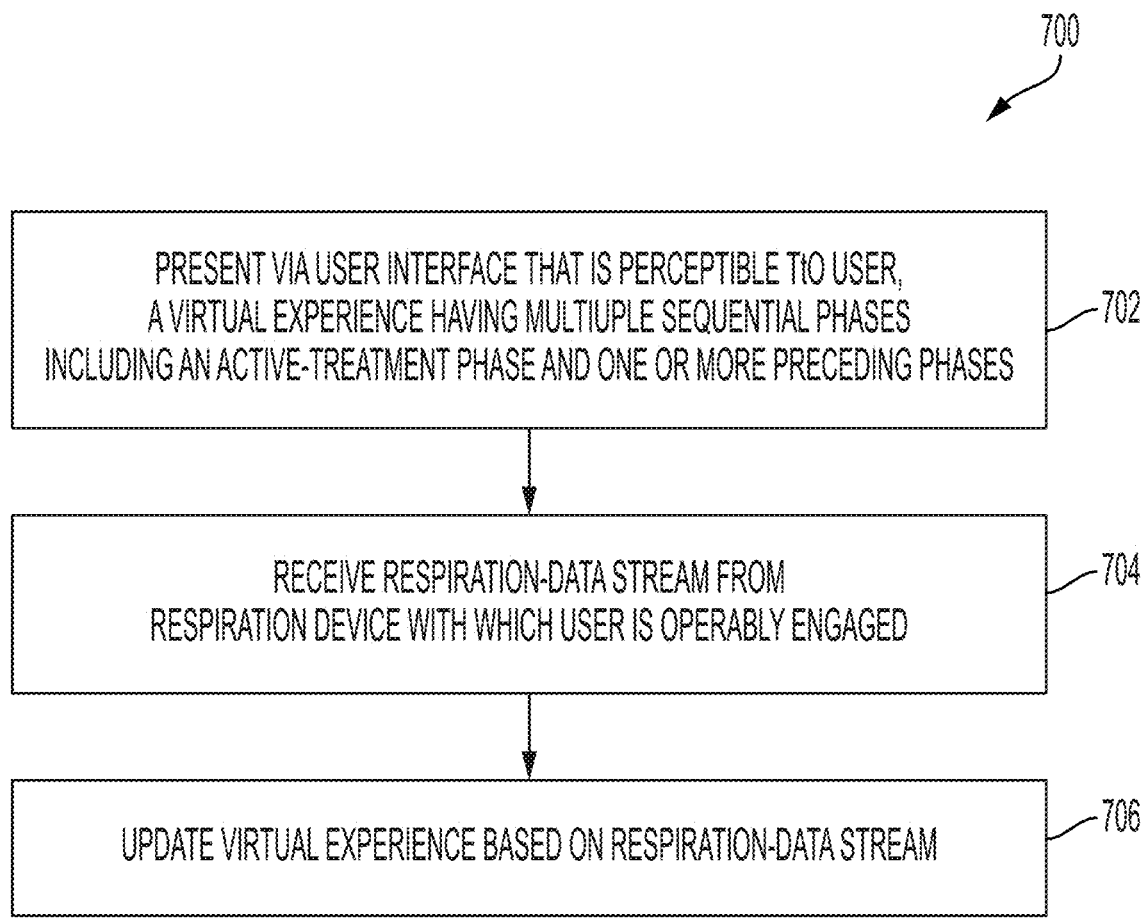
FIG. 41 is an illustrative flowchart of a second illustrative method, in accordance with at least one embodiment.

FIG. 41 is an illustrative flowchart of a method 700, in accordance with at least one embodiment. The method 700 is quite similar to the method 430 and is therefore not described herein in as much detail. Instead of an active-induction phase that pertains to active induction of anesthesia, the method 700 involves what is referred to herein as an active-treatment phase, which, as described above, could include receiving one or more medicaments and/or one or more form of medical treatment and/or simply interacting with a respiration device, in some cases at the direction or according to the instructions provided by a medical professional or other person, or perhaps at the direction or according to instructions provided from a computerized source such an interactive virtual experience as described herein on an app executing on a device provided by a medical-care facility or perhaps a device associated with (e.g., owned) by the particular patient. The respiration device could be any of the types of respiration devices mentioned herein and/or any other type of respiration device deemed suitable by those of skill in the art in a given context or for a given implementation. In any embodiment, breathing could be detected using abdomen belts, pressure sensors, microphones, and/or any other equipment deemed suitable by those of skill in the relevant art for collecting data reflective of ongoing respiration. In the case of the respiration device being or including (or being included in) a nebulizer, the taking of deep breaths and the keeping on of the mask for certain durations is rewarded in at least one embodiment with positive feedback via one or more user interfaces.

Figure 42:
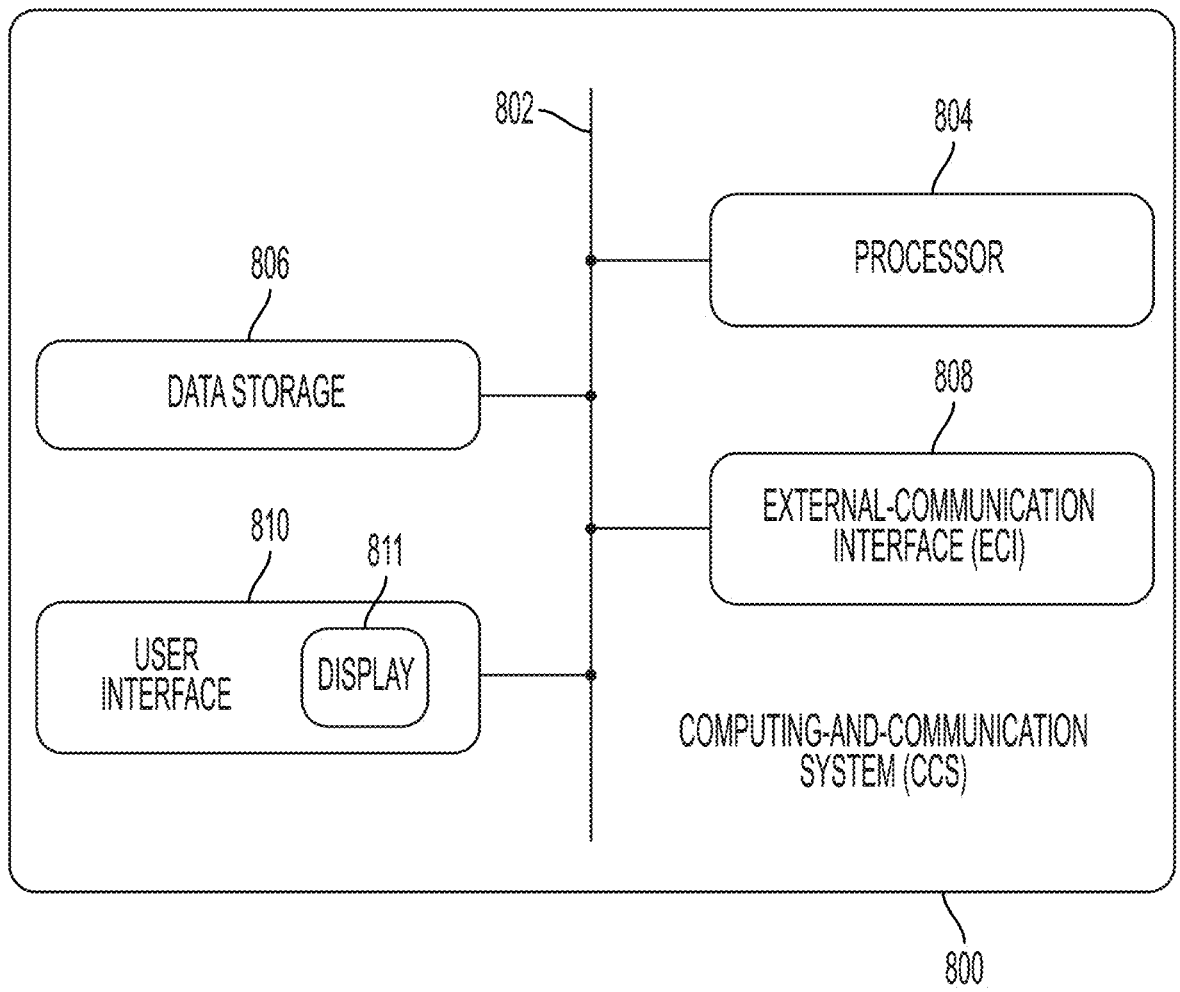
FIG. 42 is a diagram depicting an illustrative architecture of an illustrative computing-and-communication system (CCS), in accordance with at least one embodiment.

FIG. 42 is a diagram depicting an illustrative architecture of an illustrative computing-and-communication system (CCS), in accordance with at least one embodiment. In various different embodiments, one or more devices, systems, components, and/or the like could have an architecture similar to that of the CCS 800 of FIG. 42. One example of a device that could have such an architecture is the tablet 464 or more generally the patient interface 18. Another is the controller 16. Another is the anesthesia machine 90. And others could be listed here as well. As depicted in FIG. 42, the CCS 800 includes a bus 802 that communicatively interconnects a processor 804, data storage 806, an external-communication interface (ECI) 808, and a user interface 810 that includes a display 811.

The processor 804 could be a general-purpose microprocessor such as a central processing unit (CPU), and the data storage 806 could be any suitable non-transitory CRM (such as ROM, RAM, flash memory, a solid-state drive, and/or the like) that contains instructions executable by the processor 804 for carrying out the functions described herein as being performed by the particular CCS. The ECI 808 includes one or more components such as Ethernet cards, USB ports, and/or the like for wired communication and/or one or more components such as Wi-Fi transceivers, LTE transceivers, DSRC transceivers, Bluetooth transceivers, and/or the like for wireless communication such as uplink and downlink communication with a terrestrial WWAN such as an LTE network, and/or the like. The user interface 810 includes one or more user-input components such as a touchscreen, buttons, a keyboard, a microphone, and/or the like, as well as one or more output components such as the display 811 (which could be the aforementioned touchscreen), speakers, LEDs, and/or the like.

At least one embodiment of the present systems and methods relates to monitoring the breathing of a patient and to facilitating receptiveness of an anesthesia mask by pediatric patients through the use of interactive media.

An embodiment takes the form of a system for facilitating administration of gas to a patient. The system includes a mask configured to cover at least a portion of an oronasal region of a patient; a gas supply fluidly coupled to the mask, the gas supply configured to supply gas to the mask; a sensor fluidly coupled to the mask and configured to detect at least one parameter of gas exhaled into the mask by the patient and generate signals indicative thereof; a controller operably coupled to the sensor for receiving the signals from the sensor; and a patient interface operably coupled to the controller and including a display, the controller configured to generate an interactive game including graphics on the display responsive to the signals from the sensor.

In at least one embodiment, the sensor includes a pressure sensor. In at least one embodiment, the sensor includes a flow rate sensor. In at least one embodiment, the patient interface includes at least one of a mobile phone, a laptop computer, and a tablet. In at least one embodiment, the patient interface provides an indication when a predetermined volume of gas has been expelled by the user.

In at least one embodiment, the controller includes a processor and a memory including machine readable code configured to be executed by the processor. In at least one such embodiment, the controller defines a configuration mode of the interactive game where the sensitivity of the signals from the sensor can be adjusted. In at least one embodiment, the controller defines a pre-operation mode of the interactive game for setting a baseline based upon evaluated lung capacity. In at least one embodiment, the controller defines a transport mode of the interactive game for providing graphical selections to a patient.

In at least one embodiment, the controller defines an induction mode of the interactive game for encouraging breathing patterns in the patient. In at least one such embodiment, the controller further defines a post-operation mode that follows the induction mode. In at least one embodiment, the interactive game includes a balloon module for providing feedback regarding lung capacity. In at least one embodiment, the interactive game includes a curved-path module for encouraging patient breathing patterns. In at least one embodiment, the interactive game includes a wind module for facilitating patient breathing capacity.

An embodiment takes the form of a method that facilitates the administration of an inhalant to a patient. The method includes the steps of: placing a mask over at least a portion of an oronasal region of a patient; providing gas to the mask from a gas supply; detecting, via a sensor coupled to the mask, at least one parameter of gas exhaled into the mask by the patient, and generating signals indicative thereof; providing a controller in communication with the sensor for receiving the signals from the sensor; providing a patient interface in communication with the controller; and generating an interactive game on the patient interface responsive to the signals from the sensor.

In at least one embodiment, the parameter includes pressure and/or flow rate. In at least one embodiment, the patient interface includes a mobile phone, a laptop computer, and/or a tablet. In at least one embodiment, the controller defines a pre-operation mode of the interactive game for setting a baseline based upon evaluated lung capacity. In at least one embodiment, the controller defines a transport mode of the interactive game for providing graphical selections to a patient. In at least one embodiment, the controller defines an induction mode of the interactive game for encouraging patient breathing patterns. In at least one such embodiment, the controller further defines a post-operation mode that follows the induction mode.

What is claimed is:

1. A method comprising:
    providing a controller including a processor and a memory storing machine readable instructions configured to be executed by the processor;
    providing a user interface in communication with the controller, the user interface including a display configured to display graphics from the processor;
    providing a respiration device in connection with the controller and operably engaged with a user, the respiration device including a sensor configured to detect one or more respiration parameters of the user, such that the respiration device provides the one or more respiration parameters to the controller via a respiration-data stream, the sensor including a pressure sensor;
    the controller presenting a virtual experience via the display of the user interface, wherein the virtual experience of the user interface is perceptible to the user;
    the controller receiving the respiration-data stream from the respiration device, the respiration-data stream comprising one or more respiration-parameter values of one or more respiration parameters associated with ongoing respiration of the user; and
    the controller updating the virtual experience based at least in part on the one or more respiration-parameter values in the respiration-data stream, wherein:
        the virtual experience includes a plurality of sequential phases that have an associated phase sequence;

the plurality of sequential phases includes an active-induction phase that corresponds in time to the user receiving anesthetic induction via the respiration device;

the plurality of sequential phases further includes a calibration and respiration-device-acclimation phase comprising a respiration-controlled mode, wherein a respiration-parameter value is received in the respiration-data stream during the respiration-controlled mode, and the controller uses the respiration-parameter value to calibrate the virtual experience to the user's respiration-parameter value; and wherein the sequential phases correspond respectively with different visual indicia presented via the user interface.

2. The method of claim 1, wherein at least two of the different visual indicia are presented simultaneously for at least a period of time during the virtual experience.

3. The method of claim 1, wherein all of the different visual indicia are presented simultaneously for at least a period of time during the virtual experience.

4. The method of claim 1, wherein the respective different visual indicia correspond with different respective virtual locations in a virtual geographic area.

5. The method of claim 1, further comprising presenting via the user interface an insufficient-respiratory indication in response to detecting insufficient respiratory input based on the respiration-data stream.

6. The method of claim 1, wherein the virtual experience comprises an autoplay mode in which the presentation of the virtual experience is independent of any data in the respiration-data stream.

7. A system for facilitating administration of anesthesia and/or respiratory therapy comprising:
- a controller including a processor and a memory storing machine readable instructions configured to be executed by the processor;
- a user interface in communication with the controller, the user interface including a display configured to display graphics from the processor;
- a respiration device in connection with the controller and operably engaged with a user, the respiration device including a sensor configured to detect one or more respiration parameters of the user, such that the respiration device provides the one or more respiration parameters to the controller via a respiration-data stream, the sensor including a pressure sensor;
- the controller being configured to present a virtual experience via the display of the user interface, wherein the virtual experience of the user interface is perceptible to the user;
- the controller further configured to receive the respiration-data stream from the respiration device, the respiration-data stream comprising one or more respiration-parameter values of one or more respiration parameters associated with ongoing respiration of the user; and
- the controller further configured to update the virtual experience based at least in part on the one or more respiration-parameter values in the respiration-data stream, wherein:
  - the virtual experience includes a plurality of sequential phases that have an associated phase sequence;
  - the plurality of sequential phases includes an active-induction phase that corresponds in time to the user receiving anesthetic induction via the respiration device;
  - the plurality of sequential phases further includes a calibration and respiration-device-acclimation phase comprising a respiration-controlled mode, wherein a respiration-parameter value is received in the respiration-data stream during the respiration-controlled mode, and the controller uses the respiration-parameter value to calibrate the virtual experience to the user's respiration-parameter value; and
- wherein the sequential phases correspond respectively with different visual indicia presented via the user interface.

8. The system of claim 7, wherein at least two of the different visual indicia are presented simultaneously for at least a period of time during the virtual experience.

9. The system of claim 7, wherein all of the different visual indicia are presented simultaneously for at least a period of time during the virtual experience.

10. The system of claim 7, wherein the respective different visual indicia correspond with different respective virtual locations in a virtual geographic area.

11. The system of claim 7, further comprising presenting via the user interface an insufficient-respiratory indication in response to detecting insufficient respiratory input based on the respiration-data stream.

12. The system of claim 7, wherein the virtual experience comprises an autoplay mode in which the presentation of the virtual experience is independent of any data in the respiration-data stream.

* * * * *